US010548947B2

(12) United States Patent
Samulski

(10) Patent No.: US 10,548,947 B2
(45) Date of Patent: Feb. 4, 2020

(54) MODIFIED FRIEDREICH ATAXIA GENES AND VECTORS FOR GENE THERAPY

(71) Applicant: Bamboo Therapeutics, Inc., Chapel Hill, NC (US)

(72) Inventor: Richard J. Samulski, Chapel Hill, NC (US)

(73) Assignee: Bamboo Therapeutics, Inc., Chapel Hill, NC (US)

(*) Notice: Subject to any disclaimer, the term of this patent is extended or adjusted under 35 U.S.C. 154(b) by 0 days.

(21) Appl. No.: 15/340,721

(22) Filed: Nov. 1, 2016

(65) Prior Publication Data
US 2017/0128528 A1 May 11, 2017

Related U.S. Application Data

(60) Provisional application No. 62/411,980, filed on Oct. 24, 2016, provisional application No. 62/251,288, filed on Nov. 5, 2015.

(51) Int. Cl.
| *C12N 15/09* | (2006.01) |
| *C12N 15/62* | (2006.01) |
| *C12N 15/63* | (2006.01) |
| *C12N 7/00* | (2006.01) |
| *A61K 48/00* | (2006.01) |
| *A61K 35/761* | (2015.01) |
| *A61K 39/235* | (2006.01) |
| *A61K 38/17* | (2006.01) |
| *A61K 35/76* | (2015.01) |
| *C07K 14/47* | (2006.01) |

(52) U.S. Cl.
CPC .......... *A61K 38/1709* (2013.01); *A61K 35/76* (2013.01); *C07K 14/47* (2013.01); *C12N 7/00* (2013.01); *A61K 48/00* (2013.01); *C12N 2750/14143* (2013.01)

(58) Field of Classification Search
None
See application file for complete search history.

(56) References Cited

U.S. PATENT DOCUMENTS

| 6,491,907 B1 | 12/2002 | Rabinowitz et al. |
| 7,906,111 B2 | 3/2011 | Wilson et al. |
| 9,066,966 B2 | 6/2015 | Puccio et al. |
| 9,441,206 B2 | 9/2016 | Grieger et al. |
| 10,337,027 B2 | 7/2019 | Puccio et al. |
| 2014/0221462 A1 | 8/2014 | Puccio et al. |
| 2015/0313969 A1 | 11/2015 | Puccio et al. |
| 2016/0024526 A1 | 1/2016 | Puccio et al. |
| 2018/0334687 A1 | 11/2018 | Puccio et al. |

FOREIGN PATENT DOCUMENTS

| WO | 2006066066 | 6/2006 |
| WO | 2010093784 | 8/2010 |
| WO | 2013063379 | 5/2013 |
| WO | 2014118346 | 8/2014 |
| WO | 2014144229 | 9/2014 |
| WO | 2014144486 | 9/2014 |
| WO | 2014194132 | 12/2014 |
| WO | 2015013313 | 1/2015 |
| WO | 2015121501 | 8/2015 |

OTHER PUBLICATIONS

Lisowski et al., Selection and evaluation of clinically relevant AAV variants in a xenograft liver model; Nature 2014; pp. 382-386.*
Khonsari et al., Lentivirus-meditated frataxin gene delivery reverses genome instability in Friedreich ataxia patient and mouse model fibroblasts Gene Therapy (2016) 23, 846-856.*
Alexopoulou et al., 2008, "The CMV early enhancer/chicken β actin (CAG) promoter can be used to drive transgene expression during the differentiation of murine embryonic stem cells into vascular progenitors" BioMed. Central Cell Biol. 9:2.
Gao et al., 2004, "Clades of Adeno-Associated Viruses Are Widely Disseminated in Human Tissues"J. Virol. 78(12):6381.
Gardiner-Garden and Frommer, 1987, "CpG Islands in vertebrate genomes" J. Mol. Biol. 196(2):261-282.
Gray et al. (2011, "Optimizing Promoters for Recombinant Adeno-Associated Virus-Mediated Gene Expression in the Peripheral and Central Nervous System Using Self-Complementary Vectors"; Human Gene Therapy 22:1143-1153).
Isomura and Stinski, 2003, "The Human Cytomegalovirus Major Immediate-Early Enhancer Determines the Efficiency of Immediate-Early Gene Transcription and Viral Replication in Permissive Cells at Low Multiplicity of Infection"J. Virol. 17(6):3602-3614.
Kurachi et al., 1995, "Role of Intron I in Expression of the Human Factor IX Gene"J. Biol. Chem. 270(10):5276-5281).
Mori et al., 2004, "Two novel adeno-associated viruses from cynomolgus monkey:pseudotyping characterization of capsid protein" Virol. 330:375-383.
Perdomini et al., 2014, "Prevention and reversal of severe mitochondrial cardiomyopathy by gene therapy in a mouse model of Friedreich's ataxia" Nature Med. 20(5):542-547.
Puccio et al., 2001, "Mouse models for Friedreich ataxia exhibit cardiomyopathy, sensory nerve defect and Fe—S enzyme deficiency followed by intramitochondrial iron deposits" Nature Genetics 27:181-186.
Pulicherla et al., 2011, "Engineering Liver-detargeted AAV9 Vectors for Cardiac and Musculoskeletal Gene Transfer" Molecular Therapy 19(6):1070-1078.
Rabinowitz et al., 2004, "Cross-Dressing the Virion: the Transcapsidation of Adeno-Associated Virus Serotypes Functionally Defines Subgroups"J. Virol. 78(9):4421-4432.
Seznec et al., 2004, "Idebenone delays the onset of cardiac functional alteration without correction of Fe—S enzymes deficit in a mouse model for Friedreich ataxia" Human Mol. Genet. 13(10):1017-1024.
Shen, et al., 2013, "Engraftment of a Galactose Receptor Footprint onto Adeno-associated Viral Capsids Improves Transduction Efficiency"J. Biol. Chem. 288(40):28814-28823.

(Continued)

*Primary Examiner* — Maria G Leavitt

(57) ABSTRACT

The present invention relates to a modified FXN gene providing for increased expression of the encoded protein frataxin that can be used for treatment of Friedreich ataxia.

32 Claims, 8 Drawing Sheets
Specification includes a Sequence Listing.

(56) References Cited

OTHER PUBLICATIONS

Evans-Galea, et al., "FXN methylation predicts expression and clinical outcome in Friedreich ataxia" Annals of Neurology, 71(4), pp. 487-497, 2012.
Kumari et al., "Repeat Expansion Affects Both Transcription Initiation and Elongation in Friedreich Ataxia Cells" J. Biological Chem., 286(6), pp. 4209-4215, 2011.
Written Opinion of the International Searching Authority, PCT/I132016/056572, dated Jan. 3, 2017, 6 pages.
International Search Report, PCT/IB2016/056572, dated Jan. 3, 2017, 5 pages.

* cited by examiner

FIGURE 2A

WT FXN (SEQ ID NO:19)
TAGAAGACCGGTCGCCACCatgtggactctcgggcgccgcgcagtagccggcctcctggcgt
cacccagcccagcccaggcccagaccctcacccgggtcccgcggccggcagagttggcccca
ctctgcggccgccgtggcctgcgcaccgacatcgatgcgacctgcacgccccgccgcgcaag
ttcgaaccaacgtggcctcaaccagatttggaatgtcaaaaagcagagtgtctatttgatga
atttgaggaaatctggaactttgggccacccaggctctctagatgagaccacctatgaaaga
ctagcagaggaaacgctggactctttagcagagttttttgaagaccttgcagacaagccata
cacgtttgaggactatgatgtctcctttgggagtggtgtcttaactgtcaaactgggtggag
atctaggaacctatgtgatcaacaagcagacgccaaacaagcaaatctggctatcttctcca
tccagtggacctaagcgttatgactggactgggaaaaactgggtgtactcccacgacggcgt
gtccctccatgagctgctggccgcagagctcactaaagccttaaaaaccaaactggacttgt
cttccttggcctattccggaaaagatgcttgaCGAGCGGCCGCT<u>CCTAGG</u>AGCAGTATCGAT
<u>CCCAGCCCACTTTTCCCCAA</u>TACGACTAGTACTCGACTGTGCCTTCTAGTTGCCAGCCATCT
*GTTGTTTGCCCCTCCCCCGTGCCTTCCTTGACCCTGGAAGGTGCCACTCCCACTGTCCTTTC*
*CTAATAAAATGAGGAAATTGCATCGCATTGTCTGAGTAGGTGTCATTCTATTCTGGGGGGTG*
*GGGTGGGGCAGGACAGCAAGGGGGAGGATTGGGAAGACAACAGCAGGCATGCTGGGGATGCG*
*GTGGGCTCTATGGCTTCTGAGGCGGAAAGAACCAGCTTTGGACGCGTCTTAAG*

FIGURE 2B

IDT1 codon optimized FXN (SEQ ID NO:20)
TAGAAGACCGGTCGCCACCatgtggactctgggtaggcgagcggtggccggcctgttggcat
ctcctagtcctgcacaagctcaaacgctgactagagtccctcggccagcagaactggcgcca
ctttgcggccggcgcggtcttcgcactgatattgatgccacttgcacaccccggcgcgcctc
cagtaatcagcggggacttaatcaaatttggaatgtgaagaagcagtctgtgtatcttatga
atctgcggaagagcgggaccctgggccaccctggtagccttgatgaaaccacctatgagcgc
ctggccgaagagacactggacagtcttgccgagttttttgaggatctggccgacaaacctta
tacttttgaggactatgacgtgtcctttggatctggtgtattgaccgtaaaactcgggggag
accttgggacgtatgtaataaataagcagaccccaaacaagcagatctggctcagctctcca
agtagtggtcctaagagatatgattggacgggcaagaactgggtctattcccatgatggcgt
ctctttgcatgaactccttgcagcagagctgaccaaggccttgaagaccaaattggatctca
gcagcctcgcctatagtggcaaagatgcatagCGAGCGGCCGCT<u>CCTAGG</u>AGCAGTATCGAT
<u>CCCAGCCCACTTTTCCCCAA</u>TACGACTAGTACTCGACTGTGCCTTCTAGTTGCCAGCCATCT
*GTTGTTTGCCCCTCCCCCGTGCCTTCCTTGACCCTGGAAGGTGCCACTCCCACTGTCCTTTC*
*CTAATAAAATGAGGAAATTGCATCGCATTGTCTGAGTAGGTGTCATTCTATTCTGGGGGGTG*
*GGGTGGGGCAGGACAGCAAGGGGGAGGATTGGGAAGACAACAGCAGGCATGCTGGGGATGCG*
*GTGGGCTCTATGGCTTCTGAGGCGGAAAGAACCAGCTTTGGACGCGTCTTAAG*

FIGURE 2C

IDT3 - low expresser (SEQ ID NO:21)
TAGAAGACCGGTCGCCACCatgtggacactgggaaggcgcgccgtggccggtctgttggcat
caccatccccagcccaggctcagacactcacccgagtcccaagacccgcagagctggcccct
ctgtgcgggcgccgaggccttcgcaccgatatcgatgctacatgcacgccacgcagagctag
ctcaaatcagaggggactcaaccagatatggaatgtcaagaagcaaagcgtgtatctcatga
acctccggaaaagcggcaccctgggacatcccgggtctctcgacgagaccacttatgaaaga
ctggcagaggagactcttgacagtctggcggagttcttcgaagacctcgctgacaagccata
taccttcgaagattacgacgtctccttcggctctggggtgctgactgtcaagcttggcggcg
acctggggacctacgtgatcaacaagcagactccaaacaagcaaatctggctcagcagtcca
agctccggacccaagagatacgattggacaggcaagaattgggtttactcccacgacgggt
gtccctccatgagctgctggccgctgagctgacgaaggccctgaagaccaagctggatctct
cctccctggcatacagtggtaaggacgcttgaCGAGCGGCCGCT<u>CCTAGG</u>AGCAGTATCGAT
<u>CCCAGCCCACTTTTCCCCAA</u>TACG*ACTAGT**ACTCGACTGTGCCTTCTAGTTGCCAGCCATCT*
*GTTGTTTGCCCCTCCCCCGTGCCTTCCTTGACCCTGGAAGGTGCCACTCCCACTGTCCTTTC*
*CTAATAAAATGAGGAAATTGCATCGCATTGTCTGAGTAGGTGTCATTCTATTCTGGGGGGTG*
*GGGTGGGGCAGGACAGCAAGGGGGAGGATTGGGAAGACAACAGCAGGCATGCTGGGGATGCG*
*GTGGGCTCTATGGCTTCTGAGGCGGAAAGAACCAGCTTTGG**ACGCGT**CTTAAG*

FIGURE 2D

IDT4 (SEQ ID NO:22)
TAGAAGACCGGTCGCCACCatgtggactctgggccggcgggccgtagctggcttgctggcta
gcccaagtcccgcccaggctcagactctcaccagggtacccaggcccgcagagcttgctcca
ctctgcggacgcagggtctgcgaaccgatatcgacgcaacttgcacgccgcggagggcctc
ttcaaaccagagaggactcaatcaaatttggaatgtaaagaaacagagcgtgtatctcatga
acctccgaaagagtgggactcttgggcaccccggctccctggacgagactacttacgagcgc
ctggccgaagaaaccttggattccctggcggagttttttgaagacttggcagacaagcctta
taccttcgaggattacgacgtgagttttggctctggtgttcttacagtcaagctcggtggcg
accttggcacttatgtaattaacaagcagacacctaacaagcagatctggctttctagtccg
tcttccggtcccaaaaggtacgattggactggaaagaactgggtctacagtcacgacggtgt
ctccctgcacgaattgcttgcggctgagctgactaaggcgctcaaaacaaaactggatctgt
ccagccttgcctatagcgggaaggacgcatgaCGAGCGGCCGCT<u>CCTAGG</u>AGCAGTATCGAT
<u>CCCAGCCCACTTTTCCCCAA</u>TACG*ACTAGT**ACTCGACTGTGCCTTCTAGTTGCCAGCCATCT*
*GTTGTTTGCCCCTCCCCCGTGCCTTCCTTGACCCTGGAAGGTGCCACTCCCACTGTCCTTTC*
*CTAATAAAATGAGGAAATTGCATCGCATTGTCTGAGTAGGTGTCATTCTATTCTGGGGGGTG*
*GGGTGGGGCAGGACAGCAAGGGGGAGGATTGGGAAGACAACAGCAGGCATGCTGGGGATGCG*
*GTGGGCTCTATGGCTTCTGAGGCGGAAAGAACCAGCTTTGG**ACGCGT**CTTAAG*

FIGURE 2E

GenScript (SEQ ID NO:23)
TAGAAGACCGGTCGCCACCatgtggacactgggccggagagccgtcgctgggctgctggcat
caccatccccgcacaggcacagaccctgacaagagtccctcggccagcagagctggcccca
ctgtgcgggcggagaggactgcgaaccgacatcgatgctacttgtacccaaggcgagcaag
ctccaaccagcgagggctgaaccagatttggaatgtgaagaaacagtctgtctacctgatga
atctgagaaagagcggcactctgggacaccctggcagcctggacgagaccacctacgagcgg
ctggccgaggaaaccctggattccctggccgagttctttgaagacctggctgataagccata
caccttcgaagactatgacgtgagcttcggcagcggcgtgctgacagtcaaactgggcgggg
acctgggaacatacgtgatcaacaagcagactcctaacaagcagatttggctgtctagtccc
tcaagcggccctaagaggtacgactggacagggaaaaactgggtgtatagtcacgatggcgt
ctcactgcatgagctgctggccgctgaactgactaaagccctgaaaactaaactggacctgt
cttccctggcatactctggcaaggacgcctgaCGAGCGGCCGCT<u>CCTAGG</u>AGCAGTATCGAT
<u>CCCAGCCCACTTTTCCCCAAT</u>ACGACTAGTACTCGACTGTGCCTTCTAGTTGCCAGCCATCT
GTTGTTTGCCCCTCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAACAGCAGGCATGCTGGGGATGCG
GTGGGCTCTATGGCTTCTGAGGCGGAAAGAACCAGCTTTGG*ACGCGT*CTTAAG

FIGURE 2F

GenScript (low CpG) (SEQ ID NO:24)
TAGAAGACCGGTCGCCACCatgtggactctgggccggagagcagtggcaggactgctggcaa
gtccatcacctgctcaggcacagactctgacaagagtcccaagacctgcagagctggctcca
ctgtgcgggaggcgcggactgagaacagacatcgatgctacatgtactcctcgacgggcaag
ctccaaccagcgagggctgaaccagatttggaatgtgaagaaacagtccgtctacctgatga
atctgaggaagtcaggcaccctggggcacccaggaagtctggacgagaccacatatgaacgg
ctggctgaggaaacactggattctctggccgagttctttgaagacctggctgataagcccta
cacattcgaagactatgatgtgagctttggatccggcgtgctgactgtcaaactgggcgggg
acctgggcacttacgtgatcaacaagcagaccccctaacaagcagatttggctgtctagtcct
tcaagcggaccaaagcggtacgactggaccggcaaaaactgggtgtattctcacgatgggt
cagtctgcatgagctgctggccgctgaactgaccaaggccctgaagacaaaactggacctgt
cctctctggcatatagcggaaaagatgcctgaCGAGCGGCCGCT<u>CCTAGG</u>AGCAGTATCGAT
<u>CCCAGCCCACTTTTCCCCAAT</u>ACGACTAGTACTCGACTGTGCCTTCTAGTTGCCAGCCATCT
GTTGTTTGCCCCTCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAACAGCAGGCATGCTGGGGATGCG
GTGGGCTCTATGGCTTCTGAGGCGGAAAGAACCAGCTTTGG*ACGCGT*CTTAAG

MODIFIED FRIEDREICH ATAXIA GENES AND VECTORS FOR GENE THERAPY

RELATED APPLICATIONS

This application claims the benefit of U.S. Provisional Application No. 62/251,288, filed Nov. 5, 2015, and U.S. Provisional Application No. 62/411,980, filed Oct. 24, 2016, the contents of each of which applications are hereby incorporated by reference in their entirety.

SEQUENCE LISTING

The instant application contains a Sequence Listing which has been submitted electronically as a text file in ASCII format and is hereby incorporated by reference in its entirety. Said text file, created on Nov. 1, 2016, is named PC45291A_Seq_Listing_ST25.txt and is 71,065 bytes in size.

FIELD OF THE INVENTION

The invention relates to modified frataxin (FXN) genes, vectors comprising the modified FXN genes, methods of using the modified FXN genes, and vectors containing them in the treatment of Friedreich ataxia, including cardiomyopathy and/or neurodegenerative disease associated therewith, by providing increased expression levels of non-mutated (wild type) mitochondrial protein frataxin.

BACKGROUND OF THE INVENTION

Friedreich ataxia (FRDA) is associated with reduction of expression of and/or mutation in the FXN gene that encodes for the mitochondria protein frataxin. FRDA is an autosomal recessive disease, meaning individuals only develop this disease if they inherit a defective gene from both parents. FRDA is caused by mutations in the FXN gene that results in reduction of mRNA and protein levels of frataxin. Defective frataxin expression causes critical metabolic changes, including redox imbalance and ATP deficiency.

FRDA is a neurodegenerative disease that affects children and young adults and leads to progressive disability and premature death. Neurological signs are associated with degeneration of sensory neurons and the flow of sensory information through the peripheral nerves and the spinal cord is severely affected. There is also some impairment of muscle-controlling signals from the cerebellum and spinal cord. These problems lead to the progressive loss of balance, coordination and muscle strength that characterize FRDA. Further, patients often develop a hypertrophic cardiomyopathy that is likely the cause of premature death. Enlargement of the heart, irregular heartbeat and other symptoms of heart trouble are evident.

It is believed that the frataxin protein regulates the levels of iron inside the mitochondria which is necessary for using oxygen to produce energy. Frataxin appears to act as a storage depot for iron, releasing it only when it's needed for synthesis of enzymes in the mitochondrial. Therefore, a deficiency of frataxin results in a deficiency of these enzymes and further reduces mitochondrial function which likely explains why Friedreich ataxia affects cells of the nervous system and heart.

To date, no treatment exists for stopping or slowing down the negative effects of FRDA. Current therapeutic approaches in clinical use or under evaluation are directed at alleviating symptoms and maximizing quality of life. Physical therapy and speech therapy have been used to improve movement. Further, some medications have been used to treat heart disease. Thus, there is an important need for a novel therapeutic approach to treat the symptoms associated with FRDA.

SUMMARY OF THE INVENTION

Disclosed and exemplified herein are modified nucleic acids encoding frataxin (FXN) and vectors comprising the modified nucleic acid and methods of treating a disease mediated by decreased level of FXN by administering the modified nucleic acid or the vector comprising the nucleic acid to a patient in need thereof.

Those skilled in the art will recognize, or be able to ascertain using no more than routine experimentation, many equivalents to the specific embodiments of the invention described herein. Such equivalents are intended to be encompassed by the following embodiments (E).

E1. A modified FXN gene for treating FRDA in a human subject wherein the modified FXN gene has been modified to alter the content of GC nucleotides and/or to have a reduced number of CpG dinucleotides.

E2. The modified FXN gene of embodiment 1 wherein the reduced number of CpG dinucleotides is in an amount sufficient to suppress the silencing of gene expression due to the methylation of CpG motifs.

E3. The modified FXN gene of embodiment 1 wherein the content of GC nucleotides is greater than 10%, 20%, 30%, 40%, 50%, 60% or 70% relative to the wild-type gene.

E4. The modified FXN gene of embodiment 3, having a codon adaptation index that is >0.75, >0.80, >0.85, >0.90, or >0.95.

E5. The modified FXN gene of embodiment 3, comprising a sequence selected from any one of SEQ ID NOs: 3 to 9.

E6. The modified FXN gene of embodiment 1 wherein the content of GC nucleotides is less than 10%, 20%, 30%, 40%, 50%, 60% or 70% relative to the wild-type gene.

E7. The modified FXN gene of embodiment 1 included in a viral vector or plasmid.

E8. The modified FXN gene of embodiment 7, wherein the viral vector is a self-complementary AAV sequence.

E9. The modified FXN gene of embodiment 8, wherein the viral vector is selected from the group consisting of AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAV Hu.26, AAV2i8, AAV2G9, rhAAV10, rhAAV74, RHM4-1, RHM15-1, RHM15-2, RHM15-3/RHM15-5, RHM15-4, RHM15-6, AAV2-TT, AAV2-TT-S312N, AAV3B-S312N, AAV-LK03, and combinations and variants thereof.

E10. The modified FXN gene of embodiment 8, wherein the viral vector is an ancestral AAV vector.

E11. The modified FXN gene of embodiment 8, wherein the viral vector is a chimeric AAV including a combination of AAV backbones from AAV2, AAV3B, AAV6 or AAV8 and further comprising a galactose (Gal) binding footprint from AAV9.

E12. The modified FXN gene of embodiment 1, wherein frataxin protein has an amino acid sequence of SEQ ID NO. 1 or a functional fragment thereof.

E13. A method for treating a disease associated with frataxin deficiency in a subject in need thereof, comprising administering to said subject a therapeutically effective amount of a modified FXN gene wherein the modified FXN gene has been modified to increase or decrease content of GC nucleotides and/or to reduce the number of CpG dinucleotides.

E14. The method of embodiment 13, wherein the modified FXN gene encodes the frataxin protein having the amino acid sequence of SEQ ID NO. 1.

E15. The method of embodiment 13, wherein the modified FXN gene is expressed in target cells, wherein the target cells are cardiac or neuron cells E16. The method of embodiment 13, wherein the modified FXN gene is delivered in a viral or non-viral vector to the target cells.

E17. The method of embodiment 16, wherein the vector is delivered by systemic injection or by direct cardiac or intracranial injection.

E18. A method of treating Friedreich ataxia (FRDA) in a subject in need thereof, the method comprising: providing at least one recombinant virus vector comprising a modified FXN gene, wherein the modified FXN gene has been modified to increase or decrease the content of GC nucleotides and/or to reduce the amount of CpG dinucleotides; and administering the recombinant virus vector to the subject under conditions such that the modified FXN gene is expressed at a level which produces a therapeutically effective amount of frataxin in cardiac and/or neuron tissue of the subject.

E19. The method of embodiment 18, wherein the recombinant virus vector is administered to neurons or heart muscles cells of the subject.

E20. A host cell transfected with a modified FXN gene that encodes a frataxin peptide or a functional fragment thereof wherein the modified FXN gene has been modified to increase or decrease content of GC nucleotides and/or to reduce number of CpG dinucleotides.

E21. A process of preparing a frataxin peptide or fragment thereof comprising:
transfecting a host cell with a modified FXN gene that encodes the frataxin peptide or functional fragment thereof; and maintaining the host cell under biological conditions sufficient for expression of the frataxin peptide.

E22. The process of embodiment 21, wherein the modified FXN gene has increased levels of GC nucleotides and/or reduced levels of CpG dinucleotides compared with the nucleic acid sequence of wild type frataxin as set forth in SEQ ID NO:2.

E23. A pharmaceutical composition comprising a modified FXN gene, wherein the modified FXN gene has an increased or decreased content of GC nucleotides and/or a reduced number of CpG dinucleotides, and a pharmaceutically acceptable carrier.

E24. A method for treating FRDA comprising delivering to a subject in need of treatment, a vector comprising a modified polynucleotide sequence encoding a FXN gene, wherein the FXN gene is expressed in the target cells, thereby treating FRDA in the subject. The target cells are preferably cardiac or neuron cells and the vector is preferably delivered to the target cells via direct cardiac or intracranial injection.

E25. The modified nucleic acid of embodiment 1, wherein the modified nucleic acid has a reduced GC content, relative to the wild type gene, that being 20%, 30%, 40%, 50%, or 60% less than the wild type gene while still having the same expression level as the wild type. Silent mutations can be introduced into the coding sequence in order to reduce the GC content of the gene.

E26. A modified nucleic acid encoding FXN with a reduced level of CpG dinucleotides.

E27. A modified nucleic acid encoding FXN (also referred to as a "modified FXN gene") for treating FRDA in a human subject in need thereof, wherein the modified FXN gene had been modified to increase GC content and reduce certain cis motifs relative to the wild type nucleic acid sequence encoding FXN set forth as SEQ ID NO:2.

E28. A modified FXN gene having a reduced number of CpG dinucleotides in an amount to suppress the silencing of gene expression due to the methylation of CpG motifs compared with the number of CpG dinucleotides present in the wild type nucleic acid sequence encoding FXN set forth as SEQ ID NO:2.

E29. A method of treating FRDA in a subject, the method comprising:
providing at least one recombinant virus vector comprising a modified FXN gene of any one of embodiments 1-12, 23, and 25-28, and administering the recombinant virus vector to the subject under conditions such that the modified FXN gene is expressed at a level which produces a therapeutically effective amount of frataxin in cardiac and or neuron tissue of the subject.

E30. A method for reducing the effects of or treating Friedreich ataxia in neurons and heart muscles cells of a subject in need thereof, comprising administering to said subject a therapeutically effective amount of a recombinant virus vector which comprises a modified FXN nucleic acid encoding the protein frataxin.

E31. A method for treating Friedreich ataxia in a subject in need thereof, including gene therapy based on administration of a nucleic acid comprising a nucleotide sequence selected from the group consisting of a sequence of SEQ ID NOs:3-9.

E32. A composition comprising an adeno-associated virus (AAV) vector comprising a modified FXN gene, or functional fragment thereof, wherein the AAV vector comprises a single stranded AAV vector genome, a double-stranded AAV vector genome or a self-complementary (sc) AAV vector genome.

E33. An expression vector comprising a polynucleotide that includes a modified FXN gene or fragment thereof.

E34. The vector of embodiment 33, wherein the AAV comprises a capsid of a serotype selected from the group consisting of AAV1, AAV2, AAV3, AAV4, AAV5, AAV6, AAV7, AAV8, AAV9, AAV10, AAV11, AAV12, rhAAV10, rhAAV74, RHM4-1, RHM15-1, RHM15-2, RHM15-3/ RHM15-5, RHM15-4, RHM15-6, AAV Hu.26, AAV1.1 (SEQ ID NO:15), AAV2.5 (SEQ ID NO. 13), AAV6.1 (SEQ ID NO:17), AAV6.3.1 (SEQ ID NO:18), AAV9.45, AAV2i8 (SEQ ID NO:29), AAV2G9, AAV2-TT (SEQ ID NO:31), AAV2-TT-S312N (SEQ ID NO:33), AAV3B-S312N, and AAV-LK03.

E35. The vector of embodiment 34, further comprising a AAV1.1 capsid wherein amino acid residue 265 is deleted (SEQ ID NO: 15), an AAV 6.1 capsid wherein amino acid residue 265 is deleted (SEQ ID NO: 17), an AAV 6.3.1 capsid wherein amino acid residue 265 is deleted and amino acid residue 531 is changed from a Lys to a Glu (SEQ ID NO: 18). The nucleotide sequence of wildtype AAV 1 capsid is shown in (SEQ ID NO: 14) and the nucleotide sequence of wildtype AAV 6 capsid is set forth in (SEQ ID NO: 16).

E36. A chimeric AAV virus vector comprising the modified FXN gene of any one of embodiments 1-12, 23, and 25-28, further comprising a capsid that includes the combination of AAV backbones from AAV2, AAV3, AAV6, AAV8, with a galactose (Gal) binding footprint from AAV9. Specifically, the galactose (Gal) binding footprint from AAV9 is grafted onto the heparin sulfate-binding AAV serotype 2 to improve transduction efficiency.

E37. A chimeric AAV virus vector comprising the modified FXN gene of any one of embodiments 1-12, 23, and 25-28, further comprising wherein the vector capsid includes tyrosine mutants in combination with 265 deletion mutations of AAV1 and or AAV6 as well as addition of a galactose binding footprint to the capsid protein.

E38. A chimeric AAV virus vector comprising the modified FXN gene of any one of embodiments 1-12, 23, and 25-28, further comprising a targeting peptides inserted in the HI structure loop of AAV or in position of 585 aa in AAV 2 backbone. Additionally, ancestral AAV vectors may be used for therapeutic in vivo gene therapy. Notably, the use of the virus particles assembled from ancestral viral sequences exhibit reduced susceptibility to pre-existing immunity in current day human population than do contemporary viruses or portions thereof.

E39. A host cell comprising the modified FXN gene of any one of embodiments 1-12, 23, and 25-28.

E40. A process of preparing a frataxin peptide or fragment thereof comprising: transfecting a host cell with the modified FXN gene of any one of embodiments 1-12, 23, and 25-28, and maintaining the host cell under biological conditions sufficient for expression of the frataxin peptide.

E41. Use of a modified FXN gene of any one of embodiments 1-12, 23, and 25-28, in the treatment of Friedreich ataxia.

E42. A pharmaceutical composition comprising a modified FXN gene for treating Friedreich ataxia that causes degeneration of neurons and cells in the cardiac tissues of a human subject wherein the modified FXN gene has an increased amount of GC nucleotides, decreased amount of GC nucleotides and/or has a reduced number of CpG dinucleotides; and a pharmaceutically acceptable carrier.

E43. An expression optimized nucleic acid encoding frataxin comprising a nucleic acid sequence selected from any one of SEQ ID NOs:3-9.

E44. A modified nucleic acid encoding frataxin comprising the amino acid set forth in SEQ ID NO:1, wherein the nucleic acid has a GC content of at least 55%, a decreased number of CpG dinucleotides compared with the nucleic acid sequence of SEQ ID NO:2, a codon adaptation index (CAI) of at least 0.8, and wherein it is expressed at a greater level compared with the level of expression of wild type frataxin comprising the nucleic acid sequence of SEQ ID NO:2.

E45. The modified nucleic acid of embodiment 44, wherein the CAI is at least 0.86.

E46. The modified nucleic acid of embodiment 44, wherein the CAI is at least 0.95.

E47. The modified nucleic acid of embodiment 44, wherein the CAI is at least 0.98.

E48. The modified nucleic acid of any one of embodiments 44-47, wherein the GC content is at least 61%.

E49. The modified nucleic acid of any one of embodiments 44-47, wherein the GC content is at least 69%.

E50. The modified nucleic acid of any one of embodiments 44-49, wherein the number of CpG dinucleotides is from about 114 to 124.

E51. A modified nucleic acid encoding frataxin (FXN) comprising the amino acid sequence set forth in SEQ ID NO:1, wherein said nucleic acid is expressed at a greater level compared with the expression level of the wild type FXN nucleic acid sequence of SEQ ID NO:2, and wherein said modified nucleic acid comprises at least one characteristic selected from the group consisting of: a GC content of at least 55%, a number of CpG dinucleotides not greater than 124, and a codon adaptation index (CAI) of at least 0.76.

E52. The modified nucleic acid of embodiment 51, said nucleic acid comprising at least one characteristic selected from the group consisting of: a CAI of at least 0.86, at least 0.95, or at least 0.98; a GC content is at least 57%, at least 61%, or at least 69%; a number of CpG dinucleotides is less than 124; and a nucleic acid sequence selected from the group consisting of a sequence as set forth in SEQ ID NOs:3-9.

E53. A modified nucleic acid encoding FXN, wherein said nucleic acid is expressed at a greater level compared with the level of expression of the wild type FXN nucleic acid sequence of SEQ ID NO:2, and wherein the nucleic acid comprises at least one of: a nucleic acid sequence selected from the group consisting of SEQ ID NOs:3-9; a GC content of at least 55%; a number of CpG dinucleotides not greater than 117; and a CAI of at least 0.86.

E54. The modified nucleic acid of embodiment 53, wherein the nucleic acid sequence is selected from the group consisting of SEQ ID NO:5 and SEQ ID NO:7.

E55. The modified nucleic acid of claim any one of embodiments 43-54, comprising the nucleic acid sequence of SEQ ID NO:7.

E56. The modified nucleic acid of any one of embodiments 1-12, 23, 25-28 and 43-55, further comprising a nucleic acid sequence encoding at least one AAV terminal repeat (TR).

E57. The modified nucleic acid of embodiment 55 wherein the nucleic acid single stranded, double stranded, and/or self complementary.

E58. The modified nucleic acid of embodiment 57, wherein the nucleic acid is self complementary.

E59. The modified nucleic acid of any one of embodiments 1-12, 23, 25-28, and 43-58, further comprising an enhancer.

E60. The modified nucleic acid of embodiment 59, wherein the enhancer is a cytomegalovirus (CMV) immediate-early enhancer.

E61. The modified nucleic acid of any one of embodiments 1-12, 23, 25-28, and 43-60, further comprising a promoter.

E62. The modified nucleic acid of any one of embodiments 1-12, 23, 25-28, and 43-61, wherein the promoter is constitutive or regulated.

E63. The modified nucleic acid of embodiment 62, wherein the promoter is regulated.

E64. The modified nucleic acid of embodiment 63, wherein the promoter inducible or repressible.

E65. The modified nucleic acid of any one of embodiments 1-12, 23, 25-28, and 43-64, further comprising a nucleic acid sequence encoding a collagen stabilization sequence (CSS).

E66. The modified nucleic acid of any one of embodiments 1-12, 23, 25-28, and 43-65, further comprising a stop codon.

E67. The modified nucleic acid of any one of embodiments 1-12, 23, 25-28, and 43-66, further comprising a polyadenylation (polyA) signal sequence.

E68. The modified nucleic acid of embodiment 67, wherein the promoter is selected from the group consisting of a chicken beta-actin (CBA) promoter, a cytomegalovirus (CMV) promoter, a CMV enhancer/CBA promoter (CBh), and a synthetic CAG promoter.

E69. The modified nucleic acid of embodiment 68, wherein the promoter is a CBh promoter.

E70. The modified nucleic acid of any one of embodiments 1-6, 12, 25-28, and 44-69, further comprising a nucleic acid sequence encoding a collagen stabilization sequence (CSS).

E71. A recombinant AAV vector (rAAV) comprising the modified nucleic acid encoding FXN of any one of embodiments 1-12, 23, 25-28, and 43-70.

E72. The rAAV of embodiment 71, wherein the rAAV comprises a capsid selected from the group consisting of a capsid from AAV1, AAV2, AAV3, AAV4, AAV5, AAV6, AAV7, AAV8, AAV9, AAV10, AAV11, AAV12, AAVrh10, AAVrh74, AAV2.5 (SEQ ID NO. 13), AAV hu.26, AAV1.1, AAV2.5, AAV6.1, AAV6.3.1, AAV2i8, AAV2G9, AAV9.45, AAV2i8G9, RHM4-1, RHM15-1, RHM15-2, RHM15-3/ RHM15-5, RHM15-4, RHM15-6, AAV2-TT, AAV2-TT-S312N, AAV3B-S312N, and AAV-LK03.

E73. The rAAV of embodiment 72, wherein the capsid is selected from the group consisting of AAV2-TT, AAV2-TT-S312N, and AAV2i8 capsid.

E74. The rAAV of embodiment 73, wherein the modified nucleic acid comprises the sequence of SEQ ID NO:7 and wherein the capsid is selected from an AAV2i8 capsid and an AAV2-TT-S312N capsid.

E75. The rAAV of embodiment 74, wherein the nucleic acid further comprises two AAV terminal repeat sequences flanking the sequence encoding FXN, and further comprises a CBh promoter upstream of the sequence encoding FXN.

E76. The rAAV of embodiment 75, said nucleic acid further comprising a collagen stabilization sequence (CSS; SEQ ID NO:25) 3' from the sequence encoding FXN.

E77. The rAAV of any one of embodiments 71-76, wherein the nucleic acid comprises a bovine growth hormone polyA (bGHpolyA) signal sequence.

E78. A rAAV vector comprising an AAV2i8 capsid wherein VP1 comprises the amino acid of SEQ ID NO:29, and further comprising a nucleic acid comprising, from 5' to 3':
  (a) an AAV2 terminal repeat (TR);
  (b) a CBh promoter comprising the nucleic acid sequence of SEQ ID NO:26;
  (c) a modified nucleic acid encoding FXN comprising a nucleic acid sequence selected from the group consisting of SEQ ID NOs:3-9;
  (d) a CSS having the sequence of SEQ ID NO:25;
  (e) a bGHpolyA signal sequence having the sequence of SEQ ID NO:27; and
  (f) an AAV2 TR.

E79. A rAAV vector comprising an AAV2-TT capsid wherein VP1 comprises the amino acid of SEQ ID NO:31, and further comprising a nucleic acid comprising, from 5' to 3':
  (a) an AAV2 TR;
  (b) a CBh promoter comprising the nucleic acid sequence of SEQ ID NO:26;
  (c) a modified nucleic acid encoding FXN comprising a nucleic acid sequence selected from the group consisting of SEQ ID NOs:3-9;
  (d) a CSS having the sequence of SEQ ID NO:25;
  (e) a bGHpolyA signal sequence having the sequence of SEQ ID NO:27; and
  (f) an AAV2 TR.

E80. A rAAV vector comprising an AAV2-TT-S312N capsid wherein VP1 comprises the amino acid of SEQ ID NO:33, and further comprising a nucleic acid comprising, from 5' to 3':
  (a) an AAV2 TR;
  (b) a CBh promoter comprising the nucleic acid sequence of SEQ ID NO:26;
  (c) a modified nucleic acid encoding FXN comprising a nucleic acid sequence selected from the group consisting of SEQ ID NOs:3-9;
  (d) a CSS having the sequence of SEQ ID NO:25;
  (e) a bGHpolyA signal sequence having the sequence of SEQ ID NO:27; and
  (f) an AAV2 TR.

E81. The rAAV vector of any one of embodiments 71-80, wherein the modified nucleic acid encoding FXN comprises the nucleic acid sequence of SEQ ID NO:7.

E82. A rAAV vector for treating Friedreich ataxia in a subject in need thereof, wherein said vector comprises the modified nucleic acid encoding frataxin of any one of embodiments 1-6, 12, 25-28 and 71-81.

E83. A pharmaceutical composition comprising the rAAV vector of any one of embodiments 7-11, 33-39, and 71-82, and a pharmaceutically acceptable carrier.

E84. A method of treating FRDA in a subject, the method comprising administering at least one of: a modified nucleic acid encoding frataxin of any one of embodiments 1-12, 23, 25-28 and 43-70; a rAAV vector of any one of embodiments 7-11, 33-39 and 71-82; and the pharmaceutical composition of embodiment 83.

E85. The method of embodiment 84, wherein the rAAV vector of any one of embodiments 7-11, 33-39, and 71-82, is administered systemically, or by direct cardiac or intracranial administration.

E86. The method of embodiment 85, wherein the rAAV vector of any one of embodiments 71-82 is administered intracranially.

E87. The method of embodiment 85, wherein the rAAV vector of any one of embodiments 71-82 is directly administered into the heart.

E88. The method of embodiment 84, wherein the modified nucleic acid encoding FXN comprises the nucleic acid sequence of SEQ ID NO:6.

E89. The method of embodiment 84, wherein the modified nucleic acid encoding FXN comprises the nucleic acid sequence of SEQ ID NO:7.

E90. A method of treating a disease, disorder or condition mediated by a decreased level of FTX, the method comprising administering at least one of: the modified nucleic acid encoding frataxin of any one of embodiments 1-6, 12, 25-28 and 43-70; the rAAV vector of any one of embodiments 7-11, 33-39 and 71-82; and the pharmaceutical composition of embodiment 83.

E91. A host cell comprising a modified nucleic acid encoding FXN of any one of embodiments 1-6, 12, 25-28 and 43-70.

E92. The host cell of embodiment 91, wherein the cell is selected from the group consisting of VERO, WI38, MRC5, A549, HEK293 cells, B-50 or any other HeLa cells, HepG2, Saos-2, HuH7, and HT1080.

E93. The host cell of embodiment 92, wherein the host cell is a HEK293 adapted to growth in suspension culture.

E94. The host cell of any one of embodiments 91-93, wherein the cell is a HEK293 cell having ATCC No. PTA 13274.

E95. A packaging cell comprising a rAAV vector of any one of embodiments 7-11, 33-39, and 70-82, wherein said cell further comprises at least one nucleic acid encoding an AAV Rep protein, at least one nucleic acid encoding an AAV Cap protein, and at least one nucleic acid encoding a helper function.

E96. A method for producing a rAAV vector, the method comprising culturing the cell of any one of embodiments 91-95 under conditions where rAAV is produced.

E97. The method of embodiment 96, further comprising isolating the rAAV produced.

E98. Use of at least one of: the modified nucleic acid encoding frataxin of any one of embodiments 1-6, 12, 25-28 and 43-70; the rAAV vector of any one of embodiments 7-11, 33-39 and 71-82; and the pharmaceutical composition of embodiment 83 to increase the level of frataxin in a cell.

E99. The modified nucleic acid encoding frataxin of any one of embodiments 1-6, 12, 25-28 and 43-70; the rAAV vector of any one of embodiments 7-11, 33-39 and 71-82; and the pharmaceutical composition of embodiment 83 for use in increasing the level of frataxin in a subject.

E100. The modified nucleic acid encoding frataxin of any one of embodiments 1-6, 12, 25-28 and 43-70; the rAAV vector of any one of embodiments 7-11, 33-39 and 71-82; and the pharmaceutical composition of embodiment 83 for use in treating Friedreich ataxia in a subject.

Other features and advantages of the invention will be apparent from the following detailed description, drawings, exemplary embodiments and claims

BRIEF DESCRIPTION OF THE DRAWINGS

FIGS. 1A and 1B both show the results of expression in HeLa cells of frataxin from selected modified nucleic acids encoding FXN compared to a wild type nucleic acid (lane 1). Extracts from HeLa cells comprising the following modified nucleic acids were examined to detect FXN produced in the cells. Frataxin was detected by Western blotting using an anti-frataxin antibody detected using a secondary antibody conjugated with HRP (horse radish peroxidase) for chemiluminescence detection by exposure of the Western blot to light sensitive film. The lanes were loaded with extracts from HeLa cells transfected with the following modified nucleic acids encoding frataxin: lane 1: wild type control nucleic acid; lane 2: IDT2; lane 3: IDT5; lane 4: JCAT; lane 5: GeneArt; lane 6: Genscript (control); and lane 7: Genscript (low CpG).

FIGS. 2A-2F show the sequence of various modified FXN gene constructs for cloning into the self-complementary rAAV vector pTRs-KS-CBh-EGFP-bGHpolyA—where the EGFP marker gene was replaced with either wild type FXN gene (SEQ ID NO:2) or a modified version thereof (e.g., SEQ ID NOs:3-9). Each figure shows WT FXN (FIG. 2A) or a modified FXN gene (FIGS. 2B-2F). Each construct comprises (from 5' to 3') an AgeI cut site, the FXN/modified FXN gene, AvrII cut site, a collagen stability sequence (CSS), a SpeI cut site, a bGHpolyA signal sequence, and a MluI cut site. FIG. 2A shows the pTRs-KS-CBh-VVT FXN-bGHpolyA construct (SEQ ID NO:19); FIG. 2B shows the Integrated DNA Technologies IDT 1 (IDT1) modified FXN gene construct pTRs-KS-CBh-IDT1 FXN-bGHpolyA (SEQ ID NO:20); FIG. 2C shows IDT3 modified FXN gene construct pTRs-KS-CBh-IDT3 FXN-bGHpolyA (SEQ ID NO:21); FIG. 2D shows the IDT4 modified FXN gene construct pTRs-KS-CBh-IDT4 FXN-bGHpolyA (SEQ ID NO:22); FIG. 2E shows the GenScript modified FXN gene construct pTRs-KS-CBh-GenScript FXN-bGHpolyA (SEQ ID NO:23); and FIG. 2F shows the GenScript (low CpG) modified FXN gene construct pTRs-KS-CBh-Genscript (low CpG) FXN-bGHpolyA (SEQ ID NO:24), each sequence includes the elements (e.g., AgeI, AvrII, CSS, SpeI, bGHpolyA, and MluI) which are indicated as follows, from 5' to 3', in FIGS. 2A-2F: an AgeI cut site (ACCGGT) indicated in bold; the FXN gene in lower case letters, an AvrII cut site (CCTAGG) indicated by underlining; a sequence encoding a collagen stabilization sequence (CSS) indicated by double underlining; an SpeI cut site (ACTAGT) indicated in bold underlined; a bovine growth hormone poly-adenylation signal sequence (bGHpolyA) indicated in italics; and a MluI cut site (ACGCGT) indicated in bold italics. The FXN gene in the construct is under the control of the CBh promoter upstream from the AgeI cut site. The sequence of the CBh promoter is not shown in FIGS. 2A-2F, but is set forth in SEQ ID NO:25.

FIG. 4A shows the cardiac phenotype for, from left to right within each grouping: control males, treated mutants and untreated mutants, where the groupings are: EF (ejection fraction), FS (fractional shortening); LV Vol_d (left ventricle volume diastolic); and LV Vol_s (left ventricle volume systolic). FIG. 4B shows the baseline cardiac phenotype for female mice groups: control (circles); treated mutants (squares); and untreated mutants (triangles).

FIG. 5A shows the cardiac phenotype of control (circles), treated mutant (squares) and untreated mutant (triangles) male mice 14 days after rAAV-FXN injection. The abbreviations are as follows: AoV SV (aortic valve stroke volume); AoV CO (aortic valve cardiac output); FS (fractional shortening); and LV Mass AW (left ventricle mass anterior wall). FIG. 5B shows the cardiac phenotype of control (circles), treated mutant (squares) and untreated mutant (triangles) female mice 14 days after rAAV-FXN injection. The abbreviations are as follows: ES (ejection fraction): FS (fractional shortening); AoV SV (aortic valve stroke volume); AoV CO (aortic valve cardiac output).

FIG. 6A shows the left ventricle mass (LVM) echocardiography assessment for all three mouse groups over successive weeks, i.e., at 3 weeks of age (time of rAAV administration), 5 weeks of age (14 days post-rAAV administration) and 7 weeks of age (28 days post-rAAV administration) where treatment was administered at the age of 5 weeks. FIG. 6B shows the shortening factor (SF) echocardiography assessment for all three mouse groups over successive weeks. FIG. 6C shows the cardiac output echocardiography assessment for all three mouse groups over successive weeks. The data are mean±S.E.M of 8 mice per group. The data of Mck mutant mice were compared to the Mck positive control group using multiple t-tests comparisons (Sidak-Bonferroni method). *p<0.05.

DETAILED DESCRIPTION OF THE INVENTION

Definitions

Figure 1A:
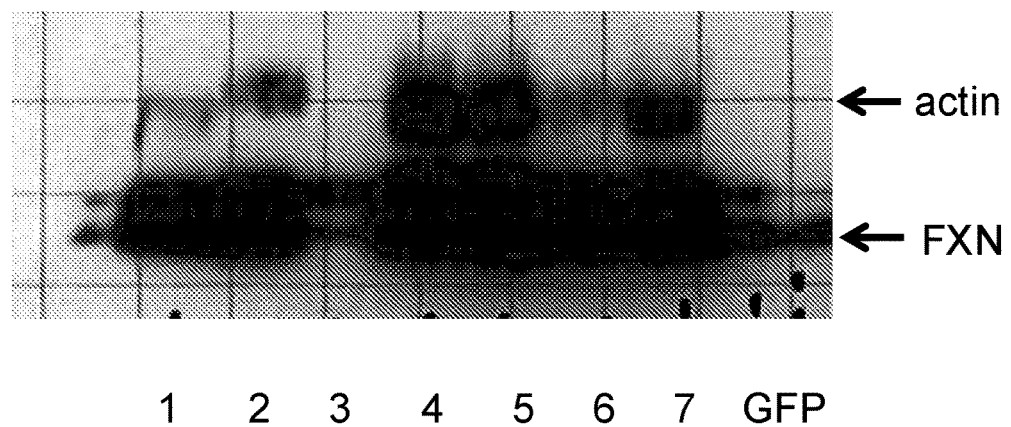
FIGS. 1A and 1B.

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

The term "about," as used herein, when referring to a measurable value such as an amount of the biological activity, length of a polynucleotide or polypeptide sequence, content of G and C nucleotides, codon adaptation index, number of CpG dinucleotides, dose, time, temperature, and the like, is meant to encompass variations of 20%, 10%, 5%, 1%, 0.5% or even 0.1% of the specified amount.

As used herein, the term "and/or" refers to and encompasses any and all possible combinations of one or more of the associated listed items, as well as the lack of combinations when interpreted in the alternative ("or").

AAV "rep" and "cap" genes refer to polynucleotide sequences encoding replication and encapsidation proteins of adeno-associated virus. AAV rep and cap are referred to herein as AAV "packaging genes."

The present disclosure provides a recombinant adeno-associated virus (rAAV) vector. "AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector") or simply, an "AAV vector." The term "AAV" includes, for example, AAVs of various serotypes, e.g., AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10, including AAVrh10), AAVrh74, AAV type 12 (AAV-12), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, and so on.

The various serotypes of AAV are attractive for several reasons, most prominently that AAV is believed to be non-pathogenic and that the wildtype virus can integrate its genome site-specifically into human chromosome 19 (Linden et al., 1996, Proc Natl Acad Sci USA 93:11288-11294). The insertion site of AAV into the human genome is called AAVS1. Site-specific integration, as opposed to random integration, is believed to likely result in a predictable long-term expression profile.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC-002077 (AAV-1), AF063497 (AAV-1), NC-001401 (AAV-2), AF043303 (AAV-2), NC-001729 (AAV-3), NC-001829 (AAV-4), U89790 (AAV-4), NC-006152 (AAV-5), AF513851 (AAV-7), AF513852 (AAV-8), and NC-006261 (AAV-8); the disclosures of which are incorporated by reference herein. See also, e.g., Srivistava et al., 1983, J. Virology 45:555; Chiorini et al., 1998, J. Virology 71:6823; Chiorini et al., 1999, J. Virology 73:1309; Bantel-Schaal et al., 1999, J. Virology 73:939; Xiao et al., 1999, J. Virology 73:3994; Muramatsu et al., 1996, Virology 221:208; Shade et al., 1986, J. Virol. 58:921; Gao et al., 2002, Proc. Nat. Acad. Sci. USA 99: 11854; Moris et al., 2004, Virology 33:375-383; international patent publications WO 00/28061, WO 99/61601, WO 98/11244; WO 2013/063379; WO 2014/194132; WO 2015/121501, and U.S. Pat. Nos. 6,156,303 and 7,906,111.

An "rAAV vector" as used herein refers to an AAV vector comprising a polynucleotide sequence not of AAV origin (i.e., a polynucleotide heterologous to AAV), typically a sequence of interest for the genetic transformation of a cell. In some embodiments, the heterologous polynucleotide may be flanked by at least one, and sometimes by two, AAV inverted terminal repeat sequences (ITRs). The term rAAV vector encompasses both rAAV vector particles and rAAV vector plasmids. A rAAV vector may either be single-stranded (ssAAV) or self-complementary (scAAV). An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as a "rAAV vector particle" or simply an "rAAV vector". Thus, production of rAAV particle necessarily includes production of rAAV vector, as such a vector is contained within an rAAV particle.

"Recombinant," as used herein means that the vector, polynucleotide, polypeptide or cell is the product of various combinations of cloning, restriction or ligation steps (e.g. relating to a polynucleotide or polypeptide comprised therein), and/or other procedures that result in a construct that is distinct from a product found in nature. A recombinant virus or vector is a viral particle comprising a recombinant polynucleotide. The terms respectively include replicates of the original polynucleotide construct and progeny of the original virus construct.

"AAV Rep" means AAV replication proteins and analogs thereof.

"AAV Cap" means AAV capsid proteins, VP1, VP2 and VP3 and analogs thereof. In wild type AAV virus, three capsid genes vp1, vp2 and vp3 overlap each other. See, Grieger and Samulski, 2005, J. Virol. 79(15):9933-9944. A single P40 promoter allows all three capsid proteins to be expressed at a ratio of about 1:1:10, vp1, vp2, vp3, respectively, which complement with rAAV production. For the production of recombinant AAV vectors, desired ratio of VP1:VP2:VP3 is in the range of about 1:1:1 to about 1:1:100, preferably in the range of about 1:1:2 to about 1:1:50, more preferably in the range of about 1:1:5 to about 1:1:20. Although the desired ratio of VP1:VP2 is 1:1, the ratio range of VP1:VP2 could vary from 1:50 to 50:1.

A comprehensive list and alignment of amino acid sequences of capsids of known AAV serotypes is provided by Marsic et al., 2014, Molecular Therapy 22(11):1900-1909, especially at supplementary FIG. 1.

For illustrative purposes only, wild type AAV2 comprises a small (20-25 nm) icosahedral virus capsid of AAV composed of three proteins (VP1, VP2, and VP3; a total of 60 capsid proteins compose the AAV capsid) with overlapping sequences. The proteins VP1 (735 aa; Genbank Accession No. AAC03780), VP2 (598 aa; Genbank Accession No. AAC03778) and VP3 (533 aa; Genbank Accession No. AAC03779) exist in a 1:1:10 ratio in the capsid. That is, for AAVs, VP1 is the full length protein and VP2 and VP3 are progressively shorter versions of VP1, with increasing truncation of the N-terminus relative to VP1.

"AAV TR" means a palindromic terminal repeat sequence at or near the ends of the AAV genome, comprising mostly complementary, symmetrically arranged sequences, and includes analogs of native AAV TRs and analogs thereof.

"Cis-motifs" includes conserved sequences such as found at or close to the termini of the genomic sequence and recognized for initiation of replication; cryptic promoters or sequences at internal positions likely used for transcription initiation, splicing or termination.

"Treating" or "treatment" means reversing, alleviating, or inhibiting the progress of the disorder or condition to which such term applies, or one or more symptoms of such disorder or condition.

"Therapeutically effective amount" means a minimal amount of active agent which is necessary to impart therapeutic benefit to a subject. For example, a "therapeutically effective amount" to a patient is such an amount which induces, ameliorates, stabilizes, slows down the progression or otherwise causes an improvement in the pathological symptoms, disease progression or physiological conditions associated with or resistance to succumbing to a disorder.

"Gene" means a polynucleotide containing at least one open reading frame that is capable of encoding a particular polypeptide or protein after being transcribed and translated.

"Coding sequence" means a sequence which encodes a particular protein" or "encoding nucleic acid", denotes a nucleic acid sequence which is transcribed (in the case of DNA) and translated (in the case of mRNA) into a polypeptide in vitro or in vivo when placed under the control of (operably linked to) appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

"Chimeric" means, with respect to a viral capsid or particle, that the capsid or particle includes sequences from different parvoviruses, preferably different AAV serotypes, as described in Rabinowitz et al., U.S. Pat. No. 6,491,907, the disclosure of which is incorporated in its entirety herein by reference. See also Rabinowitz et al., 2004, J. Virol. 78(9):4421-4432. A particularly preferred chimeric viral capsid is the AAV2.5 capsid, which has the sequence of the AAV2 capsid with the following mutations: 263 Q to A; 265 insertion T; 705 N to A; 708 V to A; and 716 T to N. wherein the nucleotide sequence encoding such capsid is defined as SEQ ID NO: 15 as described in WO 2006/066066. Other preferred chimeric AAVs include, but are not limited to, AAV2i8 described in WO 2010/093784, AAV2G9 and AAV8G9 described in WO 2014/144229, and AAV9.45 (Pulicherla et al., 2011, Molecular Therapy 19(6):1070-1078).

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences there between.

"Polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

"Transduction" of a cell by a virus means that there is transfer of a nucleic acid from the virus particle to the cell.

"Modified FXN gene" means a modified nucleic acid encoding FXN (e.g., the amino acid sequence of SEQ ID NO:1) with at least one modification compared with a wild type nucleic acid encoding FXN (e.g., SEQ ID NO:2), wherein the modification includes, but is not limited to, increased GC content, decreased GC content or a FXN gene with a reduced CpG content. Preferably, the modified FXN gene exhibits improved protein expression, e.g., the protein encoded thereby is expressed at a detectably greater level in a cell compared with the level of expression of the protein provided by the wild type gene in an otherwise identical cell.

"Transfection" of a cell means that genetic material is introduced into a cell for the purpose of genetically modifying the cell. Transfection can be accomplished by a variety of means known in the art, such as calcium phosphate, polyethyleneimine, electroporation, and the like.

"Polypeptide" encompasses both peptides and proteins, unless indicated otherwise.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

The terms "host cell," "host cell line," and "host cell culture" are used interchangeably and refer to cells into which exogenous nucleic acid has been introduced, including the progeny of such cells. Host cells include "transformants, "transformed cells," and "transduced cells," which include the primary transformed cell and progeny derived therefrom without regard to the number of passages.

"Transgene" is used to mean any heterologous nucleotide sequence incorporated in a vector, including a viral vector, for delivery to and including expression in a target cell (also referred to herein as a "host cell"), and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

"Vector," means a recombinant plasmid or virus that comprises a polynucleotide to be delivered into a host cell, either in vitro or in vivo.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

"Recombinant viral vector" means a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs).

"Homologous" used in reference to peptides, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modification are included, such as minor variations, deletions, substitutions or derivatizations of the amino acid sequence of the sequences disclosed herein, so long as the peptide has substantially the same activity or function as the unmodified peptides. Derivatives of an amino acid may include but not limited to trifluoroleucine, hexafluoroleucine, 5,5,5-trifluoroisoleucine, 4,4,4-trifluorovaline, p-fluorophenylaline, o-fluorotyrosine, m-fluorotyrosine, 2,3-difluorotyrosine, 4-fluorohistidine, 2-fluorohistidine, 2,4-difluorohistidine, fluoroproline, difluoroproline, 4-hydroxyproline, selenomethionine, telluromethionine, selenocysteine, selenatryptophans, 4-aminotryptophan, 5-aminotryptophan, 5-hydroxytryptophan, 7-azatryptophan, 4-fluorotryptophan, 5-fluorotryptophan, 6-fluorotryptophan, homoallylglycine, homopropargylglycine, 2-butynylglycine, cis-crotylglycine, allylglycine, dehydroleucine, dehydroproline, 2-amino-3-methyl-4-pentenoic acid, azidohomoalanine, asidoalanine, azidonorleucine, p-ethynylphenylalanine, p-azidophenylalanine, p-bromophenylalanine, p-acetylphenylalanine and benzofuranyl-alanine. Notably, a modified peptide will retain activity or function associated with the unmodified peptide, the modified peptide will generally have an amino acid sequence "substantially homologous" with the amino acid sequence of the unmodified sequence.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Of interest is the BestFit program using the local homology algorithm of Smith and Waterman (1981, Advances in Applied Mathematics 2: 482-489) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc.

Percent sequence identity is calculated by FastDB based upon the following parameters: Mismatch Penalty: 1.00; Gap Penalty: 1.00; Gap Size Penalty: 0.33; and Joining Penalty: 30.0.

The present invention provides for modified FXN genes. The invention also provides nucleic acid constructs, such as vectors, which include as part of their sequence a modified FXN gene, e.g., GC content optimized FXN gene sequence comprising a greater or lesser amount of GC nucleotides compared with the wild type FXN gene sequence and/or a FXN gene sequence having reduced levels of CpG dinucleotides compared with the level of CpG dinucleotides present in the wild type FXN gene. For example, the invention includes plasmids and/or other vectors that include the modified FXN sequence along with other elements, such as regulatory elements. Further, the invention provides packaged gene delivery vehicle, such as a viral capsid, including the modified FXN sequence. The invention also includes methods of delivery and, preferably, expressing the modified FXN gene by delivering the modified sequence into a cell along with elements required to promote expression in the cell. The invention also provides gene therapy methods in which the modified FXN gene sequence is administered to a subject, e.g., as a component of a vector and/or packaged as a component of a viral gene delivery vehicle. Treatment may, for example, be effected to increase levels of frataxin in a subject and treat a frataxin deficiency in the subject. Each of these aspects of the invention is discussed further in the ensuing sections.

Modified Nucleic Acid for Expression of Frataxin

The invention provides a modified nucleotide sequence encoding frataxin. The modified nucleotide sequence includes the wild type or native FXN gene sequence including one or more modifications.

In one aspect, the modified nucleic acid sequence provides a detectably greater level of expression of frataxin in a cell compared with the expression of frataxin from the wild type nucleic acid sequence of SEQ ID NO:2 in an otherwise identical cell. This can be referred to as an "expression optimized" or "enhanced expression" nucleic acid, or simply, as a "modified nucleic acid."

"Optimized" or "codon-optimized" as referred to interchangeably herein, refers to a coding sequence that has been optimized relative to a wild type coding sequence (e.g., a coding sequence for frataxin) to increase expression of the coding sequence, e.g., by minimizing usage of rare codons, decreasing the number of CpG dinucleotides, removing cryptic splice donor or acceptor sites, removing Kozak sequences, removing ribosomal entry sites, and the like.

Examples of modifications include elimination of one or more cis-acting motifs and introduction of one or more Kozak sequences. In one embodiment, one or more cis-acting motifs are eliminated and one or more Kozak sequences are introduced.

Examples of cis acting motifs that may be eliminated include internal TATA-boxes; chi-sites; ribosomal entry sites; ARE, INS, and/or CRS sequence elements; repeat sequences and/or RNA secondary structures; (cryptic) splice donor and/or acceptor sites, branch points; and SalI.

In one embodiment, the GC content (e.g., the number of G and C nucleotides present in a nucleic acid sequence) is enhanced relative to wild-type FXN gene sequence of SEQ ID NO:2. The GC content is preferably at least 5%, more preferably, at least 6%, yet more preferably, at least 7%, even more preferably, at least 8%, more preferably, at least 9%, even more preferably, at least 10%, yet more preferably, at least 12%, even more preferably, at least 14%, yet more preferably, at least 15%, more preferably, at least 17%, even more preferably, at least 20%, even further preferably, at least 30%, yet more preferably, at least 40%, more preferably, at least 50%, even more preferably, at least 60%, and most preferably, at least 70% greater than the wild type gene (SEQ ID NO:2).

In another embodiment, the GC content is expressed as a percentage of G (guanine) and C (cytosine) nucleotides in the sequence. That is, the GC content of the wild type nucleic acid encoding frataxin (SEQ ID NO:1) is about 55% whereas the GC content of representative modified FXN genes of the invention ranges from about 57% for IDT-3 (SEQ ID NO:8), 57% for Genescript (SEQ ID NO:6); 61% for GeneArt (SEQ ID NO:5), and 69% for JCAT (SEQ ID NO:4). Thus, the modified nucleic acid of the invention comprises a of at least 57%, more preferably, a GC content of at least 61%, even more preferably, a GC content of least 69%, compared with the GC content of about 55% of the wild type nucleic acid sequence encoding frataxin as set forth in SEQ ID NO:2.

In one embodiment, the GC content of a modified nucleic acid of the invention is greater than the GC content of the wild type nucleic acid encoding frataxin comprising the nucleic acid sequence of SEQ ID NO:2. One skilled in the art would appreciate, knowing the degeneracy of the nucleic acid code, that irrespective of the sequence of the nucleic acid encoding the protein, the amino acid sequence of frataxin expressed therefrom is, preferably, the amino acid sequence of SEQ ID NO:1.

In one embodiment, the GC content of a modified nucleic acid encoding FXN of the invention is about the same, i.e., 55%, as the GC content of wild type FNX gene (SEQ ID NO:2).

Additionally, the codon adaptation index of the modified nucleic acid encoding frataxin (i.e., the modified FXN gene) is preferably at least 0.74, preferably, at least 0.76, even more preferably, at least 0.77, yet more preferably, at least 0.80, preferably, at least 0.85, more preferably, at least 0.86, yet more preferably, at least 0.87, even more preferably, at least 0.90, yet more preferably, at least 0.95, and most preferably, at least 0.98.

In another embodiment the modified FXN sequence has a reduced level of CpG dinucleotides that being a reduction of about 10%, 20%, 30%, 50% or more, compared with the wild type nucleic acid sequence encoding FXN (e.g., SEQ ID NO:2).

It is known that methylation of CpG dinucleotides plays an important role in the regulation of gene expression in eukaryotes. Specifically, methylation of CpG dinucleotides in eukaryotes essentially serves to silence gene expression through interfering with the transcriptional machinery. As such, because of the gene silencing evoked by methylation of CpG motifs, the nucleic acids and vectors of the invention having a reduced number of CpG dinucleotides will provide for high and long lasting transgene expression level.

In one embodiment, the modified FXN gene comprises fewer potential CpG island regions than wild type FXN gene, i.e., 128. Preferably, the modified FXN gene comprises about 124 potential CpG island regions, more preferably, about 123, even more preferably, about 117, and more preferably, about 114 potential CpG island regions.

The modified FXN gene sequence may also include flanking restriction sites to facilitate subcloning into expression vector. Many such restriction sites are well known in the art, and include, but are not limited to, those shown in FIGS. 2A-2F, and FIG. 3 (plasmid map of scAAV plasmid vector pTRs-KS-CBh-EGFP-BGH) and Table 8 (SEQ ID NOs:19-23), such as, AgeI, AvrII, SpeI and MluI.

The invention also includes fragments of any one of sequences SEQ ID NOs:3 through 9 which encode a functionally active fragment frataxin. "Functionally active" or "functional frataxin" indicates that the fragment provides the same or similar biological activity as a full-length frataxin. That is, the fragment provides the same activity including, but not limited to, correcting primary Fe-S cluster deficit, decreasing mitochondrial iron accumulation (Puccio et al., 2001, Nature Genetics 27:181-186; Seznec et al., 2004, Human Mol. Genet. 13:1017-1024) and other deficiencies as discussed in Perdomini et al., 2014, Nature Med. 20(5):542-547. The biological activity of FXN, or a functional fragment thereof, also encompasses reversing or preventing the cardiac phenotype associated with FRDA as demonstrated elsewhere herein in Mck mice.

The invention includes a nucleic acid vector including the modified FXN gene sequence and various regulatory or control elements. The precise nature of regulatory elements useful for gene expression will vary from organism to organism and from cell type to cell type. In general, they include a promoter which directs the initiation of RNA transcription in the cell of interest. The promoter may be constitutive or regulated. Constitutive promoters are those which cause an operably linked gene to be expressed essentially at all times. Regulated promoters are those which can be activated or deactivated. Regulated promoters include inducible promoters, which are usually "off" but which may be induced to turn "on," and "repressible" promoters, which are usually "on" but may be turned "off." Many different regulators are known, including temperature, hormones, cytokines, heavy metals and regulatory proteins. The distinctions are not absolute; a constitutive promoter may often be regulated to some degree. In some cases an endogenous pathway may be utilized to provide regulation of the transgene expression, e.g., using a promoter that is naturally downregulated when the pathological condition improves.

Examples of suitable promoters include adenoviral promoters, such as the adenoviral major late promoter; heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the α-1-antitrypsin promoter; the hepatitis B surface antigen promoter; the transferrin promoter; the apolipoprotein A-1 promoter; chicken beta-actin CBA) promoter, the CBh promoter (SEQ ID NO:25), and the CAG promoter (cytomegalovirus early enhancer element and the promoter, the first exon, and the first intron of chicken beta-actin gene and the splice acceptor of the rabbit beta-globin gene) (Alexopoulou et al., 2008, BioMed. Central Cell Biol. 9:2), and human FXN promoters. The promoter may be a tissue-specific promoter, such as the mouse albumin promoter, which is active in liver cells as well as the transthyretin promoter (TTR).

In another aspect, the modified nucleic acid encoding FXN further comprises an enhancer to increase expression of the FXN protein. Many enhancers are known in the art, including, but not limited to, the cytomegalovirus major immediate-early enhancer. More specifically, the CMV MIE promoter comprises three regions: the modulator, the unique region and the enhancer (Isomura and Stinski, 2003, J. Virol. 77(6):3602-3614). The CMV enhancer region can be combined with other promoters, or a portion thereof, to form hybrid promoters to further increase expression of a nucleic acid operably linked thereto. For example, a chicken beta-actin (CBA) promoter, or a portion thereof, can be combined with the CMV promoter/enhancer, or a portion thereof, to make a version of CBA termed the "CBh" promoter, which stands for chicken beta-actin hybrid promoter, as described in Gray et al. (2011, Human Gene Therapy 22:1143-1153).

Further, the control elements can include a collagen stabilization sequence (CSS), a stop codon, a termination sequence, and a poly-adenylation signal sequence, such as, but not limited to a bovine growth hormone poly A signal sequence (bGHpolyA), to drive efficient addition of a poly-adenosine "tail" at the 3' end of a eukaryotic mRNA (see, e.g., Goodwin and Rottman, 1992, J. Biol. Chem. 267(23): 16330-16334).

Non-Viral Vectors

In a particular embodiment, the vector used according to the invention is a non-viral vector. Typically, the non-viral vector may be a plasmid which includes nucleic acid sequences reciting the modified FXN gene, or variants thereof.

Packaged Modified FXN Sequence

The modified FXN gene sequence may also be provided as a component of a packaged viral vector. In general, packaged viral vectors include a viral vector packaged in a capsid. Viral vectors and viral capsids are discussed in the ensuing sections. The nucleic acid packaged in the rAAV vector can be single-stranded (ss), self-complementary (sc), or double-stranded (ds).

Viral Vector

Typically, viral vectors carrying transgenes are assembled from polynucleotides encoding the transgene, suitable regulatory elements and elements necessary for production of viral proteins which mediate cell transduction. Examples of a viral vector include but are not limited to adenoviral, retroviral, lentiviral, herpesvirus and adeno-associated virus (AAV) vectors.

The viral vector component of the packaged viral vectors produced according to the methods of the invention includes at least one transgene, e.g., a modified FXN gene sequence and associated expression control sequences for controlling expression of the modified FXN gene sequence.

In a preferred embodiment, the viral vector includes a portion of a parvovirus genome, such as an AAV genome with rep and cap deleted and/or replaced by the modified FXN gene sequence and its associated expression control sequences. The modified FXN gene sequence is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins. Other regulatory sequences suitable for use in facilitating tissue-specific expression of the modified FXN gene sequence in the target cell may also be included.

One skilled in the art would appreciate that an AAV vector comprising a transgene and lacking virus proteins needed for viral replication (e.g., cap and rep), cannot replicate since such proteins are necessary for virus replication and packaging. Further, AAV is a Dependovirus in that it cannot replicate in a cell without co-infection of the cell by a helper virus. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to E1 and E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e., self complementary as described in WO 2001/92551).

One skilled in the art would appreciate that a rAAV vector can further include a "steer" or "filler" sequence (filler/stuffer) where the nucleic acid comprising the transgene is less than the approximately 4.1 to 4.9 kb size for optimal packaging of the nucleic acid into the AAV capsid. See, Grieger and Samulski, 2005, J. Virol. 79(15):9933-9944. That is, AAV vectors typically accept inserts of DNA having a defined size range which is generally about 4 kb to about 5.2 kb, or slightly more. Thus, for shorter sequences, inclusion of a filler/stuffer in the insert fragment in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. In particular embodiments of a rAAV vector, a heterologous polynucleotide sequence has a length less than 4.7 Kb and the filler/stuffer polynucleotide sequence has a length that when combined (e.g., inserted into a vector) with the heterologous polynucleotide sequence has a total length between about 3.0-5.5 Kb, or between about 4.0-5.0 Kb, or between about 4.3-4.8 Kb.

An intron can also function as a filler/stuffer polynucleotide sequence in order to achieve a length for AAV vector packaging into a virus particle. Introns and intron fragments that function as a filler/stuffer polynucleotide sequence also can enhance expression. For example, inclusion of an intron element may enhance expression compared with expression in the absence of the intron element (Kurachi et al., 1995, J. Biol. Chem. 270(10):5276-5281). Furthermore, filler/stuffer polynucleotide sequences are well known in the art and include, but are not limited to, those described in WO 2014/144486.

Viral Capsid

The viral capsid component of the packaged viral vectors may be a parvovirus capsid. AAV Cap and chimeric capsids are preferred. Examples of suitable parvovirus viral capsid components are capsid components from the family Parvoviridae, such as an autonomous parvovirus or a Dependovirus. For example, the viral capsid may be an AAV capsid (e.g., AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAVrh10, AAVrh74, RHM4-1 (SEQ ID NO:5 of WO 2015/013313), AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4$^{th}$ ed., Lippincott-Raven Publishers). Capsids may be derived from a number of AAV serotypes disclosed in U.S. Pat. No. 7,906,111; Gao et al., 2004, J. Virol. 78:6381; Moris et al., 2004, Virol. 33:375; WO 2013/063379; WO 2014/194132; and include true type AAV (AAV-TT) variants disclosed in WO 2015/121501, and RHM4-1, RHM15-1 through RHM15-6, and variants thereof, disclosed in WO 2015/013313, and one skilled in the art would know there are likely other variants not yet identified that perform the same or similar function, or may include components from two or more AAV capsids. A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences of AAV Caps from two or more viruses, preferably two or more AAVs, as described in Rabinowitz et al., U.S. Pat. No. 6,491,907, the entire disclosure of which is incorporated herein by reference. For example, the chimeric virus capsid can include an AAV1 Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, in a preferred embodiment, the Vp3 subunit of the AAV capsid can be replaced by the Vp2 subunit of B19.

Another embodiment includes chimeric viral strains synthesized include the combination of AAV backbones from AAV2, AAV3, AAV6, AAV8, etc., with a galactose (Gal) binding footprint from AAV9. Adeno-associated viruses (AAVs) are helper-dependent parvoviruses that exploit heparan sulfate (HS), galactose (Gal), or sialic acids (Sia) as primary receptors for cell surface binding. For instance, AAV serotypes 2 and 3b utilize HS. AAV1, 4, and 5 bind Sia with different linkage specificities, AAV serotype 6, which recognizes both Sia and HS, whereas AAV9 exploits Gal for host cell attachment. Specifically, the galactose (Gal) binding footprint from AAV9 was grafted onto the heparin sulfate-binding AAV serotype 2 and just grafting of orthogonal glycan binding footprints improves transduction efficiency. A new dual glycan-binding strain (AAV2G9) and a chimeric, muscle-tropic strain (AAV2i8G9) were generated by incorporating the Gal binding footprint from AAV9 into the AAV2 VP3 backbone or the chimeric AAV2i8 capsid template using structural alignment and site-directed mutagenesis. In vitro binding and transduction assays confirmed the exploitation of both HS and Gal receptors by AAV2G9 for cell entry. Subsequent in vivo characterization of the kinetics of transgene expression and vector genome biodistribution profiles indicate fast, sustained, and enhanced transgene expression by this rationally engineered chimeric AAV strain. A similar, improved transduction profile was observed with the liver-detargeted, muscle-specific AAV2i8G9 chimera (Shen, et al., 2013, J. Biol. Chem. 288(4):28814-28823). Such new grafting combination is fully described in WO2014/144229 the contents of which are incorporated by reference herein. Additional liver de-targeted AAVs, such as AAV9.45, are described in Pulicherla et al., 2011, Molecular Therapy 19(6):1070-1078, the contents of which are incorporated by reference as if set forth in their entirety herein.

In yet another embodiment the present invention provides for the use of ancestral AAV vectors for use in therapeutic in vivo gene therapy. Specifically, in silico-derived sequences were synthesized de novo and characterized for biological activities. This effort led to the generation of nine functional putative ancestral AAVs and the identification of Anc80, the predicted ancestor of AAV serotypes 1, 2, 8 and 9 (Zinn et al., 2015, Cell Reports 12:1056-1068). Predicting and synthesis of such ancestral sequences in addition to assembling into a virus particle may be accomplished by using the methods described in WO 2015/054653, the contents of which are incorporated by reference herein. Notably, the use of the virus particles assembled from ancestral viral sequences exhibit reduced susceptibility to pre-existing immunity in current day human population than do contemporary viruses or portions thereof.

Production of Packaged Viral Vector

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than $1\times10^5$ vector genome containing particles (vg)/cell or greater than $1\times10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified FXN gene and CBh promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>$1\times10^{13}$ vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous timepoints post-transfection.

Viral Vector Functions

The packaging cells of the invention include viral vector functions, along with packaging and vector functions. The viral vector functions typically include a portion of a parvovirus genome, such as an AAV genome, with rep and cap deleted and replaced by the modified FXN sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

"Duplexed vectors" may interchangeably be referred to herein as "dimeric" or "self-complementary" vectors. The duplexed parvovirus particles may, for example, comprise a parvovirus capsid containing a virion DNA (vDNA). The vDNA is self-complementary so that it may form a hairpin structure upon release from the viral capsid. The duplexed vDNA appears to provide to the host cell a double-stranded DNA that may be expressed (i.e., transcribed and, optionally, translated) by the host cell without the need for second-strand synthesis, as required with conventional parvovirus vectors. Duplexed/self-complementary rAAV vectors are well-known in the art and described, e.g., in WO 2001/92551, WO 2015/006743, and many others.

The viral vector functions may suitably be provided as duplexed vector templates, as described in U.S. Pat. No. 7,465,583 to Samulski et al. (the entire disclosure of which is incorporated herein by reference for its teaching regarding duplexed vectors). Duplexed vectors are dimeric self-complementary (sc) polynucleotides (typically, DNA). The duplexed vector genome preferably contains sufficient packaging sequences for encapsidation within the selected parvovirus capsid (e.g., AAV capsid). Those skilled in the art will appreciate that the duplexed vDNA may not exist in a double-stranded form under all conditions, but has the ability to do so under conditions that favor annealing of complementary nucleotide bases. "Duplexed parvovirus particle" encompasses hybrid, chimeric and targeted virus particles. Preferably, the duplexed parvovirus particle has an AAV capsid, which may further be a chimeric or targeted capsid, as described above.

The viral vector functions may suitably be provided as duplexed vector templates, as described in U.S. Pat. No. 7,465,583 to Samulski et al. (the entire disclosure of which is incorporated herein by reference for its teaching regarding duplexed vectors). Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsulated by the virus.

The TR(s) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1 (SEQ ID NO:15), AAV2.5 (SEQ ID NO. 13), AAV6.1 (SEQ ID NO:17), AAV6.3.1 (SEQ ID NO:18), AAV9.45, AAV2i8 (SEQ ID NO:29), AAV2G9, AAV2i8G9, AAV2-TT (SEQ ID NO:31), AAV2-TT-S312N (SEQ ID NO:33), AAV3B-S312N, and AAV-LK03, and other novel capsids as yet unidentified or from non-human primate sources. Capsid components may include components from two or more AAV capsids.

In a more preferred embodiment, one or more of the VP capsid proteins is a chimeric protein, comprising amino acid sequences from two or more viruses, preferably two or more AAVs, as described in Rabinowitz et al., U.S. Pat. No. 6,491,907. A chimeric capsid is described herein as having at least one amino acid residue from one serotype combined with another serotype that is sufficient to modify a) viral yield, b) immune response, c) targeting, d) de-targeting, etc.

Further chimeric proteins can be made by instruction set forth in Li, et al., 2008, Mol. Ther. 16(7):1252-1260, the contents of which are incorporated by reference herein. Specifically, a DNA shuffling-based approach was used for developing cell type-specific vectors through directed evolution. Capsid genomes of adeno-associated virus (AAV) serotypes 1-9 were randomly fragmented and reassembled using PCR to generate a chimeric capsid library. A single infectious clone (chimeric-1829) containing genome fragments from AAV1, 2, 8, and 9 was isolated from an integrin minus hamster melanoma cell line previously shown to have low permissiveness to AAV. Molecular modeling studies suggest that AAV2 contributes to surface loops at the icosahedral threefold axis of symmetry, while AAV1 and 9 contribute to two- and five-fold symmetry interactions, respectively. The C-terminal domain (AAV9) was identified as a critical structural determinant of melanoma tropism through rational mutagenesis. Chimeric-1829 utilizes heparan sulfate as a primary receptor and transduces melanoma cells more efficiently than all serotypes. Application of this technology to alternative cell/tissue types using AAV or other viral capsid sequences is likely to yield a new class of biological nanoparticles as vectors for human gene transfer.

The packaged viral vector generally includes the modified FXN gene sequence and expression control sequences flanked by TR elements, referred to herein as the "transgene" or "transgene expression cassette," sufficient to result in packaging of the vector DNA and subsequent expression of the modified FXN gene sequence in the transduced cell. The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

Packaging Functions

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

Helper Functions

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Packaging Cell

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359.

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provide for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculavirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein. These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA rAAV Purification The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443; U.S. Pat. No. 6,566,118 and WO 98/09657.

Treatment Methods

The modified FXN gene may be used for gene therapy of Friedreich ataxia associated disorders, such as, degenerative neuro-muscular disorders and/or cardiomyopathy associated with Friedreich ataxia. An individual may be in need of gene therapy because, as a result of one or more mutations in the coding sequence of the FXN gene, FXN is expressed inappropriately, e.g., has an incorrect amino acid sequence, or is expressed in the wrong tissues or at the wrong times or is underexpressed. The modified FXN gene of the present invention may be used as gene therapy to enhance production of the protein frataxin and thereby increasing energy production in the mitochondria. See, e.g., U.S. Pat. No. 9,066,966.

The target cells of the vectors of the instant invention are cells capable of expressing frataxin, such as those of the cardiac system of a mammal, neuron cells, muscle cells, and other cells with the proper cellular machinery to process the precursor to yield protein with frataxin activity.

Pharmaceutical Composition

In particular embodiments, the present invention provides a pharmaceutical composition for preventing or treating a disease or condition mediated by or associated with decreased expression of frataxin, e.g., Friedreich ataxia. The composition comprises a therapeutically effective amount of a vector which comprises a modified FXN gene which can increase the level of expression of FXN in a call. The composition comprises the vector comprising the modified, e.g., optimized, nucleic acid encoding FXN wherein the composition further comprises a pharmaceutically-acceptable carrier and/or other medicinal agents, pharmaceutical agents, carriers, adjuvants, diluents, etc. For injection, the carrier will typically be a liquid. As an injection medium, it is preferred to use water that contains the additives usual for injection solutions, such as stabilizing agents, salts or saline, and/or buffers.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material.

A pharmaceutical composition may be used, for example, in transfection of a cell ex vivo or in administering a viral vector or cell directly to a subject.

Recombinant virus vectors comprising the modified FXN gene are preferably administered to the cell in a biologically-effective amount. If the virus vector is administered to a cell in vivo (e.g., the virus is administered to a subject as described below), a biologically-effective amount of the virus vector is an amount that is sufficient to result in transduction and expression of the transgene in a target cell.

In one embodiment, the invention includes a method of increasing the level of frataxin in a cell by administering to the cell a nucleic acid, either alone or in a vector (including a plasmid, a virus, a nanoparticle, a liposome, or any known method for providing a nucleic acid to a cell) comprising a modified nucleic acid encoding frataxin. The method comprises a method wherein the level of mRNA encoding frataxin and/or the level of frataxin protein expressed is detectably greater than the level of frataxin (mRNA and/or protein) in an otherwise identical cell that is not administered the nucleic acid. The skilled artisan would understand that the cell can be cultured or grown in vitro or can be present in an organism (i.e., in vivo). Further, the cell may express endogenous frataxin such that the level of frataxin in the cell can be increased, and/or the cell can express an endogenous frataxin that is a mutant or variant of wild type frataxin, e.g., frataxin having the sequence of SEQ ID NO:2, especially as there may be more than one wild type alleles for human frataxin. Thus, the level of frataxin is increased compared with the level of frataxin compared with the level of frataxin expressed in an otherwise identical but untreated cell.

A further aspect of the invention is a method of treating subjects in vivo with the vector containing modified genes. Administration of the vector to a human subject or an animal in need thereof can be by any means known in the art for administering virus vectors.

The vector can be administered in addition, and as an adjunct to, the standard of care. That is, the vector can be co-administered with another therapeutic agent or compound, either simultaneously, contemporaneously, or at a determined dosing interval as would be determined by one skilled in the art using routine methods.

In one aspect, the rAAV of the invention can be co-administered with empty capsids (i.e., a virus capsid that does not contain a nucleic acid molecule) comprising the same, or a different, capsid protein as the rAAV-FXN vector. This is because one skilled in the art would understand that co-administration of empty capsids may decrease an immune response, e.g., a neutralizing response, the rAAV of the invention. That is, the empty capsid may serve as a decoy allowing the rAAV-FXN vector to avoid a neutralizing antibody (Nab) immune response as discussed in, e.g., WO 2015/013313.

Exemplary modes of administration systemic administration, including, but not limited to, intravenous, subcutaneous, intradermal, intramuscular, and intraarticular administration, and the like, as well as direct tissue or organ injection.

In one embodiment, the vector is administered systemically. One skilled in the art would appreciate that systemic administration can deliver the therapeutic gene encoding FXN to all tissues, including all muscles, affected by the reduced level of FXN therein.

Nonetheless, the skilled artisan would appreciate that the vector can be delivered directly to areas affected by the FXN deficiency, i.e., the brain and the heart.

Accordingly, in other preferred embodiments, the inventive vector comprising the modified FXN gene is administered by direct injection into cardiac or central nervous system (CNS) tissue.

In one embodiment, modified nucleic acid encoding FNX, the vector, or composition comprising the vector, is delivered intracranially including, intrathecal, intraneural, intracerebral, intra-ventricular administration.

In one embodiment, modified nucleic acid encoding FNX, the vector, or composition comprising the vector, is delivered to the heart by direct administration into the myocardium by epicardiac injection followed by minithoracotomy, by intracoronary injection, by endomyocardic injection or by another type of injection useful in the heart.

Additional routes of administration may also comprise local application of the vector under direct visualization, e.g., superficial cortical application, or other nonstereotactic application. The vector may also be delivered, for example, intrathecally, into the ventricles or by intravenous injection.

The target cells of the vectors of the present invention are cells of the myocardium of a subject afflicted with a cardiomyopathy associated with Friedreich ataxia. Preferably the subject is a human being, adult or child. However, veterinary applications are also contemplated.

The target cells of the vectors of the present invention also include cells of the CNS, preferably neurons. Delivery to the brain to treat neurodegenerative aspects of Friedreich ataxia may be by intrathecal administration.

In one aspect, modified nucleic acid encoding FNX, the vector, or composition comprising the vector, is delivery systemically, e.g., intravenously, to treat the FA associated cardiomyopathy and/or the neurodegenerative aspect of the disease.

In another embodiment, the vector is administered by at least two routes. That is, the vector can be administered systemically and also directly into the brain and/or heart, or any combination thereof.

If performed via at least two routes, the administration of the vector can be, but need not be, simultaneous or contemporaneous. Instead, the administrations via different routes can be performed separately with an interval of time between each administration. Appropriate dosing regimens are routinely determined by those skilled in the art to achieve maximum therapeutic benefit for each individual patient.

In one aspect, the invention includes at least one modified nucleic acid encoding frataxin of the invention, including, but not limited to, the nucleic acid in a vector or a pharmaceutical composition, for use in increasing the level of frataxin in a subject.

In one aspect, the invention includes at least one modified nucleic acid, rAAV vector comprising the nucleic acid, and a pharmaceutical composition comprising either the nucleic acid or the vector, for use in treating Friedreich ataxia in a subject.

The use encompasses administering the modified nucleic acid, or vector comprising the same, in addition to and/or concurrent with, the standard of care for FRDA as known in the art.

Injectables can be prepared in conventional forms, either as liquid solutions or suspensions, solid forms suitable for solution or suspension in liquid prior to injection, or as emulsions.

Dosages of the virus vector with the modified FXN gene will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units/kg body weight.

The modified FXN gene may be administered as components of a DNA molecule having regulatory elements appropriate for expression in the target cells. The modified FXN gene may be administered as components of viral plasmids, such as rAAV vectors. Viral particles may be administered as viral particles alone, whether as an in vivo direct delivery to the portal vasculature or as an ex vivo treatment comprising administering the vector viral particles in vitro to cells from the animal receiving treatment followed by introduction of the transduced cells back into the donor.

Equivalents

The foregoing written specification is considered to be sufficient to enable one skilled in the art to practice the disclosure. The foregoing description and Examples detail certain exemplary embodiments of the disclosure. It will be appreciated, however, that no matter how detailed the foregoing may appear in text, the disclosure may be practiced in many ways and the disclosure should be construed in accordance with the appended claims and any equivalents thereof.

All references cited herein, including patents, patent applications, papers, text books, and the like, and the references cited therein, to the extent that they are not already, are hereby incorporated herein by reference in their entirety.

Exemplary Embodiments

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: Generation of a Self-complimentary rAAV-FXN Construct

Materials and Methods

Vector Construction

Figure 3:
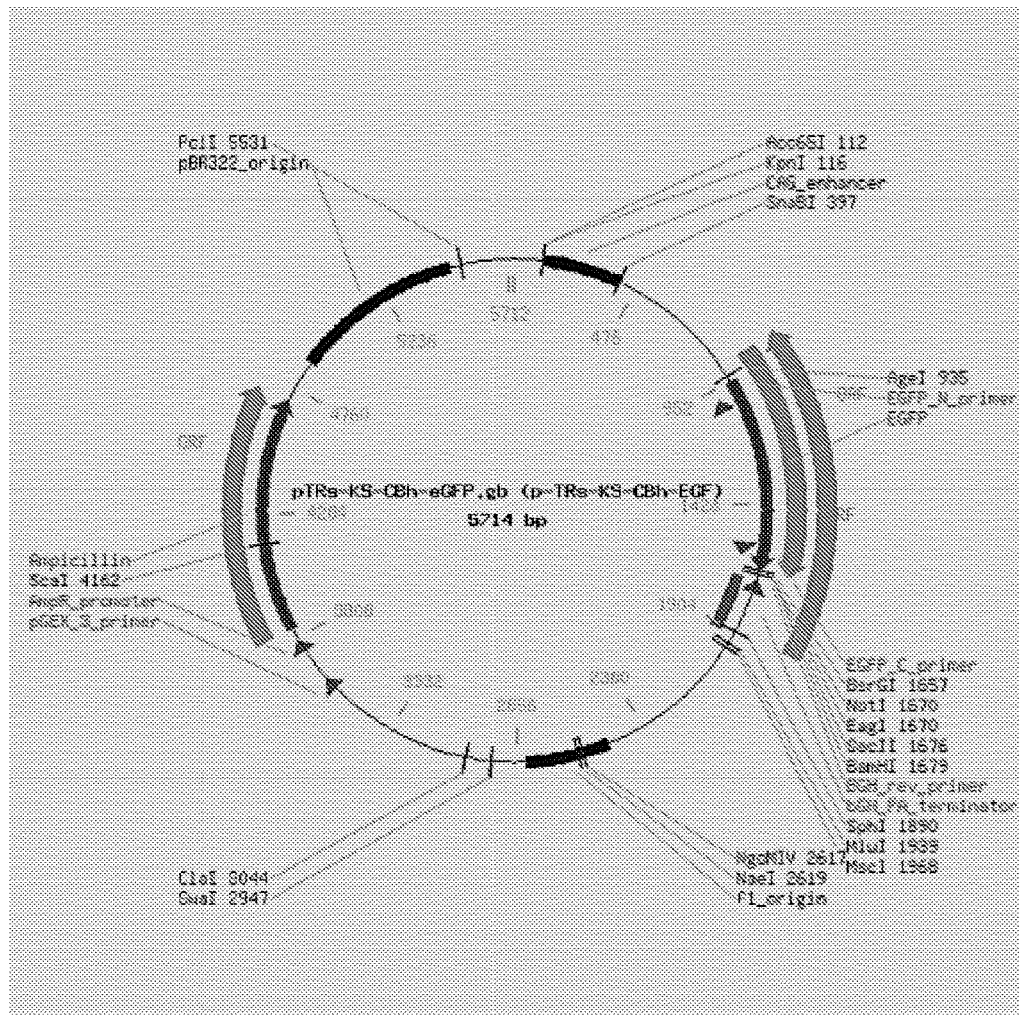
FIG. 3 shows a vector (plasmid) map for the pTRs-KS-CBh-eGFP cloning construct depicting the various restriction (cut) sites and elements of the vector including the CBh promoter upstream from the AgeI cut site.

The pTRs-KS-CBh-EGFP-bGHpolyA construct (shown diagrammatically in FIG. 3) encoding a self-complementary AAV genome was used as the backbone of the transgene expression construct (Gray et al., 2011, Human Gene Therapy 22:1143-1153). Two codon optimized FXN gene inserts were ordered from GenScript in pUC57, i.e., Genscript and Genscript (low CpG), and used to replace the EGFP in the backbone vector. The Genscript (SEQ ID NO:6) and Genscript (low CpG) (SEQ ID NO:7) modified FXN genes were each operably linked to the CBh promoter as illustrated in FIG. 3. The GenScript FXN (SEQ ID NO: 6 and 7) constructs included an N-terminal AgeI site, a collagen stability sequence (CSS) (5'-CCCAGCCCACTTTTC-CCCAA-3') downstream of the FXN stop codon, a bovine growth hormone (BGH) polyA sequence downstream of the CSS, and a MluI site downstream of the BGH polyA all as shown in FIGS. 2E (Genscript) and 2F (Genscript (low CpG)). Exemplary inserts for insertion into the pTRs-KS-CBh-FXN-bGHpolyA constructs are shown in FIGS. 2A-2F and are set forth in Table 8. More specifically, wild type frataxin gene (VVT FXN; SEQ ID NO:2) was cloned into pTRs-KS-CBh-WT FXN-bGHpolyA (FIG. 2A); an IDT1 modified FXN gene (SEQ ID NO:11) was cloned into pTRs-KS-CBh-IDT1-bGHpolyA (FIG. 2B); a nucleic acid encoding IDT3 low expresser modified FXN gene (SEQ ID NO:8) was cloned into pTRs-KS-CBh-IDT3-bGHpolyA (FIG. 2C); an IDT4 modified FXN gene (SEQ ID NO:12) was cloned into pTRs-KS-CBh-IDT4-bGHpolyA (FIG. 2D); a Genscript (control) modified FXN gene (SEQ ID NO:6) was cloned into pTRs-KS-CBh-Genescript-bGHpolyA (FIG. 2E); and a Genscript (low CpG) modified FXN gene (SEQ ID NO:7) was cloned into pTRs-KS-CBh-Genescript (low CpG)-bGHpolyA (FIG. 2F). Each insert encoding a FXN gene was cloned into the vector and the gene was flanked by an AgeI site on the 5' side and by an AvrII cut site on the 3' side, followed by a CSS sequence after the AvrII site, a SpeI cut site after the CSS, a bGHpolyA signal sequence after the SpeI cut site, and a MluI cut site after the polyA signal sequence.

The backbone pTRs-KS-CBh-EGFP-bGHpolyA and the FXN gene constructs were digested with AgeI and MluI (New England Biolabs, R0552S and R0198S, respectively), gel extracted, and ligated using ExTaq polymerase (Clontech, RR001A). The ligation reaction was transformed into SURE cells (Agilent, 200227), placed in SOC recovery media (Cat. No. 15544-034, Invitrogen) for one hour at 37° C., then plated on LB plates with ampicillin (10 mg/ml). Colonies were sequenced and chosen for amplification for virus production. Recombinant AAV (rAAV) vectors with the AAV serotype 2 capsid were produced the UNC Vector Core by a triple-transfection method in human embryonic kidney 293 (HEK293) cells as described (Grieger et al., 2006, Nature Protocols 1:1412-1428). Alternatively, rAAV vector with the serotype 2i8 capsid (amino acid sequence of SEQ ID NO:28) was similarly produced. Highly pure recombinant virus containing self-complementary genomes was recovered by passage through a non-ionic iodixanol gradient followed by ion exchange chromatography. Peak fractions were determined by qPCR then dialyzed in phosphate-buffered saline (PBS) containing 5% d-sorbitol. Viral titers were determined by qPCR (Gray et al., 2010, J. Amer. Soc. Gene Therapy 18:570-578). Following preliminary testing in vitro (below), GenScript (low CpG) was used to generate a construct with an HA tag TACCCATACGATGT-TCCAGATTACGCT inserted prior to the FXN stop codon in pTRs-KS-CBh-Genescript (low CpG)-bGHpolyA.

The University of North Carolina (UNC) Vector Core generated viruses with the FXN-HA construct with rAAV TK serotypes.

In vitro Testing of Sc rAAV-FXN.

HEK293 (ATCC: CRL-1573) and HeLa (ATCC: CCL-2) cells were maintained in Dulbecco's modified Eagle's medium (DMEM, Gibco). Cell growth media was supplemented with 9% fetal bovine serum (FBS, Gibco), 3.4 mM I-glutamine, 100 U/ml penicillin and 100 µg/ml streptomycin (Gibco). Cells were kept in a 5% CO2 atmosphere at 37° C. Dipstick assay: Cells were seeded in 24-well plates so that they reached approximately 60% confluence at 24 hours (h), then mock treated or infected in triplicate with scAAV-FXN (interchangeably referred to herein as "rAAV-FXN" or "rAAV-FXN-HA") at MOI 10,000 (VG/cell). At 60 h post transduction (h p.t.) cells were according to the manufacturer protocol for the Frataxin Protein Quantity Dipstick Assay (Abcam, ab109881). Data was processed using ImageJ.

Western Blotting:

Cells were seeded in 6-well plates so that they reached approximately 60% confluence at 24 h, then mock treated or infected with scAAV-FXN at MOI 10,000 (VG/cell). At 60 h post transduction cells were lysed with cellular lysis buffer (0.0625 M Tris-HCl pH 6.8, 10% glycerol, 2% SDS, 5% 2-mercaptoethanol, 0.02% (w/v) Bromophenol blue). Fifteen (15) µl of HeLa protein lysate was separated by gel electrophoresis on a 15-4% TGX gel and the proteins were electroblotted to a nitrocellulose membrane (NCM). NCMs were blocked using 5% non-fat powdered milk in PBS-T. The anti-frataxin antibody (Abcam, 18A5DB1) was used in PBS-T with 5% milk. A horseradish peroxidase (HRP)-conjugated secondary antibody in PBS-T with 5% milk antibodies was used to detect the presence of anti-frataxin. The WesternBright ECL Western Blotting Detection kit (Advansta, K-12045-D50) was used for detection per manufacturer's instructions.

Figure 1B:
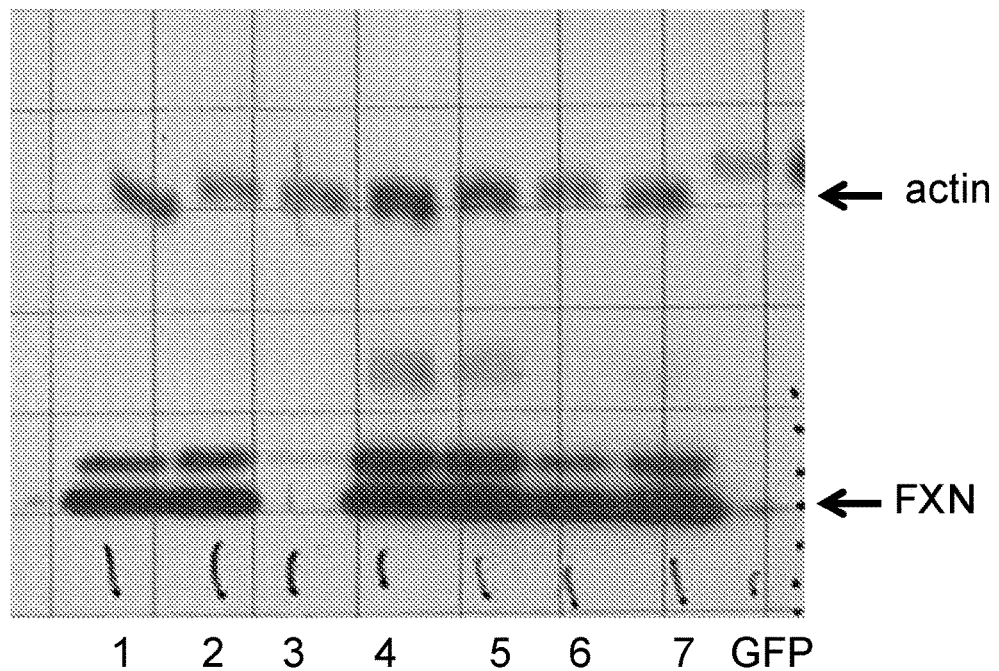

FIG. 1A-1B shows the results for expression of various optimized sequences compared with expression of the unoptimized, i.e., wild type, sequence encoding FXN (SEQ ID NO:1) in HeLa cells. More specifically, both FIGS. 1A and 1B show a photograph of a Western blot showing expression of frataxin (FXN) in HeLa cells transfected with an expression vector comprising an insert encoding frataxin. FIG. 1A shows expression of FXN in HeLa cells in a photograph of a WesternBright blot film exposed for 1 second. FIG. 1B shows a repeat of the experiment shown in FIG. 1A demonstrating expression of FXN in HeLa cells as shown in a photograph of a WesternBright blot film exposed for 1 second. Each gel lane in FIGS. 1A and 1B shows the expression of FXN from a modified FXN gene of the invention compared with expression from a wild type nucleic acid sequence encoding FXN. That is, lane 1 shows expression driven by wild type non-modified nucleic acid encoding FXN (SEQ ID NO:2); lane 2 shows expression driven by IDT2 modified FXN gene (SEQ ID NO:3); lane 3 shows expression driven by IDT5 modified FXN gene (SEQ ID NO:9); lane 4 shows expression driven by JCAT modified FXN gene (SEQ ID NO:4); lane 5 shows expression driven by GeneArt modified FXN gene (SEQ ID NO:5); lane 6 shows expression driven by GenScript (control) modified FXN gene (SEQ ID NO:6); lane 7 shows expression driven by Genscript (low CpG) modified FXN gene (SEQ ID NO:7); and lane GFP shows expression transgene encoding green fluorescent protein, a detectable marker, which is encoded by the insert instead of a nucleic acid encoding FXN.

The data shown demonstrate that several modified FXN nucleic acid sequences—especially lanes 4 (JCAT), 5 (GeneArt), 6 (Genscript) and 7 (Genscript low CpG)—provided greater expression of frataxin in HeLa cells relative to the wild type nucleic acid sequence (lane 1). An actin loading control in each lane is as a protein loading control.

The GC nucleotide content in a nucleic acid sequence, typically expressed as a percentage of the total number of nucleotides in the sequence, can have multiple influences, including, but not limited to, the stability of the mRNA is increased, and the secondary structure and transgenes which are typically negatively impacted by increased GC content. Thus, the skilled artisan would appreciate that the GC content of a modified nucleic acid reflects a balance between increased stability of the nucleic acid, and mRNA transcribed therefrom, against the negative effect, e.g., on secondary structure mediated by increased GC content.

The CAI (codon adaptation index) is a measure of synonymous codon usage bias. The index uses a reference set of highly expressed genes from a species to assess the relative values of each codon, and a score for a gene is calculated from the frequency of use of all codons in that gene. The index assesses the extent to which selection has been effective in selecting the pattern of codon usage. It can be utilized for predicting the level of expression of a gene and for making comparisons of codon usage in different organisms/species. Human codon optimization was carried out on the frataxin gene to achieve a balance of the below factors:

Transctiption Efficiency—GC content, CpG dinucleotides content, Cryptic splicing sites, etc.;

Translation Efficiency—Codon usage bias, GC content, mRNA secondary structure, premature polyA sites, RNA instability motifs, internal ribosomal binding sites; and Protein refolding—codon usage bias, interaction of codon and anti-codon, RNA secondary structures.

Basically, codon optimization balances these variables to, preferably, achieve a higher expressing frataxin gene sequence, increase stability of the message (GC content, secondary structure in both DNA and RNA), and the like, as well-known in the art.

CpG islands can be recognized by Tol-like receptor nine (TLR9) in a transduced cell and can elicit an immune response to the foreign (exogenous) DNA. Accordingly, in one embodiment, the invention encompasses a modified nucleic acid encoding frataxin wherein the number of CpG islands has been reduced compared with the number of CpG island motifs in a wild type nucleic acid sequence (e.g., SEQ ID NO:2) encoding frataxin.

The CAI, percent GC content, and number of potential CpG island regions for each modified FXN gene exemplified herein is shown in Table 1 below.

TABLE 1

| FIG. 1A and 1B gel lane number | FXN gene name | Codon adaptation index (CAI) | % GC content | Number of potential CpG island regions | SEQ ID NO: |
|---|---|---|---|---|---|
| 1 | WT-FXN | 0.71 | 55 | 128 | 2 |
|   | Nucleotide sequence 22 | 0.71 | 55 | — | 10 |
|   | IDT-1 | 0.73 | 52 | 114 | 11 |
| 2 | IDT-2 | 0.76 | 56 | 124 | 3 |
|   | IDT-3 | 0.80 | 57 | 123 | 8 |
|   | IDT-4 | 0.74 | 54 | 123 | 12 |
| 3 | IDT-5 | 0.77 | 55 | 124 | 9 |
| 4 | JCAT | 0.98 | 69 | 144 | 4 |
| 5 | GeneART | 0.95 | 61 | 117 | 5 |
| 6 | Genescript (Control) | 0.87 | 57 | 257 | 6 |
| 7 | Genescript (low CpG) | 0.86 | 55 | 117 | 7 |

That is, for wild type nucleic acid encoding FXN (WT-FXN; SEQ ID NO:2), the nucleic acid sequence demonstrates a CAI of 0.71 and a % GC content of 55%. In contrast, the JCAT modified FXN gene demonstrates a CAI of 0.98 and a GC content of 69%, both of which are substantially higher than the values for WT-FXN.

Potential CpG Islands were identified using publicly available software found at http://www.bioinformatics.org/sms2/cpg_islands.html. The CpG Islands software reported potential CpG island regions using the method described by Gardiner-Garden and Frommer, 1987, J. Mol. Biol. 196(2): 261-282. The calculation was performed using a 200 base-pair (bp) window moving across the sequence at 1 bp intervals. CpG islands are defined as sequence ranges where the Obs/Exp value is greater than 0.6 and the GC content is greater than 50%. The expected number of CpG dimers in a window was calculated as the number of 'C's in the window multiplied by the number of 'G's in the window, divided by the window length. Thus, the potential CpG islands present in a nucleic acid sequence can be readily determined by inputting the sequence at issue into the window provided by software (indicated by the instructions to "Paste the raw sequence or one or more FASTA sequences into the text area below. Input limit is 100000 characters."). CpG islands are often found in the 5' regions of vertebrate genes, therefore this program can be used to highlight potential genes in genomic sequences.

Because of the high level of expression and the high GC content (55%), high CAI (0.86) and low number of CpG dinucleotides (117), the Genscript (low CpG) modified FXN gene was selected for production of a scAAV-2i8 vector used in the animal experiments set forth below.

Example 2: In vivo Treatment in a Mouse Model of Friedreich Ataxia

An art-recognized mouse model of FRDA (Perdomini et al., 2014, Nature Med. 20(5):542) was used to assess the potential efficacy of rAAV mediated FXN gene therapy. That is, three groups of mice were examined: untreated Mck positive control mice (Mck-Cre×FXN L3/WT), untreated Mck mutant mice (Mck-Cre×FXN L3/L-), and treated Mck mutant mice that received a dose of rAAV comprising a FXN gene wherein the modified FXN gene comprised the nucleic acid sequence of SEQ ID NO:7 (GenScript (low CpG)) and the FXN gene was cloned into the pTRs-KS-CBh-EGFP-BGH construct as described above to provide pTRs-KS-CBh-Genscript (low CpG)-bGHpolyA.

The rAAV-FXN vector used in the mouse studies further comprised a AAV2i8 capsid. Moreover, the pTRs-KS-CBh-Genscript (low CpG)-bGHpolyA construct further comprised a nucleic acid sequence encoding a detectable hemagglutinin tag (rAAV-FXN-HA) wherein the sequence encoding the HA tag was located 3' of the modified FXN gene such that expression of frataxin could be readily detected and localized by detecting the presence of HA, e.g., using an anti-HA antibody such as anti-HA mouse mAb (HA.11 clone 16B12, Covance Research Products, Inc., Princeton, N.J.). The vector was designated rAAV-FXN-HA.

The three animal groups of the study are listed and described in Table 2.

TABLE 2

| Groups label | Group No. | Dose Level vg/kg | No. of Animals Mixed gender | Termination Weeks of age |
|---|---|---|---|---|
| Mck positive control | Mck-Cre x FXN L3/WT | 0 | 8 | Week 8 |
| Untreated Mck mutant mice | Untreated Mck-Cre x FXN L3/L- | 0 | 8 | Week 8 |
| Treated Mck mutant mice | rAAV-FXN-HA treated Mck-Cre x FXN L3/L- | $1 \times 10^{13}$ | 8 | Week 8 |

A. Biomarker Study

Methods

Measurement of Galectin-3 and H-FABP in Plasma

Blood was collected by retro orbital puncture after isoflurane anaesthesia at the age of 5 weeks (2 weeks after treatment) and 8 weeks (5 weeks after treatment).

Galectin-3 was measured in plasma using the Mouse Galectin-3 Elisa Kit from RayBiotech according to manufacturer's instructions.

H-FABP was measured in plasma using the Mouse H-FABP Elisa Kit from HycultBiotech according to manufacturer's instructions.

Measurement of Succinate Dehydrogenase Activity in Heart Homogenate

Upon sacrifice, the heart was collected and half of the heart of 4 mice of each group was snap frozen for the measurement of SDH activity.

SDH activity measurement in heart homogenate was performed following the instruction of the Succinate Dehydrogenase Activity Colorimetric Assay Kit (Catalog # K660-100) from Biovision.

Measurement of Human Frataxin in Tissues

Upon sacrifice, heart (half), skeletal muscle (gastrocnemius) and liver tissues were collected and snap frozen for the measurement of frataxin.

The measurement in tissue homogenates was performed following the instructions of the Human Frataxin Elisa Kit (Abcam; ab176112).

Histology

Cerebellum (including dentate nucleus), gonads, heart, kidney, liver, lung, pancreas, skeletal muscle (gastrocnemius and soleus), spleen and cervical, thoracic and lumbar vertebras were formol-fixed. Vertebras were then decalcified using EDTA solution. All organs were paraffin embedded to obtain 5 µm-thick sections; transversal sections for vertebras (including both spinal cord and dorsal root ganglia) and heart. All organs were hematoxylin and eosin stained; cardiac fibrosis was evaluated using Masson's trichrome staining.

Echocardiography:

Transthoracic Echocardiographic images were captured by the mean of a 30 MHz linear probe (MS 400) on a Vevo-2100 Visual Sonics echograph in anesthetized mice (Isoflurane 1-2%).

The following parameters are measured to assess:
a) The cardiac morphology and ventricular systolic function (Short axis, SAX): left ventricular end-diastolic (LVEDD) and end systolic diameters (LVESD), septal (SW) and posterior wall thicknesses (PVV), left ventricular mass (LVM=1.055× [(EDD+SW+PW) 3−EDD3)]), Ejection and shortening Fraction and cardiac output;
b) Hemodynamic profiles: pulmonary and aortic artery velocity and pressures to detect intra-cardiac pressures changes (AoV and RV function).

Mice

Mice were maintained in a temperature- and humidity-controlled animal facility, with a 12-h light-dark cycle and free access to water and a standard rodent chow (D03, SAFE, Villemoisson-sur-Orge, France). All animal procedures and experiments were approved by the local ethical committee (Comité d'Ethique en Expérimentation Animale IGBMC-ICS) for Animal Care and Use (Com'Eth 2011-007).

Bi-daily clinical observation of mice was performed, body weight was recorded weekly and food intake every 2 days until the end of the protocol.

For bio-distribution and gene therapy studies, 3-weeks-old mice were anesthetized with isoflurane (1-2%) and injected intravenously into the retro-orbital vein with a rAAV-FXN-HA vector at a dose of $1\times10^{13}$ vg/kg for the treated group and with an equivalent volume of saline water for Untreated MCK Mutant mice and Control.

Mouse cardiac function was evaluated under isoflurane anesthesia (1-2%) by echocardiography 2 days before starting the treatment (baseline phenotype), at 5 weeks of age (14 days after treatment) and 7 weeks of age (28 days after treatment). At 5 and 8 weeks of age, blood collection was performed to measure the concentration of the heart type fatty acid binding protein (H-FABP), galectin-3 and Succinate dehydrogenase (SDH) as detailed elsewhere herein.

Upon sacrifice, body weight, body length, heart, spleen, kidney, adrenals, and liver weights were recorded from all animals. Adrenals, cerebellum, cervical, thoracic and lumbar vertebras, gonads (testes and ovaries), heart, kidney, liver, lungs, pancreas, prostate in males, skeletal muscle (gastrocnemius and soleus), spleen and thymus were collected from 4 animals per group for pathological evaluation and ELISA assays.

Cerebellum (including dentate nucleus), cervical, thoracic and lumbar dorsal root ganglia, heart, kidneys, liver, lungs, gonads, pancreas, skeletal muscle (gastrocnemius and soleus), and spleen of 4 other animals per group were collected and immediately snap frozen for molecular biology.

Results

Identification of Potential Biomarkers

The levels of various biomarkers were determined in three groups of mice: untreated Mck positive control, untreated Mck mutant mice and treated Mck mutant mice that received a dose of rAAV2i8 comprising a FXN gene and further comprising a nucleic acid encoding an HA tag peptide (AAV-FXN-HA).

Measurement of Galectin-3 and H-FABP in Plasma

Blood was collected by retro orbital puncture after isoflurane anaesthesia at the age of 5 weeks (2 weeks of AAV treatment for the treated Mck mutant mice) and 8 weeks (5 weeks of rAAV treatment for the treated Mck mutant mice group) and the levels of galectin-3 and H-FABP were measured using standard methods.

Galectin-3:

At the age of 5 weeks, galectin-3 levels were comparable between the 3 groups, even if galectin-3 levels tended to be higher in the untreated Mck positive control group and in the treated Mck mutant mice group compared to the untreated Mck mutant mice group.

As show in Table 3, at the age of 8 weeks, galectin-3 levels were significantly lower in the untreated Mck mutant group than in the negative control group. Galectin-3 levels tended to be lower in the experimental group than in the negative control group, while Galectin-3 levels were comparable between the experimental group and the positive control group.

TABLE 3

|  | Plasma Galectin-3 level (ng/ml) | |
| --- | --- | --- |
|  | week 5 mean +/− sem | week 8 mean +/− sem |
| Untreated Mck positive control mice (n = 8) | 41.2 +/− 3.5 | 68 +/− 7.8 |
| Untreated Mck mutant mice (n = 8) | 49.7 +/− 3.6 | 42 +/− 2.1 |
| Treated Mck mutant mice (n = 8) | 49.7 +/− 4.4 | 48.9 +/− 4.5 |

Surprisingly, mice of the untreated Mck positive control group displayed higher levels of Galectin-3 at the age of 8 weeks than at the age of 5 weeks, while the levels of Galectin-3 at the age of 8 weeks were comparable to the levels at the age of 5 weeks for the untreated Mck mutant mice group and for the treated Mck mutant mice group.

In conclusion, it appears that Galectin-3 is not an appropriate heart biomarker for this study on Mck mice. The mice of the untreated Mck mutant mice group did not show an expected, if galectin-3 was an appropriate biomarker, increase in this parameter.

H-FABP:

Great variability was observed in H-FABP levels between mice within the same sample group using standard methods of detection.

As shown in Table 4, H-FABP blood levels were comparable between the 3 groups of mice both at the age of 5 weeks and 8 weeks.

TABLE 4

|  | Plasma H-FABP (ng/ml) | |
| --- | --- | --- |
|  | week 5 mean +/− sem | week 8 mean +/− sem |
| Untreated Mck positive control (n = 8) | 177.8 +/− 33.9 | 98.8 +/− 25.0 |
| Untreated Mck mutant mice (n = 8) | 187.1 +/− 38.8 | 139.6 +/− 41.5 |
| Treated Mck mutant mice (n = 8) | 232.2 +/− 53.3 | 129.6 +/− 25.8 |

No significant change was observed in H-FABP levels between the age of 5 and 8 weeks in each group.

In conclusion, it seems that H-FABP is not the appropriate heart biomarker for this study on Mck mice; the expected increase in this parameter was not observed in the untreated Mck mutant group and an important variability was observed between mice in a same group.

SDH Activity in Heart Homogenates

SDH activity was measured in heart homogenate from heart collected at the end of the study (8 weeks of age, 5 weeks of AAV treatment in the treated mutant mice group) using standard methods. Each group was comprised of four (4) mice.

The results shown in Table 5 show that SDH activity was comparable between the 3 groups of mice. No decrease was observed in SDH activity in the untreated Mck positive control group compared to the untreated Mck mutant group.

TABLE 5

|  | SDH activity in heart homogenate (U/g proteins) |
| --- | --- |
| Untreated Mck positive control (n = 4) | 4.14 +/− 0.52 |
| Untreated Mck mutant mice (n = 4) | 3.64 +/− 0.77 |
| Treated Mck mutant mice (n = 4) | 4.24 +/− 0.62 |

An important variability in SDH activity was observed between mice in a same group. Further, the expected decrease in SDH activity in the untreated Mck positive control group was not observed.

Frataxin Levels in Heart, Skeletal Muscle and Liver Homogenates

The level human frataxin protein was measured from heart, skeletal muscle and liver collected at sacrifice using standard methods as shown in Table 6.

Human frataxin was not detectable in any of the tissues examined (heart, skeletal muscle and liver) of the untreated Mck positive control and the untreated Mck mutant groups (i.e., the level was below the lowest limit of detection [LLD] of the assay).

In treated Mck mutant mice receiving rAAV-FXN, human frataxin protein was detected in heart homogenate at the level of 38.35+/−1.99 ng/mg, and in skeletal muscle at a lower concentration: 4.57+/−0.39 ng/mg. Furthermore, traces of human frataxin were detected in the liver (0.07+/−0.01 ng/mg of proteins).

TABLE 6

|  | Frataxin in tissue (ng/mg proteins) | | |
| --- | --- | --- | --- |
|  | heart mean +/− sem | skeletal muscle mean +/− sem | liver mean +/− sem |
| Negative control (n = 4) | <LLD | <LLD | <LLD |
| Positive control (n = 4) | <LLD | <LLD | <LLD |
| Experimental group (n = 4) | 38.35 +/− 1.99 | 4.57 +/− 0.39 | 0.07 +/− 0.01 |

These data demonstrate that treatment with rAAV vector comprising a FXN gene can increase frataxin levels in a mouse model of Friedreich ataxia (FRDA) Additionally, these data show that FXN levels can be increased in vivo by rAAV-FXN systemic administration such that FXN levels are increased in heart and, to a lesser extent, skeletal muscle, with much lower level in the liver. Thus, these data demonstrate that in vivo FXN levels can be selectively increased in affected tissues, e.g., heart and skeletal muscle, while minimizing delivery of FXN where it is not needed and/or desired—i.e., to the liver.

Gross Pathology

Untreated Mck positive Control male mice were significantly longer compared to untreated and AAV-treated Mck mutant animals (9.39 cm vs 8.89 cm [+5.62%]. P=0.011 [t-test]). No other significant macroscopic lesion was observed, especially no macroscopic lesion or significant change was observed in heart weight in both males and females.

Histology

Heart

Minimal interstitial fibrosis was observed in one untreated Mck positive Control animal (#58). All other 3 untreated Mck positive Control group hearts were normal.

However, minimal (mouse #38) and moderate (mice #41, #49, and 81) interstitial fibrosis was observed in all 4 untreated Mck mutant animals analyzed. This lesion was associated to endocardiac focus of cardiomyocytes swelling in mice #38 (minimal) and #81 (slight). Fibrosis was associated to moderate macrophagic inflammation, minimal disseminated swelling and slight vacuolization of cardiomyocyte, in mice #41 and #49. Anitschkow (Howl eye-shaped) nuclei were observed in mice #41 and #81.

In stark contrast to the untreated Mck mutant cohort, on overall assessment, hearts of rAAV-FXN-treated Mck mutant mice appeared normal except that few Anitschkow nuclei were observed in mice #47 and #13.

Kidneys

In all groups, significant mineralization was frequently observed in lumen of multiple medullar tubules. Frequency was 4/4 for untreated Mck positive control animals (although they express the Cre transgene), 3/4 for untreated Mck mutant animals and 2/4 for treated Mck mutant animals receiving a dose of rAAV-FXN. Severity of the mineralization appeared decreased in the rAAV-treated Mck Mutant group compared to untreated Mck positive Control and untreated Mck mutant groups. Tubular basophilia (regeneration) was observed in 2/4 animals in the untreated Mck positive control group, in 3/4 animals in the untreated Mck mutant group and in 1 animal in the AAV-treated Mck mutant group.

Liver: minimal periportal inflammation was observed in one untreated Mck positive control animal (#38).

Lung: slight peribronchial inflammation was observed in one untreated Mck mutant animal (#41).

No other significant microscopic lesion was observed. Especially, spinal cord, dorsal root ganglia, and cerebellum were all normal.

Echocardiography

Basal Phenotype before Treatment

Echocardiography measurements showed a reduced left-ventricular function in untreated Mck Mutant males mice compared to untreated Mck positive Control. This cardiac insufficiency is characterized by a decrease of the left ventricular (LV) contractility (shortening fraction and ejection fraction) and an increase of the LV volume, both systolic and diastolic. At that stage, no cardiac phenotype was observed in untreated Mck Mutant female mice.

Figures 4A, 4B:
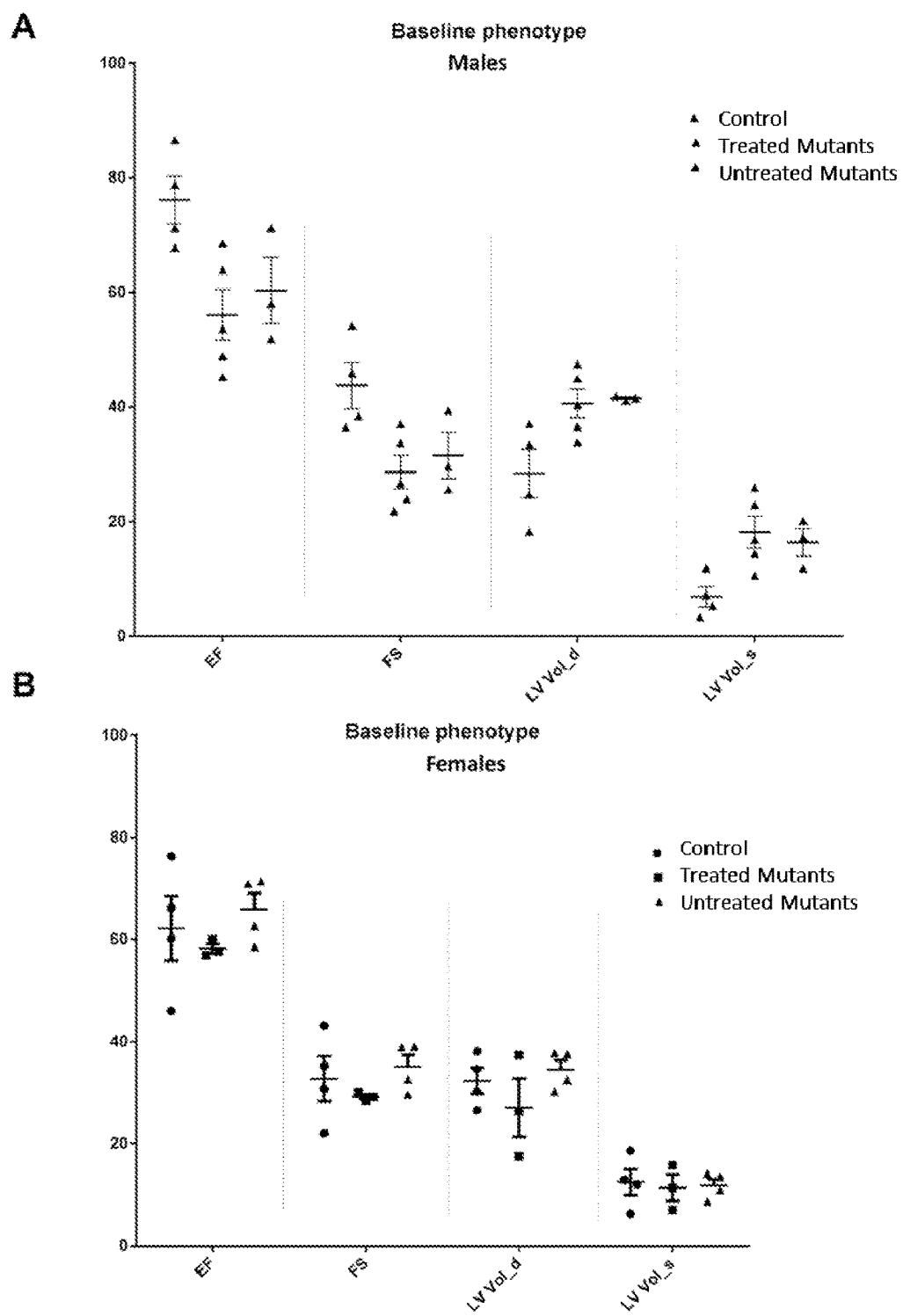
FIGS. 4A and 4B show graphs illustrating the baseline cardiac phenotype in control, treated mutant and untreated mutant male (FIG. 4A) and female (FIG. 4B) mice.

FIG. 4A shows graphs evaluation of the systolic function and LV volumes by echocardiography at 3 weeks of age (A) males and (B) females. Data are mean±S.E.M of 8 mice per groups. The data of Mck Mutant (both treated and untreated) mice were compared to the untreated Mck positive Control group using multiple t-tests comparisons (Sidak-Bonferroni method). *p<0.05

Results 14 Days after rAAV Treatment (5 Weeks of Age):

To investigate the potential of a gene therapy approach for the treatment of the FRDA cardiomyopathy, a single intravenous injection of AAV.FXN-HA at a dose of $1 \times 10^{13}$ vg/kg was administered to 3-weeks-old Mutant mice (treated Mck mutant group). 14 days after injection (5 weeks of age), echocardiography measurements showed an improvement of the cardiac hemodynamics (cardiac output) and a near normal morphological development in Treated Mck Mutant males (contractility, LV mass). In contrast, cardiac insufficiency was still observed in untreated Mck Mutant mice. Surprisingly, in females, the cardiac contractility defect was observed in all Mck Mutant mice whether treated or untreated.

Figures 5A, 5B:
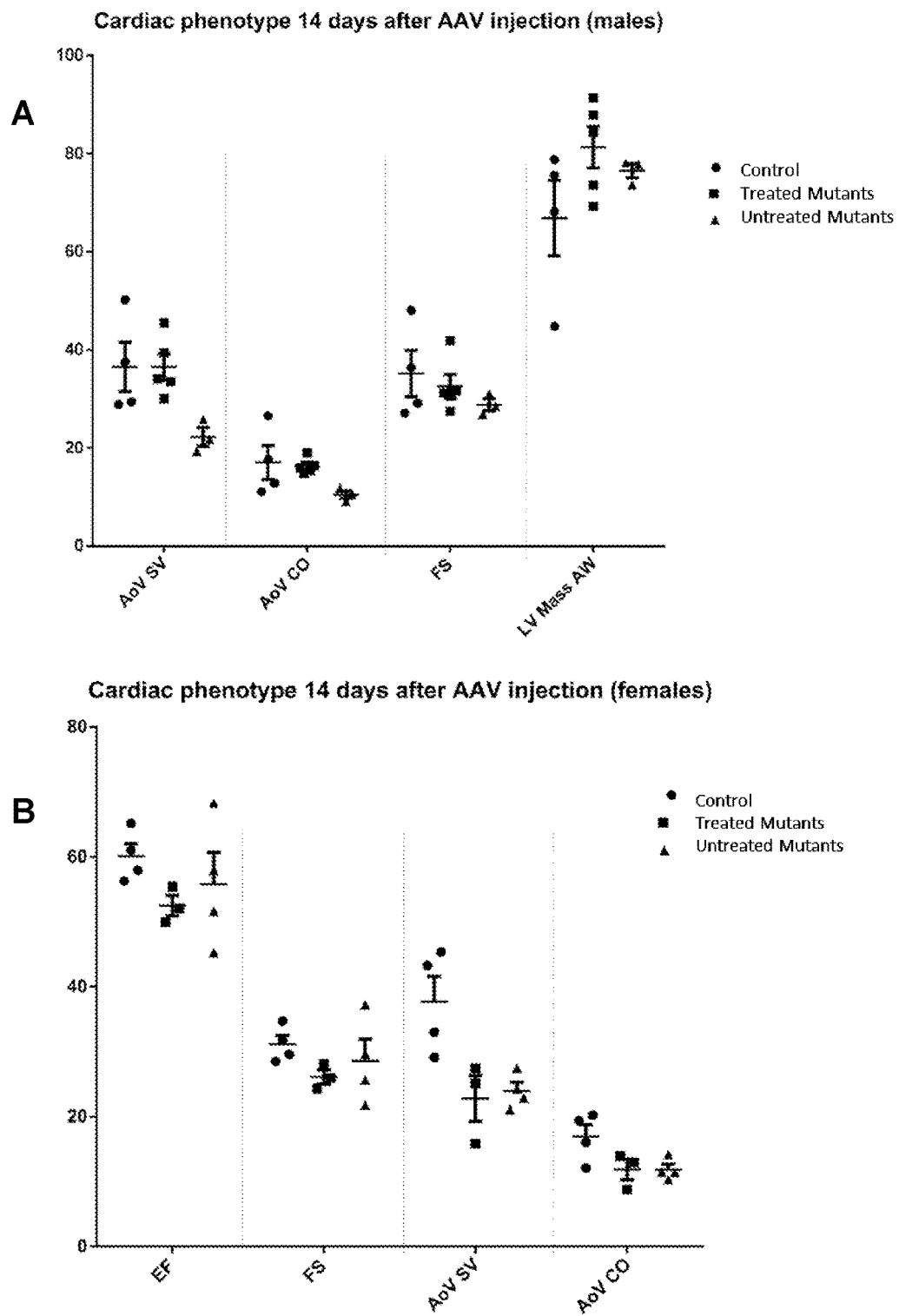
FIGS. 5A and 5B show graphs illustrating the reversal of FRDA cardiac phenotype in treated Mck mutant mice compared with the cardiac phenotype in untreated Mck mutant mice at 5 weeks of age (and 14 days post-treatment in treated mutants).

FIGS. 5A-5B show the evaluation of the systolic function and LV volumes by echocardiography at 5 weeks of age in males (FIG. 5A) and females (FIG. 5B). Data are mean±S.E.M of 8 mice per groups. The data of Mutant mice were compared to the Control groups using multiple t-tests comparisons (Sidak-Bonferroni method). *p<0.05.

Results 28 Days after rAAV Treatment (7 Weeks of Age):

Twenty-eight (28) days rAAV treatment (7 weeks of age), treated Mck mutant males and females were fully normalized and became indistinguishable between them and from untreated Mck positive control mice. This, a complete correction (males) and prevention (females) of the cardiac disease was demonstrated in treated Mck mutant mice. In contrast, untreated Mck Mutant mice developed a rapidly progressing cardiac insufficiency, with a marked decrease in left ventricle shortening fraction and cardiac output, as well as left ventricle hypertrophy.

Figures 6A, 6B, 6C:
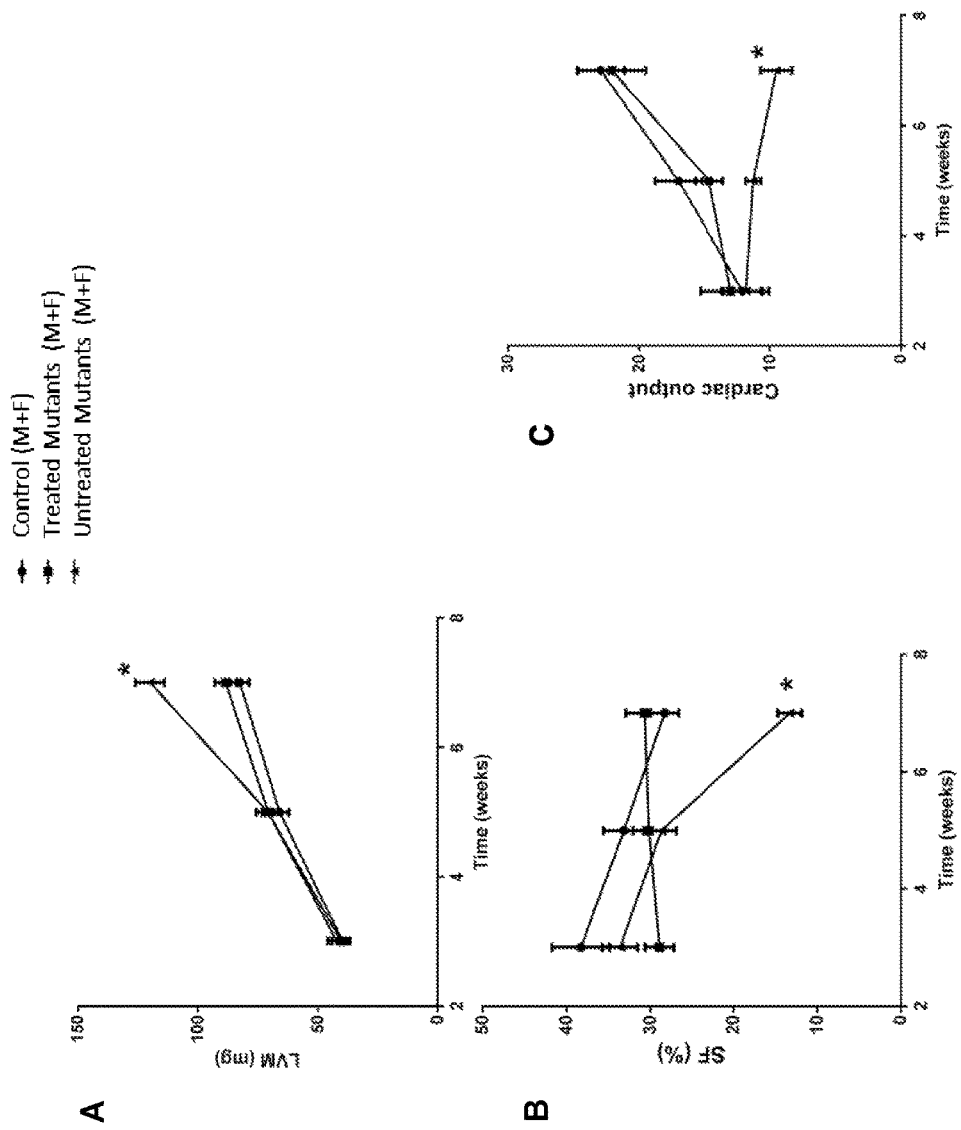
FIGS. 6A-6C show graphs illustrating cardiac function in male and female control mice (circles), treated mutants male and female mice (squares), and untreated mutant male and female mice (triangles) twenty-eight (28) days post-rAAV-FXN treatment in the treated Mck mutant group.

FIGS. 6A-6C show graphs depicting data obtained using echocardiography assessment of the left ventricle mass (LVm), shortening fraction (SF) and cardiac output for untreated Mck positive control, and Treated and Untreated Mck mutant mice over successive weeks. Data are mean±S.E.M of 8 mice per groups. The data of Mck Mutant mice were compared to the untreated Mck positive control group using multiple t-tests comparisons (Sidak-Bonferroni method). *p<0.05.

Conclusions

Results of Echocardiography

In this study, the efficacy of an rAAV-FXN optionally further comprising a detectable hemagglutinin tag (HA) vector (referred to herein as rAAV-FXN-HA) at a dose of $1 \times 10^{13}$ vg/kg was assessed. This dose was approximately 5-fold less than the dose previously described in the same Mck mouse cardiac-specific Friedreich ataxia mouse model using an rrhAAV10 vector encoding wild type FXN (Perdomini et al., 2014, Nature Medicine 20(5):542).

As shown in FIG. 5A, at 3 weeks of age, the untreated Mck Mutant male mice started to develop a left ventricular (LV) dysfunction, not observed in females of the same group at the same age (FIG. 5B). Fourteen (14) days after the AAV.FXN-HA injection (at 5 weeks of age), a progressive correction of the cardiac phenotype was observed in Mck mutant males, but it was less in Mck mutant females. Without wishing to be bound by any particular theory, this difference may be due to a later start of the cardiac phenotype in females compared to males or to the reduced number of mice used so far in this protocol.

These results suggest that systemic administration of rAAV-modified FXN reverses the cardiac disease phenotype in Mck mutant mouse model of FRDA. These results further suggest that rAAV-modified FXN administration can prevent and/or reverse FRDA in a subject in need thereof.

Twenty-eight (28) days post-rAAV-FXN injection, a complete recovery of the cardiac function was observed in treated Mck mutant males and females, suggesting a robust correction of the pathology by the injected FXN transgene. That is, the data shown in FIGS. 6A-6C demonstrate the correction in the FRDA cardiac phenotype by twenty-eight (28) days after rAAV-FXN administration. More specifically, FIG. 6A shows the left ventricle mass (LVm) of both treated Mck mutant mice and control (VVT wild type Mck-Cre mice) is indistinguishable while the untreated (triangles) Mck mutant mice exhibit significantly greater LVm (*p<0.05). FIG. 6B shows data demonstrating that by 28 days after rAAV-FXN treatment, both positive control (VVT L3 Mck-Cre mice; circles) and treated Mck mutant (L-) mice (squares) demonstrated substantially identical shortening fraction (SF) measurements. In contrast, FIG. 6B demonstrates that untreated Mck mutant mice (triangles) demonstrated greatly decreased SF (*p<0.05). In addition, FIG. 6C shows data demonstrating that by 28 days following treatment with rAAV, treated Mck mutant mice (squares) exhibited cardiac output that was indistinguishable from control mice (circles) compared with untreated Mck mutant mice (triangles) which showed markedly decreased cardiac output (triangles; *p<0.05). All (treated and untreated) Mck mutant mice were compared with the control untreated mice using multiple t-test comparisons (Sidak-Bonferroni method). For each graph shown in FIGS. 6A-6C, *<0.05 is indicated.

These data amply demonstrate that administration of rAAV comprising modified nucleic acid encoding frataxin can reverse, and/or prevent, the Mck phenotype in an art-recognized mouse model of FRDA. Thus, these data support that rAAV-modified FXN mediated treatment may be a potential useful therapeutic to treat, or prevent, FRDA, or a disease, disorder or condition mediated by decreased level of wild type (e.g., functional) frataxin, in a subject in need thereof. Although these data demonstrate that rAAV-modified-FXN administered systemically can treat or prevent FRDA, these results further support that therapy also includes other, e.g., more direct, routes of rAAV-FXN administration, such as, but not limited to, intracranial or direct cardiac administration. That is, because systemic administration was demonstrated to be therapeutic, one skilled in the art would understand based upon the disclosure provided herein that more direct administration routes can also provide a therapeutic benefit.

These results strongly support that gene therapy using rAAV vector delivery of a modified FXN gene is a potential therapeutic approach for patients with FRDA and to treat or prevent kidney stones in a subject demonstrating a decreased level of wild type/functional frataxin.

Example 3: Histology Study of in vivo Administration of rAAV-FXN in a Mouse Model of Friedreich Ataxia Study Design Twenty four (24) 8-weeks old C57BL6/N male and female mice were assessed for histopathological analyses.

Eight (8) mice harbored a Mck-Cre transgene (MCK: Muscular Creatine Kinase) associated to a functional engineered human Frataxin allele (Mck-Cre×FXN L3/WT; hereinafter referred as "Mck positive control mice"). Sixteen (16) mice harbored the same transgene now associated to an inactive engineered frataxin allele (Mck-Cre×FXN L3/L-; hereinafter referred to as "Mck mutant mice"). Among the Mck mutant mice, eight (8) were injected with a frataxin-encoding rAAV2i8 (rAAV-FXN; $10^{13}$ vg/kg) (hereinafter "treated Mck mutant mice"). The remaining eight (8) Mck mutant mice received an equivalent volume of saline water (hereinafter "untreated Mck mutant mice"). The positive control mice group (Mck-Cre×FXN L3/WT) were administered saline water. See Table 7 below.

TABLE 7

| Groups label | Group No. | Dose Level vg/kg | No. of Animals (Mixed gender) | Termination Weeks of age |
|---|---|---|---|---|
| Mck positive control mice | Mck-Cre x FXN L3/WT | 0 | 8 | Week 8 |
| Untreated Mck mutant mice | Untreated Mck-Cre x FXN L3/L- | 0 | 8 | Week 8 |
| Treated Mck mutant mice | rAAV-FXN-HA treated Mck-Cre x FXN L3/L- | $1 \times 10^{13}$ | 8 | Week 8 |

Methods

Upon sacrifice, body weight, body length and heart, spleen, kidney, adrenals, and liver weight weights were recorded from all animals. Adrenals, cerebellum, cervical, thoracic and lumbar vertebras, Gonads (testes and ovaries), heart, kidney, liver, lungs, pancreas, prostate in males, skeletal muscle (gastrocnemius and soleus), spleen, and thymus, were collected from four (4) animals per group for pathological evaluation and ELISA assays.

Cerebellum (including dentate nucleus), cervical, thoracic and lumbar dorsal root ganglia, heart, kidneys, liver, lungs, gonads, pancreas, skeletal muscle (gastrocnemius and soleus), and spleen of 4 other animals per group were collected and immediately snap frozen for molecular biology.

Histology

Cerebellum (including dentate nucleus), gonads, heart, kidney, liver, lung, pancreas, skeletal muscle (gastrocnemius and soleus), spleen and cervical, thoracic and lumbar vertebras were formol-fixed. Vertebras were then decalcified, using EDTA solution. All organs were paraffin embedded to obtain 5 μm-thick sections, transversal sections for vertebras (including both spinal cord and dorsal root ganglia) and heart. All organs were hematoxylin and eosin stained. Cardiac fibrosis was evaluated using Masson's trichrome staining.

ELISA Assays

Half of the heart, right lobe of the liver, and soleus and gastrocnemius muscles were snap frozen immediately after collection.

Results

Gross Pathology

Mck positive control male mice were significantly longer compared to untreated Mck mutant mice and treated Mck mutant mice (9.39 cm vs 8.89 cm [+5.62%]. P=0.011 [t-test]). No other significant macroscopic lesion was observed, especially no macroscopic lesion or significant change was observed in heart weight in both males and females.

Histology

Heart

Mck-Cre×FXN L3/WT: Minimal interstitial fibrosis was observed in one Mck positive control animal (#58). All other 3 positive control mouse hearts were normal.

Untreated Mck-Cre×FXN L3/L-: In contrast, minimal (mouse #38) and moderate (mice #41, #49, and 81) interstitial fibrosis was observed in all 4 untreated Mck mutant mice analyzed. This lesion was associated to endocardiac focus of cardiomyocytes swelling in mice #38 (minimal) and #81 (slight). Fibrosis was associated to moderate macrophagic inflammation, minimal disseminated swelling and slight vacuolization of cardiomyocyte, in mice #41 and #49. Anitschkow (owl eye-shaped) nuclei were observed in mouse #41 and #81.

Treated Mck-Cre×FXN L3/L-: In contrast to untreated Mck mutant mice, hearts of rAAV-FXN treated Mck mutant mice appeared normal except that a few Anitschkow nuclei were observed in mice #47 and #13.

Kidneys

In all three groups, significant mineralization was frequently observed in the lumen of multiple medullar tubules. Frequency of mineralization was 4/4 for Mck positive control animals, 3/4 for untreated Mck mutant animals and 2/4 for rAAV-FXN treated Mck mutant animals. The severity of mineralization appeared decreased in rAAV-FXN treated Mck mutant group compared to Mck positive control and untreated Mck mutant groups. Tubular basophilia (re-generation) was observed in 2/4 animals in Mck positive control mice, in 3/4 animals in the untreated Mck mutant group and in 1 animal in the rAAV-FXN treated Mck mutant group.

Liver: minimal periportal inflammation was observed in one Mck positive control animal (#38).

Lung: slight peribronchial inflammation was observed in one untreated Mck mutant animal (#41).

No other significant microscopic lesion was observed. Especially, spinal cord, dorsal root ganglia, and cerebellum were all normal for all groups.

Results of Histology

With respect to histology, owl eye-nuclei, swelling and vacuolization observed in cardiomyocytes of untreated Mck mutant mice are all landmarks for cardiac degeneration. Interstitial fibrosis associated to macrophage inflammation may correspond to cardiomyocyte cell death. Thus, cardiomyocytes of untreated Mck mutant mice degenerate, meaning cells undergo decreased function and pathology evolve to cell death and subsequent heart failure.

Strikingly, rAAV-FXN systemic delivery reverses this phenotype and rAAV-treated Mck mutant mice (both males and females) appeared normal and showed no significant sign of cardiomyocytes degeneration. These data demonstrate that the rAAV-huFXN transduction is sufficiently efficient to reverse the endogenous mouse Fxn gene inactivation effects. Thus, these data further support that rAAV-modified FXN mediated systemic administration can reverse and/or prevent a disease, disorder or condition mediated by a decreased level of wild type (functional) frataxin, such as, but not limited to, Friedreich ataxia, in a subject in need thereof. As noted previously, the skilled artisan, armed with the teachings of the instant disclosure, would appreciate that other routes of administration, e.g., more direct routes including intracranial and into the heart, could be used to provide a therapeutic benefit to the subject in need thereof.

Analysis of the kidneys identified the presence of kidney stones in medulla of both untreated Mck positive control and untreated Mck mutant animals which is an uncommon lesion. Since no specific diet was proposed to these animals and considering their age, the frequency and the severity of the lesions strongly suggest that this is not an incidental lesion, but a lesion related to genotype. Interestingly, this lesion severity is partially reduced by rAAV-FXN treatment, suggesting that the kidney stones development is related to an alteration in the Fxn function and or in the level of the protein. Hence, the so-called L3 allele, in which the mouse frataxin gene is flanked by loxP sequences (although in the intronic regions), could be a hypomorph allele. This would be consistent with the critical role of mitochondria in these cells to maintain trans-epithelial electrolyte active transports. To the best of applicants' knowledge and belief, these lesions have not been reported in Friedreich ataxia clinical observations, or in FRDA mouse models, to date.

Therefore, the invention encompasses a method of treating or preventing kidney disease, disorder or condition, including, but not limited to, development or growth of kidney stones, in a subject in need thereof, wherein the kidney disease, disorder or condition is mediated by a decreased level of frataxin (e.g., functional and/or wild type frataxin) in the subject.

In one embodiment, the invention includes assessing the level of frataxin in a subject, comparing the level of frataxin in the subject with the level of frataxin in a subject known not to be afflicted with kidney stones and/or comparing the level of frataxin with a "standard level of frataxin" determined for otherwise healthy individuals or known in the art, and administering a rAAV-modified frataxin to the subject if the level of frataxin in the subject is less than the level of frataxin in an otherwise healthy individual and/or below the standard level of frataxin, thereby treating and/or preventing a kidney stone in the subject.

Finally, HA staining can be used to detect rAAV-FXN-HA within cells. First, this would be important to quantitate how many cells should express FXN to restore or maintain the cardiac function. Second, the Mck gene (and thus the Cre recombinase driven by the Mck promoter) is not expected to be expressed in kidney. Detecting, or not, rAAV-FXN-HA in kidney may help to elucidate whether the kidney stone formation is an unexpected direct effect of HA-FXN on medulla homeostasis, or not.

CONCLUSION

In sum, the data presented herein demonstrate that administration, even systemically, of rAAV encoding a modified FXN gene can treat (prevent and/or reverse) the effects associated with a decrease or absence of frataxin. Thus, the data support that rAAV mediated expression of frataxin in cells and subjects in need thereof can be a useful therapeutic to treat a disease or disorder associated with or mediated by a lack or deficit of frataxin such as, but not limited to, Friedreich ataxia.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 8

| | SEQUENCES | | |
|---|---|---|---|
| SEQ ID NO: 1 | Amino acid sequence of human wild type frataxin | MWTLGRRAVA TGLLASPSPA QAQTLTRVPR PAELAPLCGR RGLRTDIDAT CPRRASSNQR GLNQIWNVKK QSVYLMNLRK SGTLGHPGSL DETTYERLAE ETLDSLAEFF EDLADKPYTF EDYDVSFGSG VLTVKLGGDL GTYVINKQTP NKQIWLSSPS SGPKRYDWTG KNWVYSHDGV SLHELLAAEL TKALKTKLDL SSLAYSGKDA | |
| SEQ ID NO: 2 | Nucleotide sequence encoding wild type frataxin (FIGS. 1A-1B; lane 1) | ATGTGGACTCTCGGGCGCCGCGCAGTAGCCGGCCTCCTGGCGT CACCCAGCCCAGCCCAGGCCCAGACCCTCACCCGGGTCCCGCG GCCGGCAGAGTTGGCCCCACTCTGCGGCCGCCGTGGCCTGCGC ACCGACATCGATGCGACCTGCACGCCCCGCCGCGCAAGTTCGA ACCAACGTGGCCTCAACCAGATTTGGAATGTCAAAAAGCAGAG TGTCTATTTGATGAATTTGAGGAAATCTGGAACTTTGGGCCAC CCAGGCTCTCTAGATGAGACCACCTATGAAAGACTAGCAGAGG AAACGCTGGACTCTTTAGCAGAGTTTTTTGAAGACCTTGCAGA | |

TABLE 8-continued

| | SEQUENCES | |
|---|---|---|
| | | CAAGCCATACACGTTTGAGGACTATGATGTCTCCTTTGGGAGT GGTGTCTTAACTGTCAAACTGGGTGGAGATCTAGGAACCTATG TGATCAACAAGCAGACGCCAAACAAGCAAATCTGGCTATCTTC TCCATCCAGTGGACCTAAGCGTTATGACTGGACTGGGAAAAAC TGGGTGTACTCCCACGACGGCGTGTCCCTCCATGAGCTGCTGG CCGCAGAGCTCACTAAAGCCTTAAAAACCAAACTGGACTTGTC TTCCTTGGCCTATTCCGGAAAAGATGCT |
| SEQ ID NO: 3 | IDT2 optimized nucleotide sequence encoding frataxin (FIGS. 1A-1B; lane 2) | ATGTGGACACTGGGCAGAAGGGCGGTGGCCGGACTGTTGGCGA GTCCCAGTCCCGCGCAGGCGCAGACCCTTACTAGGGTGCCGCG GCCCGCGGAGCTGGCGCCACTCTGCGGTCGCCGCGGTCTGAG AACGGACATTGATGCCACTTGTAcACCTCGGAGGGCCAGCT CCAACCAAAGGGGCCTTAATCAAATTTGGAACGTGAAGAAGC AGTCCGTCTACCTGATGAACCTTCGGAAGTCAGGGACCCTGG GCCACCCGGGAAGCTTGGATGAAACAACTTACGAAAGGTTG GCGGAGGAGACCTTGGATTCTCTTGCAGAGTTCTTCGAAGAC CTGGCTGATAAGCCTTACACCTTTGAGGACTACGATGTGTCTT TTGGATCTGGAGTGCTGACCGTTAAACTGGGCGGGGATCTGGG CACCTACGTGATTAACAAGCAAACTCCAAACAAGCAGATCT GGCTTTCAAGCCCCAGTAGCGGGCCAAAACGCTACGATTGG ACCGGAAAGAATTGGGTTTACAGCCACGATGGCGTTTCACTGC ACGAGCTTCTGGCAGCAGAACTGACAAAAGCACTCAAGACGAA GCTCGACTTGTCATCCTTGGCATACTCCGGAAAGGATGCC |
| SEQ ID NO: 4 | JCAT Optimized Nucleotide sequence encoding frataxin (FIGS. 1A-1B; Lane 4) | ATGTGGACCCTGGGCCGCCGCGCCGTGGCCGGCCTGCTGGCC AGCCCCAGCCCCGCCCAGGCCCAGACCCTGACCCGCGTGCCC CGCCCCGCCGAGCTGGCCCCCCTGTGCGGCCGCCGCGGCCTGC GCACCGACATCGACGCCACCTGCACCCCCCGCCGCGCCAGCA GCAACCAGCGCGGCCTGAACCAGATCTGGAACGTGAAGAAGC AGAGCGTGTACCTGATGAACCTGCGCAAGAGCGGCACCCTGG GCCACCCCGGCAGCCTGGACGAGACCACCTACGAGCGCCTGG CCGAGGAGACCCTGGACAGCCTGGCCGAGTTCTTCGAGGACC TGGCCGACAAGCCCTACACCTTCGAGGACTACGACGTGAGCT TCGGCAGCGGCGTGCTGACCGTGAAGCTGGGCGGCGACCTGG GCACCTACGTGATCAACAAGCAGACCCCCAACAAGCAGATCT GGCTATCTAGCCCCAGCAGCGGCCCCAAGCGCTACGACTGGA CCGGCAAGAACTGGGTGTACAGCCACGACGGCGTGAGCCTGC ACGAGCTGCTGGCCGCCGAGCTGACCAAGGCCCTGAAGACC AAGCTGGACCTGAGCAGCCTGGCCTACAGCGGCAAGGACG CC |
| SEQ ID NO: 5 | GeneArt optimized nucleotide sequence encoding frataxin (FIGS. 1A-1B; Lane 5) | ATGTGGACACTGGGGAGAAGGGCTGTGGCCGGACTGCTGGCTT CTCCATCTCCAGCCCAGGCCCAGACCCTGACCAGAGTGCCTAG ACCTGCCGAACTGGCCCCACTCTGTGTGGCAGAAGAGGCCTGAGA ACCGACATCGACGCCACCTGTACCCCCAGAAGGGCCAGCAGCA ATCAGCGGGGCCTGAATCAGATCTGGAACGTGAAGAAACAGAG CGTGTACCTGATGAACCTGAGAAAGAGCGGCACCCTGGGCCAC CCTGGAAGCCTGGATGAGACAACCTACGAGCGGCTGGCCGAGG AAACCCTGGATTCCCTGGCCGAGTTCTTCGAGGACCTGGCCGA CAAGCCCCTACACCTTCGAGGATTACGACGTGTCTTCGGCAGC GGCGTGCTGACAGTGAAGCTGGGCGGAGATCTGGGCACCTACG TGATCAACAAGCAGACCCCCAACAAACAGATCTGGCTATCTAG CCCCAGCAGCGGCCCCAAGAGATACGATTGGACCGGCAAGAAC TGGGTGTACAGCCACGACGGCGTGTCCCTGCATGAGCTGCTGG CTGCCGAGCTGACCAAGGCCCTGAAAACAAAGCTGGACCTGTC CAGCCTGGCCTACAGCGGCAAGGATGCC |
| SEQ ID NO: 6 | Genscript (control) optimized Nucleotide sequence encoding frataxin FIGS. 1A-1B; lane 6) | ATGTGGACACTGGGCCGGAGAGCCGTCGCTGGGCTGCTGGCA TCACCATCCCCGCACAGGCACAGACCCTGACAAGAGTCCCT CGGCCAGCAGAGCTGGCCCCACTGTGCGGGCGGAGAGGACTG CGAACCGACATCGATGCGTACTTGTACCCCAAGGCGAGCAGCTGC TCCAACCAGCGAGGGCTGAACCAGATTTGGAATGTGAAGAAA CAGTCTGTcTACCTGATGAATCTGAGAAAGAGCGGCACTCTG GGACACCCTGGCAGCCTGGACGAGACCACCTACGAGCGGCTG GCCGAGGAAACCCTGGATTCCCTGGCCGAGTTCTTTGAAGACC TGGCTGATAAGCCATACACCTTCGAAGACTATGACGTGAGCT TCGGCAGCGGCGTGCTGACAGTCAAACTGGGCGGGGACCTG GGAACATACGTGATCAACAAGCAGACTCCTAACAAGCAGATT TGGCTGTCTAGTCCCTCAAGCGGCCCTAAGAGGTACGACTGG ACAGGGAAAAACTGGGTGTATAGTCACGATGGCGTCTCACTG CATGAGCTGCTGGCCGCTGAACTGACTAAAGCCCTGAAAACT AAACTGGACCTGTCTTCCCTGGCATACTCTGGCAAGGACGC C |
| SEQ ID NO: 7 | Genscript (low CpG) nucleotide sequence encoding frataxin | ATGTGGACTCTGGGCCGGAGAGCAGTGGCAGGACTGCTGGCA AGTCCATCACCTGCTCAGGCACAGACTCTGACAAGAGTCCCA AGACCTGCAGAGCTGGCTCCACTGTGCGGGAGGCGCGGACTG |

TABLE 8-continued

| | | SEQUENCES |
|---|---|---|
| | (FIGS. 1A-1B; Lane 7) | AGAACAGACATCGATGCTACATGTACTCCTCGACGGGCAAGC TCCAACCAGCGAGGGCTGAACCAGATTTGGAATGTGAAGAA ACAGTCCGTCTACCTGATGAATCTGAGGAAGTCAGGCACCC TGGGGCACCCAGGAAGTCTGGACGAGACCACATATGAACGGC TGGCTGAGGAAACACTGGATTCTCTGGCCGAGTTCTTTGAAGA CCTGGCTGATAAGCCCTACACATTCGAAGACTATGATGTGAGC TTTGGATCCGGCGTGCTGACTGTCAAACTGGGCGGGGACCTGG GCACTTACGTGATCAACAAGCAGACCCCTAACAAGCAGATTT GGCTGTCTAGTCCTTCAAGCGGACCAAAGCGGTACGACTGGA CCGGCAAAAACTGGGTGTATTCTCACGATGGGGTCAGTCTG CATGAGCTGCTGGCCGCTGAACTGACCAAGGCCCTGAAGAC AAAACTGGACCTGTCCTCTCTGGCATATAGCGGAAAAGATG CC |
| SEQ ID NO: 8 | IDT3 optimized Nucleotide sequence encoding frataxin | ATGTGGACACTGGGAAGGCGCGCCGTGGCCGGTCTGTTGGCAT CACCATCCCCAGCCCAGGCTCAGACACTCACCCGAGTCCCA AGACCCGCAGAGCTGGCCCCCTCTGTGCGGGCGCCGAGGCC TTCGCACCGATATCGATGCTACATGCACGCCACGCAGAGCTA GCTCAAATCAGAGGGGACTCAACCAGATATGGAATGTCAAGA AGCAAAGCGTGTATCTCATGAACCTCCGGAAAAGCGGCACCC TGGGACATCCCGGGTCTCTCGACGAGACCACTTATGAAAG ACTGGCAGAGGAGACTCTTGACAGTCTGGCGGAGTTCTTCGA AGACCTCGCTGACAAGCCATATACCTTCGAAGATTACGACGTC TCCTTCGGCTCTGGGGTGCTGACTGTCAAGCTTGGCGGCGA CCTGGGGACCTACGTGATCAACAAGCAGACTCCAAACAAGCA AATCTGGCTATCTAGTCCAAGCTCCGGACCCAAGAGATACGA TTGGACAGGCAAGAATTGGGTTTACTCCCACGACGGGGTGTC CCTCCATGAGCTGCTGGCCGCAGAGCTGACGAAGGCCCTGAAG ACCAAGCTGGATCTCTCCTCCCTGGCATACAGTGGTAAGGAC GCT |
| SEQ ID NO: 9 | IDT5 optimized Nucleotide sequence encoding frataxin (FIGS. 1A-1B; Lane 3) | ATGTGGACACTGGGCCGGCGCGCCGTCGCTGGGCTGCTCGCAA GCCCCAGCCCAGCCCAAGCGCAGACTCTGACTAGGGTGCCGCG GCCTGCCGAGTTGGCCCCCCTGTGCGGTAGGAGAGGCCTGCGC ACAGACATCGATGCCACTTGCACACCCCGGCGGGCCAGCTCTA ACCAAAGGGGCCTGAATCAAATTTGGAACGTCAAAAAAACAGTC TGTATATCTGATGAATCTCCGGAAATCTGGAACGCTCGGGCAT CCCGGATCTCTTGACGAGACCACCTACGAGCGACTGGCCGAGG AAACCCTTGACAGCCTGGCAGAATTCTTTGAGGATCGGCTGA TAAAACCCTATACCTTTGAAGATTACGATGTGAGTTTTGGTAGC GGAGTACTGACTGTTAAGCTGGGCGGTGATCTCGGTACGTATG TTATCAATAAACAAACCCCCAATAAACAGATTTGGCTCTCCTC CCCATCCTCTGGGCCTAAGCGCTATGACTGGACAGGAAAGAAT TGGGTCTATTCACACGACGGAGTCAGTTTGCACGAGCTCCTCG CCGGCAGAGTTACCAAGGCCCTTAAGACTAAGCTCGACCTGTC AAGCCTCGCTTACTCTGGTAAGGACGCT |
| SEQ ID NO: 10 | Nucleotide sequence encoding frataxin (nucleic acid 22) | ATGTGGACTCTCGGGCGCCGCGCAGTAGCCGGCCTCCTGGCG TCACCCAGCCCGGCCCAGGCCCAGACCCTCACCCGGGTCCCG CGGCCGGCAGAGTTGGCCCCACTCTGCGGCCGCCGTGGCCTG CGCACCGACATCGATGCGACCTGCACGCCCCGCCGCGCAAGT TCGAACCAACGTGGCCTCAACCAGATTTGGAATGTCAAAAAGC AGAGTGTCTATTTGATGAATTTGAGGAAATCTGGAACTTTGGG CCACCCAGGCTCTCTAGATGAGACCACCTATGAAAGACTAGC AGAGGAAACGCTGGACTCTTTAGCAGAGTTTTTTGAAGACCT TGCAGACAAGCCATACACGTTTGAGGACTATGATGTCTCCT TTGGGAGTGGTGTCTTAACTGTCAAACTGGGTGGAGATCTA GGAACCTATGTGATCAACAAGCAGACGCCAAACAAGCAAAT CTGGCTATCTTCTCCATCCAGTGGACCTAAGCGTTATGACTGG ACTGGGAAAAACTGGGTGTACTCCCACGACGGCGTGTCCCT CCATGAGCTGCTGGCCGCAGAGCTCACTAAAGCCTTAAAAAC CAAACTGGACTTGTCTTCCTTGGCCTATTCCGGAAAAGATGC T |
| SEQ ID NO: 11 | IDT-1 optimized Nucleotide sequence encoding frataxin (nucleic acid 23) | ATGTGGACTCTGGGTAGGCGAGCGGTGGCCGGCCTGTTGGCAT CTCCTAGTCCTGCACAAGCTCAAACGCTGACTAGAGTCCCTGG GCCAGCAGAACTGGCGCCACTTTGCGGCCGGCGCGGTCTTCGC ACTGATATTGATGCCACTTGCACACCCCGGCGCGCCTCCAGTA ATCAGCGGGGACTTAATCAAATTTGGAATGTGAAGAAGCAG TCTGTGTATCTTATGAATCTGCGGAAGAGCGGGACCCTGGG CCACCCTGGTAGCCTTGATGAAACCACCTATGAGCGCCTGGCC GAAGAGACACTGGACAGTCTTGCCGAGTTTTTTGAGGATCTG GCCGACAAACCTTATACTTTTGAGGACTATGACGTGTCCTT TGGATCTGGTGTATTGACCGTAAAACTCGGGGGAGACCTTG GGACGTATGTAATAAATAAGCAGACCCCCAACAAGCAGATC TGGCTATCTTCTCCAAGTAGTGGTCCTAAGAGATATGATTGGAC GGGCAAGAACTGGGTCTATTCCCATGATGGCGTCTCTTTGCAT |

TABLE 8-continued

SEQUENCES

| | | |
|---|---|---|
| | | GAACTCCTTGCAGCAGAGCTGACCAAGGCCTTGAAGACCAA<br>ATTGGATCTCAGCAGCCTCGCCTATAGTGGCAAAGATGCA |
| SEQ ID NO: 12 | IDT-4 optimized Nucleotide sequence encoding frataxin (nucleic acid 26) | ATGTGGACTCTGGGCCGGCGGGCCGTAGCTGGCTTGCTGGCTA<br>GCCCAAGTCCCGCCCAGGCTCAGACTCTCACCAGGGTACCCA<br>GGCCCGCAGAGCTTGCTCCACTCTGCGGACGCAGGGGTCTGCG<br>AACCGATATCGACGCAACTTGCACGCCGCGGAGGGCCTCTTC<br>AAACCAGAGAGGACTCAATCAAATTTGGAATGTAAAGAAACA<br>GAGCGTGTATCTCATGAACCTCCGAAAGAGTGGGACTCTTGG<br>GCACCCCGGCTCCCTGGACGAGACTACTTACGAGCGCCTGGCC<br>GAAGAAACCTTGGATTCCCTGGCGGAGTTTTTTGAAGACTTG<br>GCAGACAAGCCTTATACCTTCGAGGATTACGACGTGAGTTTT<br>GGCTCTGGTGTTCTTACAGTCAAGCTCGGTGGCGACCTTGGCAC<br>TTATGTAATTAACAAGCAGACACCTAACAAGCAGATCTGGCTT<br>TCTAGTCCGTCTTCCGGTCCCAAAAGGTACGATTGGACTGGAA<br>AGAACTGGGTCTACAGTCACGACGGTGTCTCCCTGCACGAATT<br>GCTTGCGGCAGAGCTGACTAAGGCGCTCAAAACAAAACTGGAT<br>CTGTCCAGCCTTGCCTATAGCGGGAAGGACGCA |
| SEQ ID NO: 13 | Nucleotide sequence encoding chimeric AAV2.5 Vector Capsid VP1 | ATGGCTGCCGATGGTTATCTTCCAGATTGGCTCGAGGACACTC<br>TCTCTGAAGGAATAAGACAGTGGTGGAAGCTCAAACCTGGCCC<br>ACCACCACCAAAGCCCGCAGAGCGGCATAAGGACGACAGCAGG<br>GGTCTTGTGCTTCCTGGGTACAAGTACCTCGGACCCTTCAACG<br>GACTCGACAAGGGAGAGCCGGTCAACGAGGCAGACGCCGCGGC<br>CCTCGAGCACGACAAAGCCTACGACCGGCAGCTCGACAGCGGA<br>GACAACCCGTACCTCAAGTACAACCACGCCGACGCGGAGTTTC<br>AGGGAGCGCCTTAAAGAAGATACGTCTTTTGGGGGCAACCTCGG<br>ACGAGCAGTCTTCCAGGCGAAAAAGAGGGGTTCTTGAACCTCTG<br>GGCCTGGTTGAGGAACCTGTTAAGACGGCTCCGGGAAAAAAGA<br>GGCCGGTAGAGCACTCTCCTGTGGAGCCAGACTCCTCCTCGGG<br>AACCGGAAAGGCGGGCCAGCAGCCTGCAAGAAAAAGATTGAAT<br>TTTGGTCAGACTGGAGACGCAGACTCAGTACCTGACCCCCAGC<br>CTCTCGGACAGCCACCAGCAGCCCCCTCTGGTCTGGGAACTAA<br>TACGATGGCTACAGGCAGTGGCGCACCAATGGCAGACAATAAC<br>GAGGGCGCCGACGGAGTGGGTAATTCCTCGGGAAATTGGCATT<br>GCGATTCCACATGGATGGGCGACAGAGTCATCACCACCAGCAC<br>CCGAACCTGGGCCCTGCCCACCTACAACAACCACCTCTACAAA<br>CAAATTTCCAGCGCTTCAACGGGAGCCTCGAACGACAATCACT<br>ACTTTGGCTACAGCACCCCTTGGGGGTATTTTGACTTCAACAG<br>ATTCCACTGCCACTTTTCACCACGTGACTGGCAAAGACTCATC<br>AACAACAACTGGGGATTCCGACCCAAGAGACTCAACTTCAAGC<br>TCTTTAACATTCAAGTCAAAGAGGTCACGCAGAATGACGGTAC<br>GACGACGATTGCCAATAACCTTACCAGCACGGTTCAGGTGTTT<br>ACTGACTCGGAGTACCAGCTCCCGTACGTCCTCGGCTCGGCGC<br>ATCAAGGATGCCTCCCGCCGTTCCCAGCAGACGTCTTCATGGT<br>GCCACAGTATGGATACCTCACCCTGAACAACGGGAGTCAGGCA<br>GTAGGACGCTCTTCATTTTACTGCCTGGAGTACTTTCCTTCTC<br>AGATGCTGCGTACCGGAAACAACTTTACCTTCAGCTACACTTT<br>TGAGGACGTTCCTTTCCACAGCAGCTACGCTCACAGCCAGAGT<br>CTGGACCGTCTCATGAATCCTCTCATCGACCAGTACCTGTATT<br>ACTTGAGCAGAACAAACACTCCAAGTGGAACCACCACGCAGTC<br>AAGGCTTCAGTTTTCTCAGGCCGGAGCGAGTGAGTGACATTCGGAGC<br>CAGTCTAGGAACTGGCTTCCTGGACCCTGTTACCGCCAGCAGC<br>GAGTATCAAAGACATCTGCGGATAACAACAACAGTGAATACTC<br>GTGGACTGGAGCTACCAAGTACCACCTCAATGGCAGAGACTCT<br>CTGGTGAATCCGGGCCCGGCCATGGCAAGCCACAAGGACGATG<br>AAGAAAAGTTTTTTCCTCAGAGCGGGGTTCTCATCTTTGGGAA<br>GCAAGGCTCAGAGAAAACAAATGTGGACATTGAAAAGGTCATG<br>ATTACAGACGAAGAGGAAATCAGGACAACCAATCCCGTGGCTA<br>CGGAGCAGTATGGTTCTGTATCTACCAACCTCCAGAGAGGCAA<br>CAGACAAGCAGCTACCGCAGATGTCAACACACAAGGCGTTCTT<br>CCAGGCATGGTCTGGCAGGACAGAGATGTGTACCTTCAGGGGC<br>CCATCTGGGCAAAGATTCCACACACGGACGGACATTTTCACCC<br>CTCTCCCCTCATGGGTGGATTCGGACTTAAACACCCTCCTCCA<br>CAGATTCTCATCAAGAACACCCCGGTACCTGCGAATCCTTCGA<br>CCACCTTCAGTGCGGCAAAGTTTGCTTCCTTCATCACACAGTA<br>CTCCACGGGACAGGTCAGCGTGGAGATCGAGTGGGAGCTGCAG<br>AAGGAAAACAGCAAACGCTGGAATCCCGAAATTCAGTACACTT<br>CCAACTACGCCAAGTCTGTCAATGTGGACTTTACTGTGGACAA<br>TAATGGCGTGTATTCAGAGCCTCGCCCCATTGGCACCAGATAC<br>CTGACTCGTAATCTGTAA |
| SEQ ID NO: 14 | Nucleotide sequence encoding wild type AAV1 capsid (VP1) | ATGGCTGCCGATGGTTATCTTCCAGATTGGCTCGAGGACAACC<br>TCTCTGAGGGCATTCGCGAGTGGTGGGACTTGAAACCTGGAGC<br>CCCGAAGCCCAAAGCCAACCAGCAAAAGCAGGACGACGGCCGG<br>GGTCTGGTGCTTCCTGGCTACAAGTACCTCGGACCCTTCAACG<br>GACTCGACAAGGGGGAGCCCGTCAACGCGGCGGACGCAGCGGC<br>CCTCGAGCACGACAAGGCCTACGACCAGCAGCTCAAAGCGGGT |

TABLE 8-continued

| SEQUENCES |
|---|

|  |  |  |
|---|---|---|
|  |  | GACAATCCGTACCTGCGGTATAACCACGCCGACGCCGAGTTTC<br>AGGAGCGTCTGCAAGAAGATACGTCTTTTGGGGGCAACCTCGG<br>GCGAGCAGTCTTCCAGGCCAAGAAGCGGGTTCTCGAACCTCTC<br>GGTCTGGTTGAGGAAGGCGCTAAGACGGCTCCTGGAAAGAAAC<br>GTCCGGTAGAGCAGTCGCCACAAGAGCCAGACTCCTCCTCGGG<br>CATCGGCAAGACAGGCCAGCAGCCCGCTAAAAAGAGACTCAAT<br>TTTGGTCAGACTGGCGACTCAGAGTCAGTCCCCGATCCACAAC<br>CTCTCGGAGAACCTCCAGCAACCCCCGCTGCTGTGGGACCTAC<br>TACAATGGCTTCAGGCGGTGGCGCACCAATGGCAGACAATAAC<br>GAAGGCGCCGACGGAGTGGGTAATGCCTCAGGAAATTGGCATT<br>GCGATTCCACATGGCTGGGCGACAGAGTCATCACCACCAGCAC<br>CCGCACCTGGGCCTTGCCCACCTACAATAACCACCTCTACAAG<br>CAAATCTCCAGTGCTTCAACGGGGGCCAGCAACGACAACCACT<br>ACTTCGGCTACAGCACCCCCTGGGGGTATTTTGATTTCAACAG<br>ATTCCACTGCCACTTTTCACCACGTGACTGGCAGCGACTCATC<br>AACAACAATTGGGGATTCCGGCCCAAGAGACTCAACTTCAAAC<br>TCTTCAACATCCAAGTCAAGGAGGTCACGACGAATGATGGCGT<br>CACAACCATCGCTAATAACCTTACCAGCACGGTTCAAGTCTTC<br>TCGGACTCGGAGTACCAGCTTCCGTACGTCCTCGGCTCTGCGC<br>ACCAGGGCTGCCTCCCTCCGTTCCCGGCGGACGTGTTCATGAT<br>TCCGCAATACGGCTACCTGACGCTCAACAATGGCAGCCAAGCC<br>GTGGGACGTTCATCCTTTTACTGCCTGGAATATTTCCCTTCTC<br>AGATGCTGAGAACGGGCAACAACTTTACCTTCAGCTACACCTT<br>TGAGGAAGTGCCTTTCCACAGCAGCTACGCGCACAGCCAGAGC<br>CTGGACCGGCTGATGAATCCTCTCATCGACCAATACCTGTATT<br>ACCTGAACAGAACTCAAAATCAGTCCGGAAGTGCCCAAAACAA<br>GGACTTGCTGTTTAGCCGTGGGTCTCCAGCTGGCATGTCTGTT<br>CAGCCCAAAAACTGGCTACCTGGACCCTGTTATCGGCAGCAGC<br>GCGTTTCTAAAACAAAAACAGACAACAACAACAGCAATTTTAC<br>CTGGACTGGTGCTTCAAAATATAACCTCAATGGGCGTGAATCC<br>ATCATCAACCCTGGCACTGCTATGGCCTCACACAAAGACGACG<br>AAGACAAGTTCTTTCCCATGAGCGGTGTCATGATTTTTGGAAA<br>AGAGAGCGCCGGAGCTTCAAACACTGCATTGGACAATGTCATG<br>ATTACAGACGAAGAGGAAATTAAAGCCACTAACCCTGTGGCCA<br>CCGAAAGATTTGGGACCGTGGCAGTCAATTTCCAGAGCAGCAG<br>CACAGACCCTGCGACCGGAGATGTGCATGCTATGGGAGCATTA<br>CCTGGCATGGTGTGGCAAGATAGAGACGTGTACCTGCAGGGTC<br>CCATTTGGGCCAAAATTCCTCACACAGATGGACACTTTCACCC<br>GTCTCCTCTTATGGGCGGCTTTGGACTCAAGAACCCGCCTCCT<br>CAGATCCTCATCAAAAACACGCCTGTTCCTGCGAATCCTCCGG<br>CGGAGTTTTCAGCTACAAAGTTTGCTTCATTCATCACCCAATA<br>CTCCACAGGACAAGTGAGTGTGGAAATTGAATGGGAGCTGCAG<br>AAAGAAAACAGCAAGCGCTGGAATCCCGAAGTGCAGTACACAT<br>CCAATTATGCAAAATCTGCCAACGTTGATTTTACTGTGGACAA<br>CAATGGACTTTATACTGAGCCTCGCCCCATTGGCACCCGTTAC<br>CTTACCCGTCCCCTGTAA |
| SEQ ID NO: 15 | Nucleotide<br>sequence encoding<br>modified AAV1.1<br>capsid VP1 (amino<br>acid residue number<br>265 is deleted) | ATGGCTGCCGATGGTTATCTTCCAGATTGGCTCGAGGACAACC<br>TCTCTGAGGGCATTCGCGAGTGGTGGGACTTGAAACCTGGAGC<br>CCCGAAGCCCAAAGCCAACCAGCAAAAGCAGGACGACGGCCGG<br>GGTCTGGTGCTTCCTGGCTACAAGTACCTCGGACCCTTCAACG<br>GACTCGACAAGGGGGAGCCCGTCAACGCGGCGGACGCAGCGGC<br>CCTCGAGCACGACAAGGCCTACGACCAGCAGCTCAAAGCGGGT<br>GACAATCCGTACCTGCGGTATAACCACGCCGACGCCGAGTTTC<br>AGGAGCGTCTGCAAGAAGATACGTCTTTTGGGGGCAACCTCGG<br>GCGAGCAGTCTTCCAGGCCAAGAAGCGGGTTCTCGAACCTCTC<br>GGTCTGGTTGAGGAAGGCGCTAAGACGGCTCCTGGAAAGAAAC<br>GTCCGGTAGAGCAGTCGCCACAAGAGCCAGACTCCTCCTCGGG<br>CATCGGCAAGACAGGCCAGCAGCCCGCTAAAAAGAGACTCAAT<br>TTTGGTCAGACTGGCGACTCAGAGTCAGTCCCCGATCCACAAC<br>CTCTCGGAGAACCTCCAGCAACCCCCGCTGCTGTGGGACCTAC<br>TACAATGGCTTCAGGCGGTGGCGCACCAATGGCAGACAATAAC<br>GAAGGCGCCGACGGAGTGGGTAATGCCTCAGGAAATTGGCATT<br>GCGATTCCACATGGCTGGGCGACAGAGTCATCACCACCAGCAC<br>CCGCACCTGGGCCTTGCCCACCTACAATAACCACCTCTACAAG<br>CAAATCTCCAGTGCTTCAGGGGCCAGCAACGACAACCACTACT<br>TCGGCTACAGCACCCCCTGGGGGTATTTTGATTTCAACAGATT<br>CCACTGCCACTTTTCACCACGTGACTGGCAGCGACTCATCAAC<br>AACAATTGGGGATTCCGGCCCAAGAGACTCAACTTCAAACTCT<br>TCAACATCCAAGTCAAGGAGGTCACGACGAATGATGGCGTCAC<br>AACCATCGCTAATAACCTTACCAGCACGGTTCAAGTCTTCTCG<br>GACTCGGAGTACCAGCTTCCGTACGTCCTCGGCTCTGCGCACC<br>AGGGCTGCCTCCCTCCGTTCCCGGCGGACGTGTTCATGATTCC<br>GCAATACGGCTACCTGACGCTCAACAATGGCAGCCAAGCCGTG<br>GGACGTTCATCCTTTTACTGCCTGGAATATTTCCCTTCTCAGA<br>TGCTGAGAACGGGCAACAACTTTACCTTCAGCTACACCTTTGA<br>GGAAGTGCCTTTCCACAGCAGCTACGCGCACAGCCAGAGCCTG<br>GACCGGCTGATGAATCCTCTCATCGACCAATACCTGTATTACC |

TABLE 8-continued

| | | SEQUENCES |
|---|---|---|
| | | TGAACAGAACTCAAAATCAGTCCGGAAGTGCCCAAAACAAGGA<br>CTTGCTGTTTAGCCGTGGGTCTCCAGCTGGCATGTCTGTTCAG<br>CCCAAAAACTGGCTACCTGGACCCTGTTATCGGCAGCAGCGCG<br>TTTCTAAAACAAAAACAGACAACAACAACAGCAATTTTACCTG<br>GACTGGTGCTTCAAAATATAACCTCAATGGGCGTGAATCCATC<br>ATCAACCCTGGCACTGCTATGGCCTCACACAAAGACGACGAAG<br>ACAAGTTCTTTCCCATGAGCGGTGTCATGATTTTTGGAAAAGA<br>GAGCGCCGGAGCTTCAAACACTGCATTGGACAATGTCATGATT<br>ACAGACGAAGAGGAAATTAAAGCCACTAACCCTGTGGCCACCG<br>AAAGATTTGGGACCGTGGCAGTCAATTTCCAGAGCAGCAGCAC<br>AGACCCTGCGACCGGAGATGTGCATGCTATGGGAGCATTACCT<br>GGCATGGTGTGGCAAGATAGAGACGTGTACCTGCAGGGTCCCA<br>TTTGGGCCAAAATTCCTCACACAGATGGACACTTTCACCCGTC<br>TCCTCTTATGGGCGGCTTTGGACTCAAGAACCCGCCTCCTCAG<br>ATCCTCATCAAAAACACGCCTGTTCCTGCGAATCCTCCGGCTG<br>AGTTTTCAGCTACAAAGTTTGCTTCATTCATCACCCAATACTC<br>CACAGGACAAGTGAGTGTGGAAATTGAATGGGAGCTGCAGAAA<br>GAAAACAGCAAGCGCTGGAATCCCGAAGTGCAGTACACATCCA<br>ATTATGCAAATCTGCCAACGTTGATTTTACTGTGGACAACAA<br>TGGACTTTATACTGAGCCTCGCCCCATTGGCACCCGTTACCTT<br>ACCCGTCCCCTGTAA |
| SEQ ID NO: 16 | Nucleotide<br>sequence encoding<br>wildtype AAV6<br>capsid (VP1) | ATGGCTGCCGATGGTTATCTTCCAGATTGGCTCGAGGACAACC<br>TCTCTGAGGGCATTCGCGAGTGGTGGGACTTGAAACCTGGAGC<br>CCCGAAACCCAAAGCCAACCAGCAAAAGCAGGACGACGGCCGG<br>GGTCTGGTGCTTCCTGGCTACAAGTACCTCGGACCCTTCAACG<br>GACTCGACAAGGGGGAGCCCGTCAACGCGGCGGATGCAGCGGC<br>CCTCGAGCACGACAAGGCCTACGACCAGCAGCTCAAAGCGGGT<br>GACAATCCGTACCTGCGGTATAACCACGCCGACGCCGAGTTTC<br>AGGAGCGTCTGCAAGAAGATACGTCTTTTGGGGGCAACCTCGG<br>GCGAGCAGTCTTCCAGGCCAAGAAGAGGGTTCTCGAACCTTTT<br>GGTCTGGTTGAGGAAGGTGCTAAGACGGCTCCTGGAAAGAAAC<br>GTCCGGTAGAGCAGTCGCCACAAGAGCCAGACTCCTCCTCGGG<br>CATTGGCAAGACAGGCCAGCAGCCCGCTAAAAAGAGACTCAAT<br>TTTGGTCAGACTGGCGACTCAGAGTCAGTCCCCGACCCACAAC<br>CTCTCGGAGAACCTCCAGCAACCCCCGCTGCTGTGGGACCTAC<br>TACAATGGCTTCAGGCGGTGGCGCACCAATGGCAGACAATAAC<br>GAAGGCGCCGACGGAGTGGGTAATGCCTCAGGAAATTGGCATT<br>GCGATTCCACATGGCTGGGCGACAGAGTCATCACCACCAGCAC<br>CCGAACATGGGCCTTGCCCACCTATAACAACCACCTCTACAAG<br>CAAATCTCCAGTGCTTCAACGGGGCCAGCAACGACAACCACT<br>ACTTCGGCTACAGCACCCCCTGGGGGTATTTTGATTTCAACAG<br>ATTCCACTGCCATTTCTCACCACGTGACTGGCAGCGACTCATC<br>AACAACAATTGGGGATTCCGGCCCAAGAGACTCAACTTCAAGC<br>TCTTCAACATCCAAGTCAAGGAGGTCACGACGAATGATGGCGT<br>CACGACCATCGCTAATAACCTTACCAGCACGGTTCAAGTCTTC<br>TCGGACTCGGAGTACCAGTTGCCGTACGTCCTCGGCTCTGCGC<br>ACCAGGGCTGCCTCCCTCCGTTCCCGGCGGACGTGTTCATGAT<br>TCCGCAGTACGGCTACCTAACGCTCAACAATGGCAGCCAGGCA<br>GTGGGACGGTCATCCTTTTACTGCCTGGAATATTTCCCATCGC<br>AGATGCTGAGAACGGGCAATAACTTTACCTTCAGCTACACCTT<br>CGAGGACGTGCCTTTCCACAGCAGCTACGCGCACAGCCAGAGC<br>CTGGACCGGCTGATGAATCCTCTCATCGACCAGTACCTGTATT<br>ACCTGAACAGAACTCAGAATCAGTCCGGAAGTGCCCAAAACAA<br>GGACTTGCTGTTTAGCCGGGGGTCTCCAGCTGGCATGTCTGTT<br>CAGCCCAAAAACTGGCTACCTGGACCCTGTTACCGGCAGCAGC<br>GCGTTTCTAAAACAAAAACAGACAACAACAACAGCAACTTTAC<br>CTGGACTGGTGCTTCAAAATATAACCTTAATGGGCGTGAATCT<br>ATAATCAACCCTGGCACTGCTATGGCCTCACACAAAGACGACA<br>AAGACAAGTTCTTTCCCATGAGCGGTGTCATGATTTTTGGAAA<br>GGAGAGCGCCGGAGCTTCAAACACTGCATTGGACAATGTCATG<br>ATCACAGACGAAGAGGAAATCAAAGCCACTAACCCCGTGGCCA<br>CCGAAAGATTTGGGACTGTGGCAGTCAATCTCCAGAGCAGCAG<br>CACAGACCCTGCGACCGGAGATGTGCATGTTATGGGAGCCTTA<br>CCTGGAATGGTGTGGCAAGACAGAGACGTATACCTGCAGGGTC<br>CTATTTGGGCCAAAATTCCTCACACGGATGGACACTTTCACCC<br>GTCTCCTCTCATGGGCGGCTTTGGACTTAAGCACCCGCCTCCT<br>CAGATCCTCATCAAAAACACGCCTGTTCCTGCGAATCCTCCGG<br>CAGAGTTTTCGGCTACAAAGTTTGCTTCATTCATCACCCAGTA<br>TTCCACAGGACAAGTGAGCGTGGAGATTGAATGGGAGCTGCAG<br>AAAGAAAACAGCAAACGCTGGAATCCCGAAGTGCAGTATACAT<br>CTAACTATGCAAAATCTGCCAACGTTGATTTCACTGTGGACAA<br>CAATGGACTTTATACTGAGCCTCGCCCCATTGGCACCCGTTAC<br>CTCACCCGTCCCCTGTAA |
| SEQ ID NO: 17 | Nucleotide<br>sequence encoding<br>modified AAV6.1 | ATGGCTGCCGATGGTTATCTTCCAGATTGGCTCGAGGACAACC<br>TCTDGAGGGCATTCGCGAGTGGTGGGACTTGAAACCTGGAGCC<br>CCGAAACCCAAAGCCAACCAGCAAAAGCAGGACGACGGCCGGG |

TABLE 8-continued

SEQUENCES

| | | |
|---|---|---|
| | capsid VP1 (aa residue number 265 is deleted) | GTDGGTGCTTCCTGGCTACAAGTACCTCGGACCCTTCAACGGA CTCGACAAGGGGGAGCCCGTCAACGCGGCGGATGCAGCGGCCC TCGAGCACGACAAGGCCTACGACCAGCAGCTCAAAGCGGGTGA CAATCCGTACCTGCGGTATAACCACGCCGACGCCGAGTTTCAG GAGCGTCTGCAAGAAGATACGTCTTTTGGGGGCAACCTCGGGC GAGCAGTCTTCCAGGCCAAGAAGAGGGTTCTCGAACCTTTTGG TDGGTTGAGGAAGGTGCTAAGACGGCTCCTGGAAAGAAACGTC CGGTAGAGCAGTCGCCACAAGAGCCAGACTCCTCCTCGGGCAT TGGCAAGACAGGCCAGCAGCCCGCTAAAAAGAGACTCAATTTT GGTCAGACTGGCGACTCAGAGTCAGTCCCCGACCCACAACCTC TCGGAGAACCTCCAGCAACCCCCGCTGCTGTGGGACCTACTAC AATGGCTTCAGGCGGTGGCGCACCAATGGCAGACAATAACGAA GGCGCCGACGGAGTGGGTAATGCCTCAGGAAATTGGCATTGCG ATTCCACATGGCTGGGCGACAGAGTCATCACCACCAGCACCCG AACATGGGCCTTGCCCACCTATAACAACCACCTCTACAAGCAA ATCTCCAGTGCTTCAGGGGCCAGCAACGACAACCACTACTTCG GCTACAGCACCCCCTGGGGGTATTTTGATTTCAACAGATTCCA CTGCCATTTCTCACCACGTGACTGGCAGCGACTCATCAACAAC AATTGGGGATTCCGGCCCAAGAGACTCAACTTCAAGCTCTTCA ACATCCAAGTCAAGGAGGTCACGACGAATGATGGCGTCACGAC CATCGCTAATAACCTTACCAGCACGGTTCAAGTCTTCTCGGAC TCGGAGTACCAGTTGCCGTACGTCCTCGGCTCTGCGCACCAGG GCTGCCTCCCTCCGTTCCCGGCGGACGTGTTCATGATTCCGCA GTACGGCTACCTAACGCTCAACAATGGCAGCCAGGCAGTGGGA CGGTCATCCTTTTACTGCCTGGAATATTTCCCATCGCAGATGC TGAGAACGGGCAATAACTTTACCTTCAGCTACACCTTCGAGGA CGTGCCTTTCCACAGCAGCTACGCGCACAGCCAGAGCCTGGAC CGGCTGATGAATCCTCTCATCGACCAGTACCTGTATTACCTGA ACAGAACTCAGAATCAGTCCGGAAGTGCCCAAAACAAGGACTT GCTGTTTAGCCGGGGGTCTCCAGCTGGCATGTCTGTTCAGCCC AAAAACTGGCTACCTGGACCCTGTTACCGGCAGCAGCGCGTTT CTAAAACAAAAACAGACAACAACAACAGCAACTTTACCTGGAC TGGTGCTTCAAAATATAACCTTAATGGGCGTGAATCTATAATC AACCCTGGCACTGCTATGGCCTCACACAAAGACGACAAAGACA AGTTCTTTCCCATGAGCGGTGTCATGATTTTTGGAAAGGAGAG CGCCGGAGCTTCAAACACTGCATTGGACAATGTCATGATCACA GACGAAGAGGAAATCAAAGCCACTAACCCCGTGGCCACCGAAA GATTTGGGACTGTGGCAGTCAATCTCCAGAGCAGCAGCACAGA CCCTGCGACCGGAGATGTGCATGTTATGGGAGCCTTACCTGGA ATGGTGTGGCAAGACAGAGACGTATACCTGCAGGGTCCTATTT GGGCCAAAATTCCTCACACGGATGGACACTTTCACCCGTCTCC TCTCATGGGCGGCTTTGGACTTAAGCACCCGCCTCCTCAGATC CTCATCAAAAACACGCCTGTTCCTGCGAATCCTCCGGCAGAGT TTTCGGCTACAAAGTTTGCTTCATTCATCACCCAGTATTCCAC AGGACAAGTGAGCGTGGAGATTGAATGGGAGCTGCAGAAAGAA AACAGCAAACGCTGGAATCCCGAAGTGCAGTATACATCTAACT ATGCAAAATCTGCCAACGTTGATTTCACTGTGGACAACAATGG ACTTTATACTGAGCCTCGCCCCATTGGCACCCGTTACCTCACC CGTCCCCTGTAA |
| SEQ ID NO: 18 | Nucleotide sequence encoding modified AAV6.3.1 capsid VP1 (aa residue 265 deleted, Lys 531 changed to Glu) | ATGGCTGCCGATGGTTATCTTCCAGATTGGCTCGAGGACAACC TCTCTGAGGGCATTCGCGAGTGGTGGGACTTGAAACCTGGAGC CCCGAAACCCAAAGCCAACCAGCAAAAGCAGGACGACGGCCGG GGTCTGGTGCTTCCTGGCTACAAGTACCTCGGACCCTTCAACG GACTCGACAAGGGGGAGCCCGTCAACGCGGCGGATGCAGCGGC CCTCGAGCACGACAAGGCCTACGACCAGCAGCTCAAAGCGGGT GACAATCCGTACCTGCGGTATAACCACGCCGACGCCGAGTTTC AGGAGCGTCTGCAAGAAGATACGTCTTTTGGGGGCAACCTCGG GCGAGCAGTCTTCCAGGCCAAGAAGAGGGTTCTCGAACCTTTT GGTCTGGTTGAGGAAGGTGCTAAGACGGCTCCTGGAAAGAAAC GTCCGGTAGAGCAGTCGCCACAAGAGCCAGACTCCTCCTCGGG CATTGGCAAGACAGGCCAGCAGCCCGCTAAAAAGAGACTCAAT TTTGGTCAGACTGGCGACTCAGAGTCAGTCCCCGACCCACAAC CTCTCGGAGAACCTCCAGCAACCCCCGCTGCTGTGGGACCTAC TACAATGGCTTCAGGCGGTGGCGCACCAATGGCAGACAATAAC GAAGGCGCCGACGGAGTGGGTAATGCCTCAGGAAATTGGCATT GCGATTCCACATGGCTGGGCGACAGAGTCATCACCACCAGCAC CCGAACATGGGCCTTGCCCACCTATAACAACCACCTCTACAAG CAAATCTCCAGTGCTTCAGGGGCCAGCAACGACAACCACTACT TCGGCTACAGCACCCCCTGGGGGTATTTTGATTTCAACAGATT CCACTGCCATTTCTCACCACGTGACTGGCAGCGACTCATCAAC AACAATTGGGGATTCCGGCCCAAGAGACTCAACTTCAAGCTCT TCAACATCCAAGTCAAGGAGGTCACGACGAATGATGGCGTCAC GACCATCGCTAATAACCTTACCAGCACGGTTCAAGTCTTCTCG GACTCGGAGTACCAGTTGCCGTACGTCCTCGGCTCTGCGCACC AGGGCTGCCTCCCTCCGTTCCCGGCGGACGTGTTCATGATTCC GCAGTACGGCTACCTAACGCTCAACAATGGCAGCCAGGCAGTG GGACGGTCATCCTTTTACTGCCTGGAATATTTCCCATCGCAGA |

TABLE 8-continued

SEQUENCES

|  |  |  |
|---|---|---|
|  |  | TGCTGAGAACGGGCAATAACTTTACCTTCAGCTACACCTTCGA<br>GGACGTGCCTTTCCACAGCAGCTACGCGCACAGCCAGAGCCTG<br>GACCGGCTGATGAATCCTCTCATCGACCAGTACCTGTATTACC<br>TGAACAGAACTCAGAATCAGTCCGGAAGTGCCCAAAACAAGGA<br>CTTGCTGTTTAGCCGGGGGTCTCCAGCTGGCATGTCTGTTCAG<br>CCCAAAAACTGGCTACCTGGACCCTGTTACCGGCAGCAGCGCG<br>TTTCTAAAACAAAAACAGACAACAACAACAGCAACTTTACCTG<br>GACTGGTGCTTCAAAATATAACCTTAATGGGCGTGAATCTATA<br>ATCAACCCTGGCACTGCTATGGCCTCACACAAAGACGACGAAG<br>ACAAGTTCTTTCCCATGAGCGGTGTCATGATTTTTGGAAAGGA<br>GAGCGCCGGAGCTTCAAACACTGCATTGGACAATGTCATGATC<br>ACAGACGAAGAGGAAATCAAAGCCACTAACCCCGTGGCCACCG<br>AAAGATTTGGGACTGTGGCAGTCAATCTCCAGAGCAGCAGCAC<br>AGACCCTGCGACCGGAGATGTGCATGTTATGGGAGCCTTACCT<br>GGAATGGTGTGGCAAGACAGAGACGTATACCTGCAGGGTCCTA<br>TTTGGGCCAAAATTCCTCACACGGATGGACACTTTCACCCGTC<br>TCCTCTCATGGGCGGCTTTGGACTTAAGCACCCGCCTCCTCAG<br>ATCCTCATCAAAAACACGCCTGTTCCTGCGAATCCTCCGGCAG<br>AGTTTTCGGCTACAAAGTTTGCTTCATTCATCACCCAGTATTC<br>CACAGGACAAGTGAGCGTGGAGATTGAATGGGAGCTGCAGAAA<br>GAAAACAGCAAACGCTGGAATCCCGAAGTGCAGTATACATCTA<br>ACTATGCAAATCTGCCAACGTTGATTTCACTGTGGACAACAA<br>TGGACTTTATACTGAGCCTCGCCCCATTGGCACCCGTTACCTC<br>ACCCGTCCCCTGTAA |
| SEQ ID NO: 19 | Nucleotide<br>sequence encoding<br>human wild type<br>frataxin (WT FXN)<br>for cloning into<br>pTRs-KS-CBh-<br>EGFP-BGH scAAV<br>vector<br>AgeI site in bold;<br>AvrII <u>underlined</u>;<br>CSS <u>double<br>underlined</u>;<br>SpeI in bold<br>underlined;<br>bGHpolyA in *italics*;<br>MluI site in *bold<br>italics*<br>(See FIG. 2A) | TAGAAGACCGGTCGCCACCatgtggactctcgggcgccgcgca<br>gtagccggcctcctggcgtcacccagcccagcccaggcccaga<br>ccctcacccgggtcccgcggccggcagagttggccccactctg<br>cggccgccgtggcctgcgcaccgacatcgatgcgacctgcacg<br>ccccgccgcgcaagttcgaaccaacgtggcctcaaccagatt<br>ggaatgtcaaaaagcagagtgtctatttgatgaatttgaggaa<br>atctggaactttgggccaccaggctctctagatgagaccacc<br>tatgaaagactagcagaggaaacgctggactcttagcagagt<br>tttttgaagaccttgcagacaagccatacacgtttgaggacta<br>tgatgtctcctttgggagtggtgtcttaactgtcaaactgggt<br>ggagatctaggaacctatgtgtcaacaagcagacgccaaaca<br>agcaaatctggctatcttctccatccagtggacctaagcgtta<br>tgactggactgggaaaaactgggtgtactcccacgacggcgtg<br>tccctccatgagctgctggccgcagagctcactaaagccttaa<br>aaaccaaactggacttgtctcttcctggccattccggaaaaga<br>tgcttgaCGAGCGGCCGCT<u>CCTAGGA</u>GCAGTATCGATC<u>CCAGC<br>CCACTTTTCCCCAATACGACTAGTACTCGACTGTGCCTTCTAG</u><br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGGACGCGTCTTAAG* |
| SEQ ID NO: 20 | IDT1 Codon<br>optimized nucleotide<br>sequence encoding<br>FXN for cloning into<br>pTRs-KS-CBh-<br>EGFP-BGH scAAV<br>vector<br>AgeI site in bold;<br>AvrII <u>underlined</u>;<br>CSS <u>double<br>underlined</u>;<br>SpeI in bold<br>underlined;<br>bGHpolyA in *italics*;<br>MluI site in *bold<br>italics*<br>(See FIG. 2B) | TAGAAGACCGGTCGCCACCatgtggactctgggtaggcgagcg<br>gtggccggcctgttggcatctcctagtcctgcacaagctcaaa<br>cgctgactagagtccctcggccagcagaactggcgccacttg<br>cggccggcgcggtcttcgcactgatattgatgccacttgcaca<br>ccccggcgcgcctccagtaatcagcggggacttaatcaaattt<br>ggaatgtgaagaagcagtctgtgtatcttatgaatctgcggaa<br>gagcgggaccctgggccaccctggtagccttgatgaaaccacc<br>tatgagcgcctggccgaagagacactggacagtcttgccgagt<br>tttttgaggatctggccgacaaaccttatacttttgaggacta<br>tgacgtgtcctttggatctggtgtattgaccgtaaaactcggg<br>ggagaccttgggacgtatgtaataaataagcagaccccaaaca<br>agcagatctggctcagctctccaagtagtggtcctaagagata<br>tgattggacgggcaagaactgggtctattcccatgatggcgtc<br>tctttgcatgaactccttgcagcagagctgaccaaggccttga<br>agaccaaattggatctcagcagcctcgcctatagtggcaaaga<br>tgcatagCGAGCGGCCGCT<u>CCTAGGA</u>GCAGTATCGAT<u>CCCAGC<br>CCACTTTTCCCCAAT</u>ACGACTAGTACTCGACTGTGCCTTCTAG<br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGGACGCGTCTTAAG* |
| SEQ ID NO: 21 | Codon optimized<br>nucleotide sequence<br>encoding FXN IDT3<br>(low expresser) for<br>cloning into pTRs- | TAGAAGACCGGTCGCCACCatgtggacactgggaaggcgcgcc<br>gtggccggtctgttggcataccatcccagcccaggctcaga<br>cactcacccgagtcccaagacccgcagagctggcccctctgtg<br>cgggcgccgaggccttcgcaccgatatcgatgctacatgcacg<br>ccacgcagagctagctcaaatcagagggggactcaaccagatat |

TABLE 8-continued

SEQUENCES

| | | |
|---|---|---|
| | KS-CBh-EGFP-BGH scAAV vector<br>AgeI site in bold;<br>AvrII underlined;<br>CSS double underlined;<br>SpeI in bold underlined;<br>bGHpolyA in *italics*;<br>MluI site in *bold italics*<br>(See FIG. 2C) | ggaatgtcaagaagcaaagcgtgtatctcatgaacctccggaa<br>aagcggcaccctgggacatcccgggtctctcgacgagaccact<br>tatgaaagactggcagaggagactcttgacagtctggcggagt<br>tcttcgaagacctcgctgacaagccatataccttcgaagatta<br>cgacgtctccttcggctctggggtgctgactgtcaagcttggc<br>ggcgacctggggacctacgtgatcaacaagcagactccaaaca<br>agcaaatctggctcagcagtccaagctccggacccaagagata<br>cgattggacaggcaagaatttgggtttactcccacgacgggtg<br>tccctccatgagctgctggccgctgagctgacgaaggccctga<br>agaccaagctggatctctcctccctggcatacagtggtaagga<br>cgcttgaCGAGCGGCCGCT<u>CCTAGGA</u>GCAGTATCGAT<u>CCCAGC</u><br><u>CCACTTTTCCCCAA</u>TACGACTAGTACTCGACTGTGCCTTCTAG<br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGGACGCGTCTTAAG* |
| SEQ ID NO: 22 | Codon-optimized nucleotide sequence encoding FXN IDT4 for cloning into pTRs-KS-CBh-EGFP-BGH scAAV vector<br>AgeI site in bold;<br>AvrII underlined;<br>CSS double underlined;<br>SpeI in bold underlined;<br>bGHpolyA in *italics*;<br>MluI site in *bold italics*<br>(See FIG. 2D) | TAGAAGACCGGTCGCCACCatgtggactctgggccggcgggcc<br>gtagctggcttgctggctagcccaagtcccgcccaggctcaga<br>ctctcaccagggtacccaggcccgcagagcttgctccactctg<br>cggacgcagggtctgcgaaccgatatcgacgcaacttgcacg<br>ccgcggagggcctcttcaaaccagagaggactcaatcaaattt<br>ggaatgtaaagaaacagagcgtgtatctcatgaacctccgaaa<br>gagtgggactcttgggcaccccggctccctggacgagactact<br>tacgagcgcctggccggcgaagaaaccttggattccctggcggagt<br>ttttgaagacttggcagacaagccttataccttcgaggatta<br>cgacgtgagttttggctctggtgttcttacagtcaagctcggt<br>ggcgaccttggcacttatgtaattaacaagcagacacctaaca<br>agcagatctggctttctagtccgtcttccggtcccaaaaggta<br>cgattggactggaaagaactgggtctacagtcacgacggtgtc<br>tccctgcacgaattgcttgcggctgagctgactaaggcgctca<br>aaacaaaactggatctgtccagccttgcctatagcgggaagga<br>cgcatgaCGAGCGGCCGCT<u>CCTAGGA</u>GCAGTATCGAT<u>CCCAGC</u><br><u>CCACTTTTCCCCAA</u>TACGACTAGTACTCGACTGTGCCTTCTAG<br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGGACGCGTCTTAAG* |
| SEQ ID NO: 23 | Codon-optimized nucleotide sequence encoding FXN GenScript for cloning into pTRs-KS-CBh-EGFP-BGH scAAV vector<br>AgeI site in bold;<br>AvrII underlined;<br>CSS double underlined;<br>SpeI in bold underlined;<br>bGHpolyA in *italics*;<br>MluI site in *bold italics*<br>(See FIG. 2E) | TAGAAGACCGGTCGCCACCatgtggacactgggccggagagcc<br>gtcgctgggctgctggcatcaccatccccgcacaggcacaga<br>ccctgacaagagtccctcggccagcagagctggccccactgtg<br>cgggcggagaggactgcgaaccgacatcgatgctacttgtacc<br>ccaaggcgcaagctccaacagcgagggctgaaccagattt<br>ggaatgtgaagaaacagtctgtctacctgatgaatctgagaaa<br>gagcggcactctgggacaccctggcagcctggacgagaccacc<br>tacgagcggctggccgaggaaaccctggattccctggccgagt<br>tcttttgaagacctggctgataagccatacaccttcgaagacta<br>tgacgtgagcttcggcagcggcgtgctgacagtcaaactgggc<br>ggggacctgggaacatacgtgatcaacaagcagactcctaaca<br>agcagatttggctgtctagtccctcaagcggccctaagaggta<br>cgactggacagggaaaaactgggtgtatagtcacgatgcgtc<br>tcactgcatgagctgctggccgctgaactgactaaagccctga<br>aaactaaactggacctgtcttccctggcatactctggcaagga<br>cgcctgaCGAGCGGCCGCT<u>CCTAGGA</u>GCAGTATCGAT<u>CCCAGC</u><br><u>CCACTTTTCCCCAA</u>TACGACTAGTACTCGACTGTGCCTTCTAG<br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGGACGCGTCTTAAG* |
| SEQ ID NO: 24 | Codon-optimized nucleotide sequence encoding FXN GenScript (low CpG) for cloning into pTRs-KS-CBh-EGFP-BGH scAAV vector<br>AgeI site in bold;<br>AvrII underlined;<br>CSS double | TAGAAGACCGGTCGCCACCatgtggactctgggccggagagca<br>gtggcaggactgctggcaagtccatcacctgctcaggcacaga<br>ctctgacaagagtcccaagacctgcagagctggctccactgtg<br>cgggaggcgcggactgagaacagacatcgatgctacatgtact<br>cctcgacgggcaagctccaaccagcgagggctgaaccagattt<br>ggaatgtgaagaaacagtccgtctacctgatgaatctgagaaa<br>gtcaggcaccctggggcacccaggaagtctggacgagaccaca<br>tatgaacggctggctgaggaaacactggattctctggccgagt<br>tctttgaagacctggctgataagccctacacattcgaagacta<br>tgatgtgagctttggatccggcgtgctgactgtcaaactgggc<br>ggggacctgggcacttacgtgatcaacaagcagaccctaaca |

TABLE 8-continued

SEQUENCES

| | | |
|---|---|---|
| | underlined;<br>SpeI in bold<br>underlined;<br>bGHpolyA in *italics*;<br>MluI site in **bold<br>*italics*<br>(See FIG. 2F) | agcagatttggctgtctagtccttcaagcggaccaaagcggta<br>cgactggaccggcaaaaactgggtgtattctcacgatggggtc<br>agtctgcatgagctgctggccgctgaactgaccaaggccctga<br>agacaaaactggacctgtcctctctggcatatagcggaaaaga<br>tgcctgaCGAGCGGCCGCT<u>CCTAGGA</u>GCAGTATCGAT<u>CCCAGC<br>CCACTTTTCCCCAA</u>TACACTAGT**ACTCGACTGTGCCTTCTAG<br>*TTGCCAGCCATCTGTTGTTTGCCCCTCCCCCGTGCCTTCCTTG<br>ACCCTGGAAGGTGCCACTCCCACTGTCCTTTCCTAATAAAATG<br>AGGAAATTGCATCGCATTGTCTGAGTAGGTGTCATTCTATTCT<br>GGGGGGTGGGGTGGGGCAGGACAGCAAGGGGGAGGATTGGGAA<br>GACAACAGCAGGCATGCTGGGGATGCGGTGGGCTCTATGGCTT<br>CTGAGGCGGAAAGAACCAGCTTTGG**ACGCGT*CTTAAG |
| SEQ ID NO: 25 | Nucleic acid<br>sequence encoding<br>collagen stabilizing<br>sequence (CSS) | CCCAGCCCACTTTTCCCCAA |
| SEQ ID NO: 26 | Nucleic acid<br>sequence of CBh<br>promoter | tacataacttacggtaaatggcccgcctggctgaccgcccaac<br>gaccccgcccattgacgtcaatagtaacgccaatagggactt<br>tccattgacgtcaatgggtggagtatttacggtaaactgccca<br>cttggcagtacatcaagtgtatcatatgccaagtacgcccccct<br>attgacgtcaatgacggtaaatggcccgcctggcattgtgccc<br>agtacatgaccttatgggactttcctacttggcagtacatcta<br>cgtattagtcatcgctattaccatggtcgaggtgagccccacg<br>ttctgcttcactctccccatctccccccctccccaccccaa<br>ttttgtatttatttattttttaattatttttgtgcagcgatggg<br>ggcggggggggggggggcgcgcgccaggcggggcggggcgg<br>ggcgaggggcgggcgggcgaggcggagaggtgcggcggcag<br>ccaatcagagcggcgcgctccgaaagtttccttttatggcgag<br>gcggcggcggcggcggccctataaaaagcgaagcgcgcggcgg<br>gcgggagtcgctgcgacgctgccttcgccccgtgccccgctcc<br>gccgccgcctcgcgccgcccgcccggctctgactgaccgcgt<br>tactcccacaggtgagcgggcgggacggcccttctcctccggg<br>ctgtaattagctgagcaagaggtaagggtttaagggatggttg<br>gttggtggggtattaatgtttaattacctggagcacctgcctg<br>aaatcacttttttttcaggttgga |
| SEQ ID NO: 27 | Nucleic acid<br>sequence of<br>bGHpoly A signal<br>sequence | CTCGACTGTGCCTTCTAGTTGCCAGCCATCTGTTGTTTGCCCC<br>TCCCCCGTGCCTTCCTTGACCCTGGAAGGTGCCACTCCCACTG<br>TCCTTTCCTAATAAAATGAGGAAATTGCATCGCATTGTCTGAG<br>TAGGTGTCATTCTATTCTGGGGGGTGGGGTGGGGCAGGACAGC<br>AAGGGGGAGGATTGGGAAGACAACAGCAGGCATGCTGGGGATG<br>CGGTGGGCTCTATGGCTTCTGAGGCGGAAAGAACCAGCT |
| SEQ ID NO: 28 | Nucleotide<br>sequence encoding<br>AAV2i8 capsid<br>(VP1) | atggctgccgatggttatcttccagattggctcgaggacactc<br>tctctgaaggaataagacagtggtggaagctcaaacctggccc<br>accaccaccaaagcccgcagagcggcataaggacgacagcagg<br>ggtcttgtgcttcctgggtacaagtacctcggaccccttcaacg<br>gactcgacaagggagagccggtcaacgaggcagacgccgcggc<br>cctcgagcacgacaaagcctacgaccggcagctcgacagcgga<br>gacaacccgtacctcaagtacaaccacgccgacgcggagtttc<br>aggagcgccttaaagaagatacgtcttttgggggcaacctcgg<br>acgagcagtcttccaggcgaaaaagagggttcttgaacctctg<br>ggcctggttgaggaacctgttaagacggctccgggaaaaaaga<br>ggccggtagagcactctcctgtggagccagactcctcctcggg<br>aaccggaaaggcgggccagcagcctgcaagaaaaagattgaat<br>tttggtcagactggagacgcagactcagtacctgaccccccagc<br>ctctcggacagccaccagcagcccctctggtctgggaactaa<br>tacgatggctacaggcagtggcgcaccaatggcagacaataac<br>gagggcgccgacggagtgggtaattcctcgggaaattggcatt<br>gcgattccacatggatgggcgacagagtcatcaccaccagcac<br>ccgaacctgggccctgcccacctacaacaaccacctctacaaa<br>caaatttccagccaatcaggagcctcgaacgacaatcactact<br>ttggctacagcaccccttggggtatttgacttcaacagatt<br>ccactgccacttttcaccacgtgactggcaaagactcatcaac<br>aacaactgggattccgacccaagagactcaacttcaagctctt<br>taacattcaagtcaaagaggtcacgcagaatgacggtacgac<br>gacgattgccaataaccttaccagcacggttcaggtgtttact<br>gactcggagtaccagctcccgtacgtcctcggctcggcgcatc<br>aaggatgcctcccgccgttcccagcagacgtcttcatggtgcc<br>acagtatggatacctcaccctgaacaacgggagtcaggcagta<br>ggacgctcttcattttactgcctggagtactttcttctcaga<br>tgctgcgtaccggaaacaactttaccttcagctacactttga<br>ggacgttccttccacagcagcta<br>cgctcacagccagagtctggaccgtctcatgaatcctctcatc<br>gaccagtacctgtattacttgagcagaacaaacactccaagtg<br>gaaccaccacgcagtcaaggcttcagttttctgtggccggacc |

TABLE 8-continued

SEQUENCES

|  |  |  |
|---|---|---|
|  |  | cagtaacatggctgtccagggaaggaactggcttcctggaccc<br>tgttaccgccagcagcgagtatcaaagacatctgcggataaca<br>acaacagtgaatttgcttggactggagctaccaagtaccacct<br>caatggcagagactctctggtgaatccgggcccggccatggca<br>agccacaaggacgatgaagaaaagttttttcctcagagcgggg<br>ttctcatctttgggaagcaaggctcagagaaaacaaatgtgga<br>cattgaaaaggtcatgattacagacgaagaggaaatcaggaca<br>accaatcccgtggctacggagcagtatggttctgtatctacca<br>acctccagcaacagaacacagcaccagctaccgcagatgtcaa<br>cacacaaggcgttcttccaggcatggtctggcaggacagagat<br>gtgtaccttcaggggcccatctgggcaaagattccacacacgg<br>acggacattttcacccctctcccctcatgggtggattcggact<br>taaacaccctcctccacagattctcatcaagaacacccccgta<br>cctgcgaatccttcgaccaccttcagtgcggcaaagtttgctt<br>ccttcatcacacagtactccacgggacaggtcagcgtggagat<br>cgagtgggagctgcagaaggaaaacagcaaacgctggaatccc<br>gaaattcagtacacttccaactacaacaagtctgttaatgtgg<br>actttactgtggacactaatggcgtgtattcagagcctcgccc<br>cattggcaccagatacctgactcgtaatctgtaa |
| SEQ ID NO: 29 | Amino acid<br>sequence of AAV2i8<br>capsid (VP1) | MAADGYLPDWLEDTLSEGIRQWWKLKPGPPPPKPAERHKDDSR<br>GLVLPGYKYLGPFNGLDKGEPVNEADAAALEHDKAYDRQLDSG<br>DNPYLKYNHADAEFQERLKEDTSFGGNLGRAVFQAKKRVLEPL<br>GLVSEPVKTAPGKKRPVEHSPVEPDSSSGTGKAGQQPARKRLN<br>FGQTGDADSVPDPQPLGQPPAAPSGLGTNTMATGSGAPMADNN<br>EGADGVGNSSGNWHCDSTWMGDRVITTSTRTWALPTYNNHLYK<br>QISSQSGASNDNHYFGYSTPWGYFDENRFHCHFSPRDWQRLIN<br>NNWGFRPKRLNFKLFNIQVKEVTQNDGITTIANNLTSTVQVFT<br>DSEYQLPYVLGSAHQGCLPPFPADVFMVPQYGYLTLNNGSQAV<br>GRSSFYCLEYFPSQMLRTGNNFTFSYTFEDVPFHSSYAHSQSL<br>DRLMNPLIDQYLYYLSRTNTPSGTTTQSRLQFSVAGPSNMAVQ<br>GRNWLPGPCYRQQRVSKTSADNNNSEFAWTGATKYHLNGRDSL<br>VNPGPAMASHKDDEEKFFPQSGVLIFGKQGSEKTNVDIEKVMI<br>TDEEEIRTTNPVATEQYGSVSTNLQQQNTAPATADVNTQGVLP<br>GMVWQDRDVYLQGPIWAKIPHTDGHFHPSPLMGGFGLKHPPPQ<br>ILIKNTPVPANPSTTFSAAKFASFITQYSTGQVSVEIEWELQK<br>ENSKRWNPEIQYTSNYNKSVNVDFTVDTNGVYSEPRPIGTRYL<br>TRNL |
| SEQ ID NO: 30 | Nucleic acid<br>encoding AAV2-TT<br>capsid (VP1)<br>(nucleotides that<br>differ from WT AAV2<br>are underlined) | ATGGCTGCCGATGGTTATCTTCCAGATTGGCTCGAGGACACTC<br>TCTCTGAAGGAATAAGACAGTGGTGGAAGCTCAAACCTGGCCC<br>ACCACCACCAAAGCCCGCAGAGCGGCATAAGGACGACAGCAGG<br>GGTCTTGTGCTTCCTGGGTACAAGTACCTCGGACCCTTCAACG<br>GACTCGACAAGGGAGAGCCGGTCAACGAGGCAGACGCCGCGGC<br>CCTCGAGCACGACAAAGCCTACGACCGGCAGCTCGACAGCGGA<br>GACAACCCGTACCTCAAGTACAACCACGCCGACGCGGAGTTTC<br>AGGAGCGCCTTAAAGAAGATACGTCTTTTGGGGGCAACCTCGG<br>ACGAGCAGTCTTCCAGGCGAAAAAGAGG<u>A</u>TTCTTGAACCTCTG<br>GGCCTGGTTGAGGAACCTGTTAAGACGGCTCCGGGAAAAAAGA<br>GGCCGGTAGAGCACTCTCCTG<u>C</u>GGAGCCAGACTCCTCCTCGGG<br>AACCGGAAAG<u>T</u>CGGGCCAGCAGCCTGCAAGAAAAAGATTGAAT<br>TTTGGTCAGACTGGAGACGCAGACTCAGTACCTGACCCCCAGC<br>CTCTCGGACAGCCACCAGCAGCCCCCTCTGGTCTGGGAACTAA<br>TACGATGGCT<u>TT</u>CAGGCAGTGGCGCACCAATGGCAGACAATAAC<br>GAGGGCGCCGACGGAGTGGGTAATTCCTCGGGAAATTGGCATT<br>GCGATTCCACATGGATGGGCGACAGAGTCATCACCACCAGCAC<br>CCGAACCTGGGCCCTGCCCACCTACAACAACCACCTCTACAAA<br>CAAATTTCCAGCCAATCAGGAGCCTCGAACGACAATCACTACT<br>TTGGCTACAGCACCCCTTGGGGGTATTTTGACTTCAACAGATT<br>CCACTGCCACTTTTCACCACGTGACTGGCAAAGACTCATCAAC<br>AACAACTGGGGATTCCGACCCAAGAGACTCA<u>G</u>CTTCAAGCTCT<br>TTAACATTCAAGTCAAAGAGGTCACGCAGAATGACGGTACGAC<br>GACGATTGCCAATAACCTTACCAGCACGGTTCAGGTGTTTACT<br>GACTCGGAGTACCAGCTCCCGTACGTCCTCGGCTCGGCGCATC<br>AAGGATGCCTCCCGCCGTTCCCAGCAGACGTCTTCATGGTGCC<br>ACAGTATGGATACCTCACCCTGAACAACGGGAGTCAGGCAGTA<br>GGACGCTCTTCATTTTACTGCCTGGAGTACTTTCCTTCTCAGA<br>TGCTGCGTACCGGAAACAACTTTACCTTCAGCTACACTTTTGA<br>GGACGTTCCTTTCCACAGCAGCTACGCTCACAGCCAGAGTCTG<br>GACCGTCTCATGAATCCTCTCATCGACCAGTACCTGTATTACT<br>TGAGCAGAACAAACACTCCAAGTGGAACCACCACG<u>AT</u>GTCAAG<br>GCTTCAGTTTTCTCAGGCCGGAGCGAGTGACATTCGGGACCAG<br>TCTAGGAACTGGCTTCCTGGACCCTGTTACCGCCAGCAGCGAA<br>TATCAAAGACAG<u>C</u>TGCGGATAACAACAACAGTGA<u>TT</u>ACTCGTG<br>GACTGGAGCTACCAAGTACCACCTCAATGGCAGAGACTCTCTG<br>GTGAATCCGGGCCCGGCCATGGCAAGCCACAAGGACGATGAAG<br>AAAAGT<u>A</u>TTTTCCTCAGAGCGGGGTTCTCATCTTTGGGAAGCA<br>AG<u>A</u>CTCAGG<u>GA</u>AAAACAAATGTGGACATTGAAAAGGTCATGATT |

TABLE 8-continued

| | | SEQUENCES |
|---|---|---|
| | | ACAGACGAAGAGGAAATCAGGACAACCAATCCCGTGGCTACGG<br>AGCAGTATGGTTCTGTATCTACCAACCTCCAGAGCGGCAACAC<br>ACAAGCAGCTACC<u>T</u>CAGATGTCAACACACAAGGCGTTCTTCCA<br>GGCATGGTCTGGCAGGACAGAGATGTGTACCTTCAGGGGCCCA<br>TCTGGGCAAAGATTCCACACACGGACGGACATTTTCACCCCTC<br>TCCCCTCATGGGTGGATTCGGACTTAAACACCCTCCTCCACAG<br>ATTCTCATCAAGAACACCCCGGTACCTGCGAATCCTTCGACCA<br>CCTTCAGTGCGGCAAAGTTTGCTTCCTTCATCACACAGTACTC<br>CACGGGACAGGTCAGCGTGGAGATCGAGTGGGAGCTGCAGAAG<br>GAAAACAGCAAACGCTGGAATCCCGAAATTCAGTACACTTCCA<br>ACTACAACAAGTCTGTTAATGTGGACTTTACTGTGGACACTAA<br>TGGCGTGTATTCAGAGCCTCGCCCCATTGGCACCAGATACCTG<br>ACTCGTAATCTGTAA |
| SEQ ID NO: 31 | Amino acid sequence of AAV2-TT capsid (VP1) | MAADGYLPDWLEDTLSEGIRQWWKLKPGPPPPKPAERHKDDSR<br>GLVLPGYKYLGPFNGLDKGEPVNEADAAALEHDKAYDRQLDSG<br>DNPYLKYNHADAEFQERLKEDTSFGGNLGRAVFQAKKRILEPL<br>GLVEEPVKTAPGKKRPVEHSPAEPDSSSGTGKSGQQPARKRLN<br>FGQTGDADSVPDPQPLGQPPAAPSGLGTNTMASGSGAPMADNN<br>EGADGVGNSSGNWHCDSTWMGDRVITTSTRTWALPTYNNHLYK<br>QISSQSGASNDNHYFGYSTPWGYFDFNRFHCHFSPRDWQRLIN<br>NNWGFRPKRLSFKLFNIQVKEVTQNDGITTIANNLTSTVQVFT<br>DSEYQLPYVLGSAHQGCLPPFPADVFMVPQYGYLTLNNGSQAV<br>GRSSFYCLEYFPSQMLRTGNNFTFSYTFEDVPFHSSYAHSQSL<br>DRLMNPLIDQYLYYLSRTNTPSGTTTMSRLQFSQAGASDIRDQ<br>SRNWLPGPCYRQQRVSKTAADNNNSDYSWTGATKYHLNGRDSL<br>VNPGPAMASHKDDEEKYFPQSGVLIFGKQDSGKTNVDIEKVMI<br>TDEEEIRTTNPVATEQYGSVSTNLQSGNTQAATSDVNTQGVLP<br>GMVWQDRDVYLQGPIWAKIPHTDGHFHPSPLMGGFGLKHPPPQ<br>ILIKNTPVPANPSTTFSAAKFASFITQYSTGQVSVEIEWELQK<br>ENSKRWNPEIQYTSNYNKSVNVDFTVDTNGVYSEPRPIGTRYL<br>TRNL |
| SEQ ID NO: 32 | Nucleic acid encoding AAV2-TT-S312N capsid (VP1) (nucleotides that differ from WT AAV2 are underlined) | ATGGCTGCCGATGGTTATCTTCCAGATTGGCTCGAGGACACTC<br>TCTCTGAAGGAATAAGACAGTGGTGGAAGCTCAAACCTGGCCC<br>ACCACCACCAAAGCCCGCAGAGCGGCATAAGGACGACAGCAGG<br>GGTCTTGTGCTTCCTGGGTACAAGTACCTCGGACCCTTCAACG<br>GACTCGACAAGGGAGAGCCGGTCAACGAGGCAGACGCCGCGGC<br>CCTCGAGCACGACAAGGCCTACGACCGGCAGCTCGACAGCGGA<br>GACAACCCGTACCTCAAGTACAACCACGCCGACGCGGAGTTTC<br>AGGAGCGCCTTAAAGAAGATACGTCTTTTGGGGGCAACCTCGG<br>ACGAGCAGTCTTCCAGGCGAAAAAGAGG<u>A</u>TTCTTGAACCTCTG<br>GGCCTGGTTGAGGAACCTGTTAAGACGGCTCCGGGAAAAAAGA<br>GGCCGGTAGAGCACTCTCCTG<u>C</u>GGAGCCAGACTCCTCCTCGGG<br>AACCGGAAAG<u>T</u>CGGGCCAGCAGCCTGCAAGAAAAAGATTGAAT<br>TTTGGTCAGACTGGAGACGCAGACTCAGTACCTGACCCCCAGC<br>CTCTCGGACAGCCACCAGCAGCCCCCTCTGGTCTGGGAACTAA<br>TACGATGGC<u>TT</u>CAGGCAGTGGCGCACCAATGGCAGACAATAAC<br>GAGGGCGCCGACGGAGTGGGTAATTCCTCGGGAAATTGGCATT<br>GCGATTCCACATGGATGGGCGACAGAGTCATCACCACCAGCAC<br>CCGAACCTGGGCCCTGCCCACCTACAACAACCACCTCTACAAA<br>CAAATTTCCAGCCAATCAGGAGCCTCGAACGACAATCACTACT<br>TTGGCTACAGCACCCCTTGGGGGTATTTTGACTTCAACAGATT<br>CCACTGCCACTTTTCACCACGTGACTGGCAAAGACTCATCAAC<br>AACAACTGGGGATTCCGACCCAAGAGACTCAACTTCAAGCTCT<br>TTAACATTCAAGTCAAAGAGGTCACGCAGAATGACGGTACGAC<br>GACGATTGCCAATAACCTTACCAGCACGGTTCAGGTGTTTACT<br>GACTCGGAGTACCAGCTCCCGTACGTCCTCGGCTCGGCGCATC<br>AAGGATGCCTCCCGCCGTTCCCAGCAGACGTCTTCATGGTGCC<br>ACAGTATGGATACCTCACCCTGAACAACGGGAGTCAGGCAGTA<br>GGACGCTCTTCATTTTACTGCCTGGAGTACTTTCCTTCTCAGA<br>TGCTGCGTACCGGAAACAACTTTACCTTCAGCTACACTTTTGA<br>GGACGTTCCTTTCCACAGCAGCTACGCTCACAGCCAGAGTCTG<br>GACCGTCTCATGAATCCTCTCATCGACCAGTACCTGTATTACT<br>TGAGCAGAACAAACACTCCAAGTGGAACCACCACG<u>A</u>TGTCAAG<br>GCTTCAGTTTTCTCAGGCCGGAGCGAGTGACATTCGGGACCAG<br>TCTAGGAACTGGCTTCCTGGACCCTGTTACCGCCAGCAGCGAG<br>TATCAAAGACA<u>G</u>CTGCGGATAACAACAACAGTGA<u>TT</u>ACTCGTG<br>GACTGGAGCTACCAAGTACCACCTCAATGGCAGAGACTCTCTG<br>GTGAATCCGGGCCCGGCCATGGCAAGCCACAAGGACGATGAAG<br>AAAAGTA<u>T</u>TTTCCTCAGAGCGGGGTTCTCATCTTTGGGAAGCA<br>AG<u>A</u>CT<u>C</u>AGG<u>A</u>AAAACAAATGTGGACATTGAAAAGGTCATGATT<br>ACAGACGAAGAGGAAATCAGGACAACCAATCCCGTGGCTACGG<br>AGCAGTATGGTCTGTATCTACCAACCTCCAGAGC<u>C</u>GGCAACAC<br>ACAAGCAGCTACC<u>T</u>CAGATGTCAACACACAAGGCGTTCTTCCA<br>GGCATGGTCTGGCAGGACAGAGATGTGTACCTTCAGGGGCCCA<br>TCTGGGCAAAGATTCCACACACGGACGGACATTTTCACCCCTC<br>TCCCCTCATGGGTGGATTCGGACTTAAACACCCTCCTCCACAG |

TABLE 8-continued

| SEQUENCES | | |
|---|---|---|
| | | ATTCTCATCAAGAACACCCCGGTACCTGCGAATCCTTCGACCA<br>CCTTCAGTGCGGCAAAGTTTGCTTCCTTCATCACACAGTACTC<br>CACGGGACAGGTCAGCGTGGAGATCGAGTGGGAGCTGCAGAAG<br>GAAAACAGCAAACGCTGGAATCCCGAAATTCAGTACACTTCCA<br>ACTACAACAAGTCTGTTAATGTGGACTTTACTGTGGACACTAA<br>TGGCGTGTATTCAGAGCCTCGCCCCATTGGCACCAGATACCTG<br>ACTCGTAATCTGTAA |
| SEQ ID NO: 33 | Amino acid sequence of AAV2-TT-S312N capsid (VP1) | MAADGYLPDWLEDTLSEGIRQWWKLKPGPPPPKPAERHKDDSR<br>GLVLPGYKYLGPFNGLDKGEPVNEADAAALEHDKAYDRQLDSG<br>DNPYLKYNHADAEFQERLKEDTSFGGNLGRAVFQAKKRILEPL<br>GLVEEPVKTAPGKKRPVEHSPAEPDSSSGTGKSGQQPARKRLN<br>FGQTGDADSVPDPQPLGQPPAAPSGLGTNTMASGSGAPMADNN<br>EGADGVGNSSGNWHCDSTWMGDRVITTSTRTWALPTYNNHLYK<br>QISSQSGASNDNHYFGYSTPWGYFDFNRFHCHFSPRDWQRLIN<br>NNWGFRPKRLNFKLFNIQVKEVTQNDGITTIANNLTSTVQVFT<br>DSEYQLPYVLGSAHQGCLPPFPADVFMVPQYGYLTLNNGSQAV<br>GRSSFYCLEYFPSQMLRTGNNFTFSYTFEDVPFHSSYAHSQSL<br>DRLMNPLIDQYLYYLSRTNTPSGTTTMSRLQFSQAGASDIRDQ<br>SRNWLPGPCYRQQRVSKTAADNNNSDYSWTGATKYHLNGRDSL<br>VNPGPAMASHKDDEEKYFPQSGVLIFGKQDSGKTNVDIEKVMI<br>TDEEEIRTTNPVATEQYGSVSTNLQSGNTQAATSDVNTQGVLP<br>GMVWQDRDVYLQGPIWAKIPHTDGHFHPSPLMGGFGLKHPPPQ<br>ILIKNTPVPANPSTTFSAAKFASFITQYSTGQVSVEIEWELQK<br>ENSKRWNPEIQYTSNYNKSVNVDFTVDTNGVYSEPRPIGTRYL<br>TRNL |

What is claimed is:

1. A modified nucleic acid encoding frataxin (FXN), wherein said nucleic acid is expressed at a greater level compared with the level of expression of the wild type FXN nucleic acid sequence of SEQ ID NO:2 in an otherwise identical cell, and wherein the modified nucleic acid comprises the nucleic acid sequence of SEQ ID NO: 7.

2. The modified nucleic acid of claim 1, wherein the nucleic acid comprises a GC content of at least 55%, a number of CpG dinucleotides not greater than 117, and a codon adaptation index (CAI) of at least 0.86.

3. A recombinant expression vector comprising the modified nucleic acid encoding the FXN of claim 1.

4. The recombinant expression vector of claim 3, wherein said vector is a recombinant adeno-associated virus (rAAV) vector and the modified nucleic acid comprising the FXN is self-complementary.

5. The recombinant expression vector of claim 3, wherein said vector is a recombinant adeno-associated virus (rAAV) vector.

6. The rAAV vector of claim 5, wherein said rAAV vector further comprises a capsid selected from the group consisting of a capsid of AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03.

7. The rAAV vector of claim 6, wherein the capsid is selected from the group consisting of a capsid of AAV2i8, AAV9, AAV-LK03 and AAV2-TT-S312N.

8. The rAAV vector of claim 4, wherein the modified nucleic acid further comprises at least one element selected from the group consisting of: at least one adeno-associated virus (AAV) terminal repeat sequence, an enhancer, a promoter, a collagen stabilizing sequence (CSS), a stop codon, and a poly-adenylation (polyA) signal sequence.

9. The rAAV vector of claim 8, said rAAV vector comprising two AAV terminal repeat sequences, a cytomegalovirus enhancer/chicken beta actin promoter (CBh) promoter, a CSS, and a bovine growth hormone poly-adenylation signal sequence (bGHpolyA).

10. The rAAV vector of claim 8, said vector comprising a nucleic acid comprising, from 5' to 3':
(a) an AAV2 terminal repeat;
(b) a CBh promoter comprising the nucleic acid sequence of SEQ ID NO:26;
(c) a modified nucleic acid encoding FXN comprising the nucleic acid sequence of SEQ ID NO:7;
(d) a CSS comprising the nucleic acid sequence of SEQ ID NO:25;
(e) a bGHpolyA signal sequence comprising the nucleic acid sequence of SEQ ID NO:27; and
(f) an AAV2 terminal repeat.

11. The rAAV vector of claim 10, further comprising an AAV2i8 capsid wherein the VP1 comprises the amino acid sequence of SEQ ID NO:29, said vector comprising a nucleic acid comprising, from 5' to 3':
(a) an AAV2 terminal repeat;
(b) a CBh promoter comprising the nucleic acid sequence of SEQ ID NO26;
(c) a modified nucleic acid encoding FXN comprising the nucleic acid sequence of SEQ ID NO:7;
(d) a CSS comprising the nucleic acid sequence of SEQ ID NO: 25;
(e) a bGHpolyA signal sequence comprising the nucleic acid sequence of SEQ ID NO:27; and
(f) an AAV2 terminal repeat.

12. The rAAV vector of claim 10, further comprising an AAV2-TT-S312N capsid wherein the VP1 comprises the amino acid sequence of SEQ ID NO:33, said vector comprising a nucleic acid comprising, from 5' to 3':
(a) an AAV2 terminal repeat;
(b) a CBh promoter comprising the nucleic acid sequence of SEQ ID NO:26;
(c) a modified nucleic acid encoding FXN comprising the nucleic acid sequence of SEQ ID NO:7;
(d) a CSS comprising the nucleic acid sequence of SEQ ID NO:25;
(e) a bGHpolyA signal sequence comprising the nucleic acid sequence of SEQ ID NO:27; and
(f) an AAV2 terminal repeat.

13. A rAAV vector for treating Friedreich ataxia (FRDA) in a patient in need thereof, wherein said vector comprises the modified nucleic acid encoding FXN of claim 1.

14. A pharmaceutical composition comprising the rAAV vector of claim 13, and a pharmaceutically acceptable carrier.

15. A method of treating FRDA in a mammal, said method comprising administering a therapeutically effective amount of the rAAV vector of claim 13.

16. The method of claim 15, wherein said rAAV vector is administered systemically, by direct cardiac administration or by intracranial administration.

17. The method of claim 16, wherein the rAAV vector is administered intracranially.

18. The method of claim 16, wherein the rAAV vector is directly administered into the heart.

19. A method of treating a disease, disorder or condition mediated by a decreased level of FXN in a mammal, the method comprising administering a therapeutically effective amount of the rAAV vector of claim 13.

20. An isolated host cell comprising the modified nucleic acid encoding FXN of claim 1.

21. The host cell of claim 20, wherein the cell is selected from the group consisting of VERO, WI38, MRC5, A549, HEK293 cells, B-50 HeLa, HepG2, Saos-2, HuH7, and HT1080.

22. The host cell of claim 21, wherein the cell is a HEK293 cell adapted to growth in suspension culture.

23. The host cell of claim 21, wherein the cell is a HEK293 cell having American Type Culture Collection (ATCC) No. PTA 13274.

24. The host cell of claim 20, said cell comprising at least one nucleic acid encoding at least one protein selected from the group consisting of a replication (Rep) protein, a capsid (Cap) protein, an adenovirus early region 1a (E1a) protein, a E1b protein, an E2a protein, an E4 protein and a viral associated (VA) RNA.

25. A method for increasing the level of frataxin in a cell, said method comprising transducing said cell with the recombinant expression vector of claim 1.

26. The vector of claim 8, comprising a nucleic acid comprising, from 5' to 3':
    (a) an AAV2 terminal repeat;
    (b) a CBh promoter comprising the nucleic acid sequence of SEQ ID NO:26;
    (c) the modified nucleic acid encoding FXN comprising the nucleic acid sequence of SEQ ID NO:7;
    (d) a bGHpolyA signal sequence comprising the nucleic acid sequence of SEQ ID NO:27; and
    (e) an AAV2 terminal repeat.

27. The vector of claim 26, further comprising a capsid selected from the group consisting of a capsid of AAV2i8, AAV9, AAV-LK03, and AAV2-TT-S312N.

28. The vector of claim 27, further comprising a CSS comprising the nucleic acid sequence of SEQ ID NO:25 immediately following the sequence encoding FXN.

29. The vector of claim 28, comprising a capsid of AAV2i8, and further comprising, from 5' to 3':
    (a) an AAV2 terminal repeat;
    (b) a CBh promoter comprising the nucleic acid sequence of SEQ ID NO:26;
    (c) the modified nucleic acid encoding FXN comprising the nucleic acid sequence of SEQ ID NO:7;
    (d) a CSS comprising the nucleic acid sequence of SEQ ID NO:25;
    (e) a bGHpolyA signal sequence comprising the nucleic acid sequence of SEQ ID NO:27; and
    (f) an AAV2 terminal repeat.

30. The vector of claim 28, comprising a capsid of AAV9, and further comprising, from 5' to 3':
    (a) an AAV2 terminal repeat;
    (b) a CBh promoter comprising the nucleic acid sequence of SEQ ID NO:26;
    (c) the modified nucleic acid encoding FXN comprising the nucleic acid sequence of SEQ ID NO:7;
    (d) a CSS comprising the nucleic acid sequence of SEQ ID NO:25;
    (e) a bGHpolyA signal sequence comprising the nucleic acid sequence of SEQ ID NO:27; and
    (f) an AAV2 terminal repeat.

31. The vector of claim 28, comprising a capsid of AAV-LK03, and further comprising, from 5' to 3':
    (a) an AAV2 terminal repeat;
    (b) a CBh promoter comprising the nucleic acid sequence of SEQ ID NO:26;
    (c) the modified nucleic acid encoding FXN comprising the nucleic acid sequence of SEQ ID NO:7;
    (d) a CSS comprising the nucleic acid sequence of SEQ ID NO:25;
    (e) a bGHpolyA signal sequence comprising the nucleic acid sequence of SEQ ID NO:27; and
    (f) an AAV2 terminal repeat.

32. The method of claim 16, wherein the systemic administration is intravenous administration.

* * * * *

SEQUENCE LISTING

<160> NUMBER OF SEQ ID NOS: 33

<210> SEQ ID NO 1
<211> LENGTH: 210
<212> TYPE: PRT
<213> ORGANISM: Artificial Sequence
<220> FEATURE:
<223> OTHER INFORMATION: Amino acid sequence of human wild type frataxin

<400> SEQUENCE: 1

```
Met Trp Thr Leu Gly Arg Arg Ala Val Ala Thr Gly Leu Leu Ala Ser
1               5                   10                  15

Pro Ser Pro Ala Gln Ala Gln Thr Leu Thr Arg Val Pro Arg Pro Ala
            20                  25                  30

Glu Leu Ala Pro Leu Cys Gly Arg Arg Gly Leu Arg Thr Asp Ile Asp
        35                  40                  45

Ala Thr Cys Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175
```

His Asp Gly Val Ser Leu His Glu Leu Leu Ala Ala Glu Leu Thr Lys
        180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 630
<212> TYPE: DNA
<213> ORGANISM: Artificial Sequence
<220> FEATURE:
<223> OTHER INFORMATION: Nucleotide sequence encoding wild type frataxin

<400> SEQUENCE: 2

```
atgtggactc tcgggcgccg cgcagtagcc ggcctcctgg cgtcacccag cccagcccag      60
gcccagaccc tcacccgggt cccgcggccg gcagagttgg ccccactctg cggccgccgt     120
ggcctgcgca ccgacatcga tgcgacctgc acgccccgcc gcgcaagttc gaaccaacgt     180
ggcctcaacc agatttggaa tgtcaaaaag cagagtgtct atttgatgaa tttgaggaaa     240
tctggaactt ggcccaccc aggctctcta gatgagacca cctatgaaag actagcagag     300
gaaacgctgg actctttagc agagtttttt gaagaccttg cagacaagcc atacacgttt     360
gaggactatg atgtctcctt tgggagtggt gtcttaactg tcaaactggg tggagatcta     420
ggaacctatg tgatcaacaa gcagacgcca acaagcaaa tctggctatc ttctccatcc     480
agtggaccta gcgttatga ctggactggg aaaaactggg tgtactccca cgacggcgtg     540
tccctccatg agctgctggc cgcagagctc actaaagcct aaaaaccaa actggacttg     600
tcttccttgg cctattccgg aaaagatgct                                    630
```

<210> SEQ ID NO 3
<211> LENGTH: 630
<212> TYPE: DNA
<213> ORGANISM: Artificial Sequence
<220> FEATURE:
<223> OTHER INFORMATION: IDT2 optimized nucleotide sequence encoding
      frataxin

<400> SEQUENCE: 3

```
atgtggacac tgggcagaag ggcggtggcc ggactgttgg cgagtcccag tcccgcgcag      60
gcgcagaccc ttactagggt gccgcggccc gcggagctgg cgccactctg cggtcgccgc     120
ggtctgagaa cggacattga tgccacttgt acacctcgga gggccagctc caaccaaagg     180
ggccttaatc aaatttggaa cgtgaagaag cagtccgtct acctgatgaa ccttcggaag     240
tcagggaccc tggccaccc gggaagcttg gatgaaacaa cttacgaaag gttggcggag     300
gagaccttgg attctcttgc agagttcttc gaagacctgg ctgataagcc ttacaccttt     360
gaggactacg atgtgtcttt tggatctgga gtgctgaccg ttaaactggg cggggatctg     420
ggcacctacg tgattaacaa gcaaactcca acaagcaga tctggctttc aagcccagt     480
agcgggccaa aacgctacga ttggaccgga agaattggg tttacagcca cgatggcgtt     540
tcactgcacg agcttctggc agcagaactg acaaaagcac tcaagacgaa gctcgacttg     600
tcatccttgg catactccgg aaaggatgcc                                    630
```

<210> SEQ ID NO 4
<211> LENGTH: 630
<212> TYPE: DNA
<213> ORGANISM: Artificial Sequence
<220> FEATURE:
<223> OTHER INFORMATION: JCAT Optimized Nucleotide sequence encoding frataxin

<400> SEQUENCE: 4

```
atgtggaccc tgggccgccg cgccgtggcc ggcctgctgg ccagccccag ccccgcccag     60
gcccagaccc tgacccgcgt gccccgcccc gccgagctgg cccccctgtg cggccgccgc    120
ggcctgcgca ccgacatcga cgccacctgc acccccgcc gcgccagcag caaccagcgc     180
ggcctgaacc agatctggaa cgtgaagaag cagagcgtgt acctgatgaa cctgcgcaag    240
agcggcaccc tgggccaccc cggcagcctg gacgagacca cctacgagcg cctggccgag    300
gagaccctgg acagcctggc cgagttcttc gaggacctgg ccgacaagcc ctacaccttc    360
gaggactacg acgtgagctt cggcagcggc gtgctgaccg tgaagctggg cggcgacctg    420
ggcacctacg tgatcaacaa gcagacccc aacaagcaga tctggctatc tagccccagc     480
agcggcccca gcgctacga ctggaccggc aagaactggg tgtacagcca cgacggcgtg     540
agcctgcacg agctgctggc cgccgagctg accaaggccc tgaagaccaa gctggacctg    600
agcagcctgg cctacagcgg caaggacgcc                                     630
```

<210> SEQ ID NO 5
<211> LENGTH: 630
<212> TYPE: DNA
<213> ORGANISM: Artificial Sequence
<220> FEATURE:
<223> OTHER INFORMATION: GeneArt optimized nucleotide sequence encoding frataxin

<400> SEQUENCE: 5

```
atgtggacac tggggagaag ggctgtggcc ggactgctgg cttctccatc tccagcccag     60
gcccagaccc tgaccagagt gcctagacct gccgaactgg cccctctgtg tggcagaaga    120
ggcctgagaa ccgacatcga cgccacctgt acccccagaa gggccagcag caatcagcgg    180
ggcctgaatc agatctggaa cgtgaagaaa cagagcgtgt acctgatgaa cctgagaaag    240
agcggcaccc tgggccaccc tggaagcctg gatgagacaa cctacgagcg gctggccgag    300
gaaaccctgg attccctggc cgagttcttc gaggacctgg ccgacaagcc ctacaccttc    360
gaggattacg acgtgtcctt cggcagcggc gtgctgacag tgaagctggg cggagatctg    420
ggcacctacg tgatcaacaa gcagaccccc aacaaacaga tctggctatc tagccccagc    480
agcggcccca agagatacga ttggaccggc aagaactggg tgtacagcca cgacggcgtg    540
tccctgcatg agctgctggc tgccgagctg accaaggccc tgaaaacaaa gctggacctg    600
tccagcctgg cctacagcgg caaggatgcc                                     630
```

<210> SEQ ID NO 6
<211> LENGTH: 630
<212> TYPE: DNA
<213> ORGANISM: Artificial Sequence
<220> FEATURE:
<223> OTHER INFORMATION: Genscript (control) optimized Nucleotide sequence encoding frataxin

<400> SEQUENCE: 6

```
atgtggacac tgggccggag agccgtcgct gggctgctgg catcaccatc ccccgcacag     60
gcacagaccc tgacaagagt ccctcggcca gcagagctgg ccccactgtg cgggcggaga    120
ggactgcgaa ccgacatcga tgctacttgt accccaaggc gagcaagctc caaccagcga    180
gggctgaacc agatttggaa tgtgaagaaa cagtctgtct acctgatgaa tctgagaaag    240
```

```
agcggcactc tgggacaccc tggcagcctg gacgagacca cctacgagcg gctggccgag    300
gaaaccctgg attccctggc cgagttcttt gaagacctgg ctgataagcc atacaccttc    360
gaagactatg acgtgagctt cggcagcggc gtgctgacag tcaaactggg cggggacctg    420
ggaacatacg tgatcaacaa gcagactcct aacaagcaga tttggctgtc tagtccctca    480
agcggcccta gaggtacga ctggacaggg aaaaactggg tgtatagtca cgatggcgtc     540
tcactgcatg agctgctggc cgctgaactg actaaagccc tgaaaactaa actggacctg    600
tcttccctgg catactctgg caaggacgcc                                    630

<210> SEQ ID NO 7
<211> LENGTH: 630
<212> TYPE: DNA
<213> ORGANISM: Artificial Sequence
<220> FEATURE:
<223> OTHER INFORMATION: Genscript (low CpG) nucleotide sequence
      encoding frataxin

<400> SEQUENCE: 7
atgtggactc tgggccggag agcagtggca ggactgctgg caagtccatc acctgctcag     60
gcacagactc tgacaagagt cccaagacct gcagagctgc tccactgtg cgggaggcgc    120 ggactgagaa cagacatcga tgctacatgt actcctcgac gggcaagctc aaccagcga    180 gggctgaacc agatttggaa tgtgaagaaa cagtccgtct acctgatgaa tctgaggaag    240
tcaggcaccc tggggcaccc aggaagtctg gacgagacca catatgaacg gctggctgag    300
gaaacactgg attctctggc cgagttcttt gaagacctgg ctgataagcc ctacacattc    360
gaagactatg atgtgagctt tggatccggc gtgctgactg tcaaactggg cggggacctg    420
ggcacttacg tgatcaacaa gcagacccct aacaagcaga tttggctgtc tagtccttca    480
agcggaccaa agcggtacga ctggaccggc aaaaactggg tgtattctca cgatggggtc    540
agtctgcatg agctgctggc cgctgaactg accaaggccc tgaagacaaa actggacctg    600
tcctctctgg catatagcgg aaaagatgcc                                    630

<210> SEQ ID NO 8
<211> LENGTH: 630
<212> TYPE: DNA
<213> ORGANISM: Artificial Sequence
<220> FEATURE:
<223> OTHER INFORMATION: IDT3 optimized Nucleotide sequence encoding
      frataxin

<400> SEQUENCE: 8
atgtggacac tgggaaggcg cgccgtggcc ggtctgttgg catcaccatc cccagcccag     60
gctcagacac tcacccgagt cccaagaccc gcagagctgg cccctctgtg cgggcgccga    120
ggccttcgca ccgatatcga tgctacatgc acgccacgca gagctagctc aaatcagagg    180
ggactcaacc agatatggaa tgtcaagaag caaagcgtgt atctcatgaa cctccggaaa    240
agcggcaccc tgggacatcc cggtctctc gacgagacca cttatgaaag actggcagag    300
gagactcttg acagtctggc ggagttcttc aagacctcg ctgacaagcc atataccttc    360
gaagattacg acgtctcctt cggctctggg gtgctgactg tcaagcttgg cggcgacctg    420
gggacctacg tgatcaacaa gcagactcca aacaagcaaa tctggctatc tagtccaagc    480
tccggaccca agatacga ttggacaggc aagaattggg tttactccca cgacggggtg     540
tccctccatg agctgctggc cgcagagctg acgaaggccc tgaagaccaa gctggatctc    600
```
tcctccctgg catacagtgg taaggacgct                                    630

<210> SEQ ID NO 9
<211> LENGTH: 630
<212> TYPE: DNA
<213> ORGANISM: Artificial Sequence
<220> FEATURE:
<223> OTHER INFORMATION: IDT5 optimized Nucleotide sequence encoding
      frataxin

<400> SEQUENCE: 9
atgtggacac tgggccggcg cgccgtcgct gggctgctcg caagcccag cccagcccaa      60 gcgcagactc tgactagggt gccgcggcct gccgagttgg ccccctgtg cggtaggaga     120 ggcctgcgca cagacatcga tgccacttgc acaccccggc gggccagctc taaccaaagg    180
ggcctgaatc aaatttggaa cgtcaaaaaa cagtctgtat atctgatgaa ctccggaaa     240 tctggaacgc tcgggcatcc cggatctctt gacgagacca cctacgagcg actggccgag    300
gaaacccttg acagcctggc agaattcttt gaggatctgg ctgataaacc ctatacccttt   360 gaagattacg atgtgagttt tggtagcgga gtactgactg ttaagctggg cggtgatctc    420
ggtacgtatg ttatcaataa acaaaccccc aataaacaga tttggctctc ctccccatcc    480
tctgggccta agcgctatga ctggacagga agaattggg tctattcaca cgacggagtc     540
agtttgcacg agctcctcgc cggcagagtt accaaggccc ttaagactaa gctcgacctg    600
tcaagcctcg cttactctgg taaggacgct                                    630

<210> SEQ ID NO 10
<211> LENGTH: 630
<212> TYPE: DNA
<213> ORGANISM: Artificial Sequence
<220> FEATURE:
<223> OTHER INFORMATION: Nucleotide sequence encoding frataxin

<400> SEQUENCE: 10
atgtggactc tcgggcgccg cgcagtagcc ggcctcctgg cgtcacccag cccggcccag      60
gcccagaccc tcacccgggt cccgcggccg gcagagttgg ccccactctg cggccgccgt    120
ggcctgcgca ccgacatcga tgcgacctgc acgccccgcc gcgcaagttc gaaccaacgt    180
ggcctcaacc agatttggaa tgtcaaaaag cagagtgtct atttgatgaa tttgaggaaa    240
tctggaactt gggccacccc aggctctcta gatgagacca cctatgaaag actagcagag    300
gaaacgctgg actctttagc agagtttttt gaagaccttg cagacaagcc atacacgttt    360
gaggactatg atgtctcctt gggagtggt gtcttaactg tcaaactggg tggagatcta    420
ggaacctatg tgatcaacaa gcagacgcca aacaagcaaa tctggctatc ttctccatcc    480
agtggaccta gcgttatga ctggactggg aaaaactggg tgtactccca cgacggcgtg     540
tccctccatg agctgctggc cgcagagctc actaaagcct taaaaaccaa actggacttg    600
tcttccttgg cctattccgg aaaagatgct                                    630

<210> SEQ ID NO 11
<211> LENGTH: 630
<212> TYPE: DNA
<213> ORGANISM: Artificial Sequence
<220> FEATURE:
<223> OTHER INFORMATION: IDT-1 optimized Nucleotide sequence encoding
      frataxin

<400> SEQUENCE: 11
atgtggactc tgggtaggcg agcggtggcc ggcctgttgg catctcctag tcctgcacaa      60

| | |
|---|---|
| gctcaaacgc tgactagagt ccctcggcca gcagaactgg cgccactttg cggccggcgc | 120 |
| ggtcttcgca ctgatattga tgccacttgc acacccggc gcgcctccag taatcagcgg | 180 |
| ggacttaatc aaatttggaa tgtgaagaag cagtctgtgt atcttatgaa tctgcggaag | 240 |
| agcgggaccc tggccaccc tggtagcctt gatgaaacca cctatgagcg cctggccgaa | 300 |
| gagacactgg acagtcttgc cgagtttttt gaggatctgg ccgacaaacc ttatactttt | 360 |
| gaggactatg acgtgtcctt tggatctggt gtattgaccg taaaactcgg gggagacctt | 420 |
| gggacgtatg taataaataa gcagaccca aacaagcaga tctggctatc ttctccaagt | 480 |
| agtggtccta agatatga ttggacgggc aagaactggg tctattccca tgatggcgtc | 540 |
| tctttgcatg aactccttgc agcagagctg accaaggcct gaagaccaa attggatctc | 600 |
| agcagcctcg cctatagtgg caaagatgca | 630 |

<210> SEQ ID NO 12
<211> LENGTH: 630
<212> TYPE: DNA
<213> ORGANISM: Artificial Sequence
<220> FEATURE:
<223> OTHER INFORMATION: IDT-4 optimized Nucleotide sequence encoding frataxin

<400> SEQUENCE: 12

| | |
|---|---|
| atgtggactc tgggccggcg ggccgtagct ggcttgctgg ctagcccaag tcccgcccag | 60 |
| gctcagactc tcaccagggt acccaggccc gcagagcttg ctccactctg cggacgcagg | 120 |
| ggtctgcgaa ccgatatcga cgcaacttgc acgccgcgga gggcctcttc aaaccagaga | 180 |
| ggactcaatc aaatttggaa tgtaaagaaa cagagcgtgt atctcatgaa cctccgaaag | 240 |
| agtgggactc ttgggcaccc cggctccctg gacgagacta cttacgagcg cctggccgaa | 300 |
| gaaaccttgg attccctggc ggagtttttt gaagacttgg cagacaagcc ttataccttc | 360 |
| gaggattacg acgtgagttt tggctctggt gttcttacag tcaagctcgg tggcgacctt | 420 |
| ggcacttatg taattaacaa gcagacacct aacaagcaga tctggctttc tagtccgtct | 480 |
| tccggtccca aaaggtacga ttggactgga agaactgggt ctacagtca cgacggtgtc | 540 |
| tccctgcacg aattgcttgc ggcagagctg actaaggcgc tcaaaacaaa actggatctg | 600 |
| tccagccttg cctatagcgg gaaggacgca | 630 |

<210> SEQ ID NO 13
<211> LENGTH: 2211
<212> TYPE: DNA
<213> ORGANISM: Artificial Sequence
<220> FEATURE:
<223> OTHER INFORMATION: Nucleotide sequence encoding chimeric AAV2.5 Vector Capsid VP1

<400> SEQUENCE: 13

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg accccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt gggggcaacc tcggacgagc agtcttccag | 360 |
| gcgaaaaaga gggttcttga acctctgggc ctggttgagg aacctgttaa gacggctccg | 420 |

```
ggaaaaaaga ggccggtaga gcactctcct gtggagccag actcctcctc gggaaccgga       480
aaggcgggcc agcagcctgc aagaaaaaga ttgaattttg gtcagactgg agacgcagac       540
tcagtacctg accccagcc tctcggacag ccaccagcag ccccctctgg tctgggaact       600
aatacgatgg ctacaggcag tggcgcacca atggcagaca taacgagggg cgccgacgga       660
gtgggtaatt cctcgggaaa ttggcattgc gattccacat ggatgggcga cagagtcatc       720
accaccagca cccgaacctg ggccctgccc acctacaaca accacctcta caaacaaatt       780
tccagcgctt caacgggagc ctcgaacgac aatcactact ttggctacag caccccttgg       840
gggtattttg acttcaacag attccactgc cacttttcac cacgtgactg gcaaagactc       900
atcaacaaca actggggatt ccgacccaag agactcaact tcaagctctt taacattcaa       960
gtcaaagagg tcacgcagaa tgacggtacg acgacgattg ccaataacct taccagcacg       1020
gttcaggtgt ttactgactc ggagtaccag ctcccgtacg tcctcggctc ggcgcatcaa       1080
ggatgcctcc cgccgttccc agcagacgtc ttcatggtgc cacagtatgg atacctcacc       1140
ctgaacaacg gagtcaggc agtaggacgc tcttcatttt actgcctgga gtactttcct       1200
tctcagatgc tgcgtaccgg aaacaacttt accttcagct acacttttga ggacgttcct       1260
ttccacagca gctacgctca cagccagagt ctggaccgtc tcatgaatcc tctcatcgac       1320
cagtacctgt attacttgag cagaacaaac actccaagtg aaccaccac gcagtcaagg       1380 cttcagtttt ctcaggccgg agcgagtgac attcgggacc agtctaggaa ctggcttcct       1440
ggaccctgtt accgccagca gcgagtatca agacatctg cggataacaa caacagtgaa       1500
tactcgtgga ctggagctac caagtaccac ctcaatggca gagactctct ggtgaatccg       1560
ggcccggcca tggcaagcca aggacgat gaagaaaagt ttttcctca gagcggggtt         1620 ctcatctttg gaagcaagg ctcagagaaa acaaatgtgg acattgaaaa ggtcatgatt       1680
acagacgaag aggaaatcag gacaaccaat cccgtggcta cggagcagta tggttctgta       1740
tctaccaacc tccagagagg caacagacaa gcagctaccg cagatgtcaa cacacaaggc      1800
gttcttccag gcatggtctg gcaggacaga gatgtgtacc ttcaggggcc catctgggca      1860
aagattccac acacggacgg acattttcac ccctctcccc tcatgggtgg attcggactt      1920
aaacaccctc ctccacagat tctcatcaag aacacccgg tacctgcgaa tccttcgacc      1980
accttcagtg cggcaaagtt tgcttccttc atcacacagt actccacggg acaggtcagc      2040
gtggagatcg agtgggagct gcagaaggaa aacagcaaac gctggaatcc cgaaattcag      2100
tacacttcca actacgccaa gtctgtcaat gtggacttta ctgtggacaa taatggcgtg      2160
tattcagagc ctcgccccat tggcaccaga tacctgactc gtaatctgta a               2211
```

<210> SEQ ID NO 14
<211> LENGTH: 2211
<212> TYPE: DNA
<213> ORGANISM: Artificial Sequence
<220> FEATURE:
<223> OTHER INFORMATION: Nucleotide sequence encoding wildtypeAAV1
    capsid (VP1)

<400> SEQUENCE: 14

```
atggctgccg atggttatct tccagattgg ctcgaggaca acctctctga ggcattcgc        60 gagtggtggg acttgaaacc tggagccccg aagcccaaag ccaaccagca aaagcaggac      120
gacgccgggg tctggtgct tcctggctac aagtacctcg accccttcaa cggactcgac      180 aaggggggagc ccgtcaacgc ggcggacgca gcggccctcg agcacgacaa ggcctacgac      240
```

-continued

```
cagcagctca aagcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaac gtccggtaga gcagtcgcca aagagccag actcctcctc gggcatcggc       480
aagacaggcc agcagcccgc taaaaagaga ctcaattttg gtcagactgg cgactcagag      540
tcagtccccg atccacaacc tctcggagaa cctccagcaa ccccgctgc tgtgggacct       600 actacaatgg cttcaggcgg tggcgcacca atggcagaca ataacgaagg cgccgacgga      660
gtgggtaatg cctcaggaaa ttggcattgc gattccacat ggctgggcga cagagtcatc      720
accaccagca cccgcacctg ggccttgccc acctacaata accacctcta caagcaaatc      780
tccagtgctt caacggggc cagcaacgac aaccactact cggctacag cacccctgg        840 gggtattttg atttcaacag attccactgc cacttttcac cacgtgactg cagcgactc      900 atcaacaaca attggggatt ccggcccaag agactcaact tcaaactctt caacatccaa     960
gtcaaggagg tcacgacgaa tgatggcgtc acaaccatcg ctaataaccct taccagcacg   1020 gttcaagtct ctctcggactc ggagtaccag cttccgtacg tcctcggctc tgcgcaccag   1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct acacctttga ggaagtgcct    1260
ttccacagca gctacgcgca cagccagagc ctggaccggc tgatgaatcc tctcatcgac    1320
caatacctgt attacctgaa cagaactcaa aatcagtccg gaagtgccca aaacaaggac    1380
ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttcccat gagcggtgtc    1620
atgatttttg gaaaagagag cgccggagct tcaaacactg cattggacaa tgtcatgatt    1680
acagacgaag aggaaattaa agccactaac cctgtggcca ccgaaagatt tgggaccgtg    1740
gcagtcaatt tccagagcag cagcacagac cctgcgaccg gagatgtgca tgctatggga    1800
gcattacctg catggtgtg gcaagataga gacgtgtacc tgcagggtcc catttgggcc    1860
aaaattcctc acacagatgg acactttcac ccgtctcctc ttatgggcgg ctttggactc    1920
aagaacccgc ctcctcagat cctcatcaaa aacacgcctg ttcctgcgaa tcctccggcg    1980
gagttttcag ctacaaagtt tgcttcattc atcacccaat actccacagg acaagtgagt    2040
gtggaaattg aatgggagct gcagaaagaa aacagcaagc gctggaatcc cgaagtgcag    2100
tacacatcca attatgcaaa atctgccaac gttgatttta ctgtggacaa caatggactt    2160
tatactgagc ctcgccccat ggcacccgt taccttaccc gtccctgta a               2211
```

<210> SEQ ID NO 15
<211> LENGTH: 2208
<212> TYPE: DNA
<213> ORGANISM: Artificial Sequence
<220> FEATURE:
<223> OTHER INFORMATION: Nucleotide sequence encoding modified AAV1.1 capsid VP1

<400> SEQUENCE: 15

```
atggctgccg atggttatct tccagattgg ctcgaggaca acctctctga gggcattcgc       60
```

```
gagtggtggg acttgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg atccacaacc tctcggagaa cctccagcaa cccccgctgc tgtgggacct    600
actacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgcacctg ggccttgccc acctacaata accacctcta caagcaaatc    780
tccagtgctt caggggccag caacgacaac cactacttcg gctacagcac ccctggggg    840 tattttgatt tcaacagatt ccactgccac ttttcaccac gtgactggca gcgactcatc    900
aacaacaatt ggggattccg gcccaagaga ctcaacttca aactcttcaa catccaagtc    960
aaggaggtca cgacgaatga tggcgtcaca accatcgcta taaccttac cagcacggtt   1020 caagtcttct cggactcgga gtaccagctt ccgtacgtcc tcggctctgc gcaccagggc   1080
tgcctccctc cgttcccggc ggacgtgttc atgattccgc aatacggcta cctgacgctc   1140
aacaatggca gccaagccgt gggacgttca tcctttact gcctggaata tttcccttct   1200
cagatgctga gaacgggcaa caactttacc ttcagctaca cctttgagga agtgcctttc   1260
cacagcagct acgcgcacag ccagagcctg gaccggctga tgaatcctct catcgaccaa   1320
tacctgtatt acctgaacag aactcaaaat cagtccggaa gtgcccaaaa caaggacttg   1380
ctgtttagcc gtgggtctcc agctggcatg tctgttcagc ccaaaaactg gctacctgga   1440
ccctgttatc ggcagcagcg cgtttctaaa acaaaaacag acaacaacaa cagcaatttt   1500
acctggactg tgtgcttcaaa atataacctc aatgggcgtg aatccatcat caaccctggc   1560
actgctatgg cctcacacaa agacgacgaa gacaagttct ttcccatgag cggtgtcatg   1620
atttttggaa agagagcgc cggagcttca aacactgcat ggacaatgt catgattaca   1680 gacgaagagg aaattaaagc cactaaccct gtggccaccg aaagatttgg gaccgtggca   1740
gtcaatttcc agagcagcag cacagaccct gcgaccggag atgtgcatgc tatgggagca   1800
ttacctggca tggtgtggca agatagagac gtgtacctgc agggtcccat ttgggccaaa   1860
attcctcaca cagatggaca ctttcacccg tctcctctta tgggcggctt tggactcaag   1920
aacccgcctc tcagatcct catcaaaaac acgcctgttc ctgcgaatcc tccggcggag   1980
ttttcagcta caaagtttgc ttcattcatc acccaatact ccacaggaca agtgagtgtg   2040
gaaattgaat gggagctgca gaaagaaaac agcaagcgct ggaatcccga agtgcagtac   2100
acatccaatt atgcaaaatc tgccaacgtt gattttactg tggacaacaa tggactttat   2160
actgagcctc gcccattgg cacccgttac cttacccgtc cctgtaa             2208
```

<210> SEQ ID NO 16
<211> LENGTH: 2211
<212> TYPE: DNA
<213> ORGANISM: Artificial Sequence
<220> FEATURE:
<223> OTHER INFORMATION: Nucleotide sequence encoding wildtype AAV6 capsid (VP1)

<400> SEQUENCE: 16

| | | | | | |
|---|---|---|---|---|---|
| atggctgccg | atggttatct | tccagattgg | ctcgaggaca | acctctctga | gggcattcgc | 60 |
| gagtggtggg | acttgaaacc | tggagccccg | aaacccaaag | ccaaccagca | aaagcaggac | 120 |
| gacggccggg | gtctggtgct | tcctggctac | aagtacctcg | gacccttcaa | cggactcgac | 180 |
| aaggggagc | ccgtcaacgc | ggcggatgca | gcggccctcg | agcacgacaa | ggcctacgac | 240 |
| cagcagctca | aagcgggtga | caatccgtac | ctgcggtata | accacgccga | cgccgagttt | 300 |
| caggagcgtc | tgcaagaaga | tacgtctttt | gggggcaacc | tcgggcgagc | agtcttccag | 360 |
| gccaagaaga | gggttctcga | accttttggt | ctggttgagg | aaggtgctaa | gacggctcct | 420 |
| ggaaagaaac | gtccggtaga | gcagtcgcca | caagagccag | actcctcctc | gggcattggc | 480 |
| aagacaggcc | agcagcccgc | taaaaagaga | ctcaattttg | gtcagactgg | cgactcagag | 540 |
| tcagtccccg | acccacaacc | tctcggagaa | cctccagcaa | ccccgctgc | tgtgggacct | 600 |
| actacaatgg | cttcaggcgg | tggcgcacca | atggcagaca | ataacgaagg | cgccgacgga | 660 |
| gtgggtaatg | cctcaggaaa | ttggcattgc | gattccacat | ggctgggcga | cagagtcatc | 720 |
| accaccagca | cccgaacatg | ggcctttgccc | acctataaca | accacctcta | caagcaaatc | 780 |
| tccagtgctt | caacggggggc | cagcaacgac | aaccactact | cggctacag | cacccctgg | 840 |
| gggtattttg | atttcaacag | attccactgc | catttctcac | cacgtgactg | gcagcgactc | 900 |
| atcaacaaca | attgggggatt | ccggcccaag | agactcaact | tcaagctctt | caacatccaa | 960 |
| gtcaaggag | tcacgacgaa | tgatggcgtc | acgaccatcg | ctaataacct | taccagcacg | 1020 |
| gttcaagtct | tctcggactc | ggagtaccag | ttgccgtacg | tcctcggctc | tgcgcaccag | 1080 |
| ggctgcctcc | ctccgttccc | ggcggacgtg | ttcatgattc | cgcagtacgg | ctacctaacg | 1140 |
| ctcaacaatg | gcagccaggc | agtgggacgg | tcatcctttt | actgcctgga | atatttccca | 1200 |
| tcgcagatgc | tgagaacggg | caataacttt | accttcagct | acaccttcga | ggacgtgcct | 1260 |
| ttccacagca | gctacgcgca | cagccagagc | ctggaccggc | tgatgaatcc | tctcatcgac | 1320 |
| cagtacctgt | attcctgaa | cagaactcag | aatcagtccg | gaagtgccca | aaacaaggac | 1380 |
| ttgctgttta | gccgggggtc | tccagctggc | atgtctgttc | agcccaaaaa | ctggctacct | 1440 |
| ggaccctgtt | accggcagca | gcgcgtttct | aaaacaaaaa | cagacaacaa | caacagcaac | 1500 |
| tttacctgga | ctggtgcttc | aaaatataac | cttaatgggc | gtgaatctat | aatcaaccct | 1560 |
| ggcactgcta | tggcctcaca | caaagacgac | aaagacaagt | tctttcccat | gagcggtgtc | 1620 |
| atgattttttg | gaaaggagag | cgccggagct | tcaaacactg | cattggacaa | tgtcatgatc | 1680 |
| acagacgaag | aggaaatcaa | agccactaac | ccgtggcca | ccgaaagatt | tgggactgtg | 1740 |
| gcagtcaatc | tccagagcag | cagcacagac | cctgcgaccg | gagatgtgca | tgttatggga | 1800 |
| gccttacctg | gaatggtgtg | gcaagacaga | gacgtatacc | tgcagggtcc | tatttgggcc | 1860 |
| aaaattcctc | acacggatgg | acactttcac | ccgtctcctc | tcatgggcgg | ctttgggactt | 1920 |
| aagcacccgc | ctcctcagat | cctcatcaaa | aacacgcctg | ttcctgcgaa | tcctccggca | 1980 |
| gagttttcgg | ctacaaagtt | tgcttcattc | atcacccagt | attccacagg | acaagtgagc | 2040 |
| gtggagattg | aatgggagct | gcagaaagaa | aacagcaaac | gctggaatcc | cgaagtgcag | 2100 |
| tatacatcta | actatgcaaa | atctgccaac | gttgatttca | ctgtggacaa | caatggactt | 2160 |
| tatactgagc | ctcgccccat | tggcacccgt | tacctcaccc | gtccctgta | a | 2211 |

<210> SEQ ID NO 17
<211> LENGTH: 2205
<212> TYPE: DNA
<213> ORGANISM: Artificial Sequence
<220> FEATURE:
<223> OTHER INFORMATION: Nucleotide sequence encoding modified AAV6.1 capsid VP1

<400> SEQUENCE: 17

```
atggctgccg atggttatct tccagattgg ctcgaggaca acctctdgag ggcattcgcg      60
agtggtggga cttgaaacct ggagccccga acccaaagc caaccagcaa aagcaggacg     120
acggccgggg tdggtgcttc ctggctacaa gtacctcgga cccttcaacg gactcgacaa    180
gggggagccc gtcaacgcgg cggatgcagc ggccctcgag cacgacaagg cctacgacca    240
gcagctcaaa gcgggtgaca atccgtacct gcggtataac cacgccgacg ccgagtttca    300
ggagcgtctg caagaagata cgtcttttgg gggcaacctc gggcgagcag tcttccaggc    360
caagaagagg gttctcgaac cttttggtdg gttgaggaag gtgctaagac ggctcctgga    420
aagaaacgtc cggtagagca gtcgccacaa gagccagact cctcctcggg cattggcaag    480
acaggccagc agcccgctaa aaagagactc aattttggtc agactggcga ctcagagtca    540
gtcccccgacc acaacctct cggagaacct ccagcaaccc ccgctgctgt gggacctact    600
acaatggctt caggcggtgg cgcaccaatg gcagacaata cgaaggcgc cgacggagtg    660
ggtaatgcct caggaaattg gcattgcgat tccacatggc tgggcgacag agtcatcacc    720
accagcaccc gaacatgggc cttgcccacc tataacaacc acctctacaa gcaaatctcc    780
agtgcttcag gggccagcaa cgacaaccac tacttcggct acagcacccc ctgggggtat    840
tttgatttca acagattcca ctgccatttc tcaccacgtg actggcagcg actcatcaac    900
aacaattggg gattccggcc caagagactc aacttcaagc tcttcaacat ccaagtcaag    960
gaggtcacga cgaatgatgg cgtcacgacc atcgctaata accttaccag cacggttcaa   1020
gtcttctcgg actcggagta ccagttgccg tacgtcctcg gctctgcgca ccagggctgc   1080
ctccctccgt tcccggcgga cgtgttcatg attccgcagt acggctacct aacgctcaac   1140
aatggcagcc aggcagtggg acggtcatcc tttactgcc tggaatattt cccatcgcag   1200
atgctgagaa cggcaataa ctttacctttc agctacacct tcgaggacgt gccttccac   1260
agcagctacg cgcacagcca gagcctggac cggctgatga atcctctcat cgaccagtac   1320
ctgtattacc tgaacagaac tcagaatcag tccggaagtg cccaaaacaa ggacttgctg   1380
tttagccggg ggtctccagc tggcatgtct gttcagccca aaaactggct acctggaccc   1440
tgttaccggc agcagcgcgt ttctaaaaca aaaacagaca caacaacag caactttacc   1500
tggactggtg cttcaaaata taaccttaat gggcgtgaat ctataatcaa ccctggcact   1560
gctatggcct cacacaaaga cgacaaagac aagttctttc ccatgagcgg tgtcatgatt   1620
tttggaaagg agagcgccgg agcttcaaac actgcattgg acaatgtcat gatcacagac   1680
gaagaggaaa tcaaagccac taaccccgtg gccaccgaaa gatttgggac tgtggcagtc   1740
aatctccaga gcagcagcac agaccctgcg accggagatg tgcatgttat gggagcctta   1800
cctggaatgg tgtggcaaga cagagacgta tacctgcagg gtcctatttg gccaaaaatt   1860
cctcacacgg atggacactt tcacccgtct cctctcatgg gcggctttgg acttaagcac   1920
ccgcctcctc agatcctcat caaaaacacg cctgttcctg cgaatcctcc ggcagagttt   1980
tcggctacaa gtttgcttc attcatcacc cagtattcca caggacaagt gagcgtggag   2040
attgaatggg agctgcagaa agaaaacagc aaacgctgga atcccgaagt gcagtataca   2100
```

```
tctaactatg caaaatctgc caacgttgat ttcactgtgg acaacaatgg actttatact    2160
gagcctcgcc ccattggcac ccgttacctc acccgtcccc tgtaa                    2205

<210> SEQ ID NO 18
<211> LENGTH: 2208
<212> TYPE: DNA
<213> ORGANISM: Artificial Sequence
<220> FEATURE:
<223> OTHER INFORMATION: Nucleotide sequence encoding modified AAV6.3.1
      capsid VP1

<400> SEQUENCE: 18
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180 aaggggagc ccgtcaacgc ggcggatgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaaga gggttctcga accttttggt ctggttgagg aaggtgctaa gacggctcct     420
ggaaagaaac gtccggtaga gcagtcgcca caagagccag actcctcctc gggcattggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgaacatg gccttgccc acctataaca accacctcta caagcaaatc     780
tccagtgctt caggggccag caacgacaac cactacttcg gctacagcac ccctgggggg     840
tattttgatt caacagatt ccactgccat ttctccacca gtgactggca gcgactcatc     900
aacaacaatt ggggattccg gcccaagaga ctcaacttca gctcttcaa catccaagtc     960 aaggaggtca cgacgaatga tggcgtcacg accatcgcta taaccttac cagcacggtt    1020 caagtcttct cggactcgga gtaccagttg ccgtacgtcc tcggctctgc gcaccagggc    1080
tgcctccctc cgttcccggc ggacgtgttc atgattccgc agtacggcta cctaacgctc    1140
aacaatggca gccaggcagt gggacggtca tcctttttact gcctggaata tttcccatcg    1200
cagatgctga gaacgggcaa taactttacc ttcagctaca cctttgagga cgtgccttc    1260 cacagcagct acgcgcacag ccagagcctg gaccggctga tgaatcctct catcgaccag    1320
tacctgtatt acctgaacag aactcagaat cagtccggaa gtgcccaaaa caaggacttg    1380
ctgtttagcc gggggtctcc agctggcatg tctgttcagc ccaaaaactg gctacctgga    1440
ccctgttacc ggcagcagcg cgtttctaaa acaaaaacag acaacaacaa cagcaacttt    1500
acctggactg gtgcttcaaa atataacctt aatgggcgtg aatctataat caaccctggc    1560
actgctatgg cctcacacaa agacgacgaa gacaagttct tcccatgag cggtgtcatg    1620 atttttggaa aggagagcgc cggagcttca aacactgcat ggacaatgt catgatcaca    1680 gacgaagagg aaatcaaagc cactaacccc gtggccaccg aaagatttgg gactgtggca    1740
gtcaatctcc agagcagcag cacagaccct gcgaccggag atgtgcatgt tatgggagcc    1800
ttacctggaa tggtgtggca agacagagac gtataccctg cagggtcctat ttgggccaaa    1860 attcctcaca cggatggaca ctttcacccg tctcctctca tgggcggctt tggacttaag    1920
```

```
cacccgcctc ctcagatcct catcaaaaac acgcctgttc ctgcgaatcc tccggcagag   1980
ttttcggcta caaagtttgc ttcattcatc acccagtatt ccacaggaca agtgagcgtg   2040
gagattgaat gggagctgca gaaagaaaac agcaaacgct ggaatcccga agtgcagtat   2100
acatctaact atgcaaaatc tgccaacgtt gatttcactg tggacaacaa tggactttat   2160
actgagcctc gccccattgg cacccgttac ctcacccgtc ccctgtaa               2208

<210> SEQ ID NO 19
<211> LENGTH: 983
<212> TYPE: DNA
<213> ORGANISM: Artificial Sequence
<220> FEATURE:
<223> OTHER INFORMATION: Nucleotide sequence encoding human wild type
      frataxin (WT FXN) for cloning into pTRs-KS-CBh-EGFP-BGH scAAV
      vector

<400> SEQUENCE: 19
tagaagaccg gtcgccacca tgtggactct cgggcgccgc gcagtagccg gcctcctggc   60
gtcacccagc ccagcccagg cccagaccct cacccgggtc ccgcggccgg cagagttggc   120
cccactctgc ggccgccgtg gcctgcgcac cgacatcgat gcgacctgca cgccccgccg   180
cgcaagttcg aaccaacgtg gcctcaacca gatttggaat gtcaaaaagc agagtgtcta   240
tttgatgaat ttgaggaaat ctggaacttt gggccaccca ggctctctag atgagaccac   300
ctatgaaaga ctagcagagg aaacgctgga ctctttagca gagttttttg aagaccttgc   360
agacaagcca tacacgtttg aggactatga tgtctccttt ggagtggtg tcttaactgt    420 caaactgggt ggagatctag aacctatgt gatcaacaag cagacgccaa acaagcaaat   480
ctggctatct tctccatcca gtggacctaa gcgttatgac tggactggga aaaactgggt   540
gtactcccac gacggcgtgt ccctccatga gctgctggcc gcagagctca ctaaagcctt   600
aaaaaccaaa ctggacttgt cttccttggc ctattccgga aaagatgctt gacgagcggc   660
cgctcctagg agcagtatcg atcccagccc acttttcccc aatacgacta gtactcgact   720
gtgccttcta gttgccagcc atctgttgtt tgccctccc ccgtgccttc cttgaccctg     780
gaaggtgcca ctcccactgt cctttcctaa taaaatgagg aaattgcatc gcattgtctg   840
agtaggtgtc attctattct ggggggtggg gtggggcagg acagcaaggg ggaggattgg   900
gaagacaaca gcaggcatgc tggggatgcg gtgggctcta tggcttctga gcggaaaga    960 accagctttg gacgcgtctt aag                                          983

<210> SEQ ID NO 20
<211> LENGTH: 983
<212> TYPE: DNA
<213> ORGANISM: Artificial Sequence
<220> FEATURE:
<223> OTHER INFORMATION: IDT1 Codon optimized nucleotide sequence
      encoding FXN for cloning into pTRs-KS-CBh-EGFP-BGH scAAV vector

<400> SEQUENCE: 20
tagaagaccg gtcgccacca tgtggactct gggtaggcga gcggtggccg gcctgttggc   60
atctcctagt cctgcacaag ctcaaacgct gactagagtc cctcggccag cagaactggc   120
gccactttgc ggccggcgcg tcttcgcac tgatattgat gccacttgca caccccggcg    180
cgcctccagt aatcagcggg gacttaatca aatttggaat gtgaagaagc agtctgtgta   240
tcttatgaat ctgcggaaga gcgggaccct gggccaccct ggtagccttg atgaaaccac   300
ctatgagcgc ctggccgaag agacactgga cagtcttgcc gagttttttg aggatctggc   360
```

```
cgacaaacct tatactttg aggactatga cgtgtccttt ggatctggtg tattgaccgt      420
aaaactcggg ggagaccttg ggacgtatgt aataaataag cagacccaa acaagcagat      480 ctggctcagc tctccaagta gtggtcctaa gagatatgat tggacgggca agaactgggt     540
ctattcccat gatggcgtct ctttgcatga actccttgca gcagagctga ccaaggcctt    600
gaagaccaaa ttggatctca gcagcctcgc ctatagtggc aaagatgcat agcgagcggc    660
cgctcctagg agcagtatcg atcccagccc acttttcccc aatacgacta gtactcgact    720
gtgccttcta gttgccagcc atctgttgtt tgcccctccc ccgtgccttc cttgaccctg    780
gaaggtgcca ctcccactgt cctttcctaa taaaatgagg aaattgcatc gcattgtctg    840
agtaggtgtc attctattct gggggtgggg gtggggcagg acagcaaggg ggaggattgg    900
gaagacaaca gcaggcatgc tggggatgcg gtgggctcta tggcttctga ggcggaaaga    960
accagctttg gacgcgtctt aag                                            983
```

<210> SEQ ID NO 21
<211> LENGTH: 983
<212> TYPE: DNA
<213> ORGANISM: Artificial Sequence
<220> FEATURE:
<223> OTHER INFORMATION: Codon optimized nucleotide sequence encoding
      FXN IDT3 (low expresser) for cloning into pTRs-KS-CBh-EGFP-BGH
      scAAV vector

<400> SEQUENCE: 21

```
tagaagaccg tcgccacca tgtggacact gggaaggcgc gccgtggccg gtctgttggc      60
atcaccatcc ccagcccagg ctcagacact cacccgagtc ccaagacccg cagagctggc    120
ccctctgtgc gggcgccgag gccttcgcac cgatatcgat gctacatgca cgccacgcag    180
agctagctca aatcagaggg gactcaacca gatatggaat gtcaagaagc aaagcgtgta    240
tctcatgaac ctccggaaaa gcggcaccct gggacatccc gggtctctcg acgagaccac    300
ttatgaaaga ctggcagagg agactcttga cagtctggcg gagttcttcg aagacctcgc    360
tgacaagcca tataccttcg aagattacga cgtctccttc ggctctgggg tgctgactgt    420
caagcttggc ggcgacctgg ggacctacgt gatcaacaag cagactccaa acaagcaaat    480
ctggctcagc agtccaagct ccggacccaa gagatacgat tggacaggca agaattgggt    540
ttactcccac gacggggtgt ccctccatga gctgctggcc gctgagctga cgaaggcgct   600
gaagaccaag ctggatctct cctccctggc atacagtggt aaggacgctt gacgagcggc    660
cgctcctagg agcagtatcg atcccagccc acttttcccc aatacgacta gtactcgact    720
gtgccttcta gttgccagcc atctgttgtt tgcccctccc ccgtgccttc cttgaccctg    780
gaaggtgcca ctcccactgt cctttcctaa taaaatgagg aaattgcatc gcattgtctg    840
agtaggtgtc attctattct gggggtgggg gtggggcagg acagcaaggg ggaggattgg    900
gaagacaaca gcaggcatgc tggggatgcg gtgggctcta tggcttctga ggcggaaaga    960
accagctttg gacgcgtctt aag                                            983
```

<210> SEQ ID NO 22
<211> LENGTH: 983
<212> TYPE: DNA
<213> ORGANISM: Artificial Sequence
<220> FEATURE:
<223> OTHER INFORMATION: Codon-optimized nucleotide sequence encoding
      FXN IDT4 for cloning into pTRs-KS-CBh-EGFP-BGH scAAV vector

<400> SEQUENCE: 22

```
tagaagaccg gtcgccacca tgtggactct gggccggcgg gccgtagctg gcttgctggc    60
tagcccaagt cccgcccagg ctcagactct caccagggta cccaggcccg cagagcttgc   120
tccactctgc ggacgcaggg gtctgcgaac cgatatcgac gcaacttgca cgccgcggag   180
ggcctcttca aaccagagag gactcaatca aatttggaat gtaaagaaac agagcgtgta   240
tctcatgaac ctccgaaaga gtgggactct tgggcacccc ggctccctgg acgagactac   300
ttacgagcgc ctggccgaag aaaccttgga ttccctggcg gagttttttg aagacttggc   360
agacaagcct tataccttcg aggattacga cgtgagtttt ggctctggtg ttcttacagt   420
caagctcggt ggcgaccttg cacttatgt aattaacaag cagacaccta acaagcagat   480
ctggctttct agtccgtctt ccggtcccaa aggtacgat tggactggaa agaactgggt   540
ctacagtcac gacggtgtct ccctgcacga attgcttgcg gctgagctga ctaaggcgct   600
caaaacaaaa ctggatctgt ccagccttgc ctatagcggg aaggacgcat gacgagcggc   660
cgctcctagg agcagtatcg atcccagccc acttttcccc aatacgacta gtactcgact   720
gtgccttcta gttgccagcc atctgttgtt tgcccctccc ccgtgccttc cttgaccctg   780
gaaggtgcca ctcccactgt cctttcctaa taaaatgagg aaattgcatc gcattgtctg   840
agtaggtgtc attctattct ggggggtggg gtggggcagg acagcaaggg ggaggattgg   900
gaagacaaca gcaggcatgc tggggatgcg gtgggctcta tggcttctga ggcggaaaga   960
accagctttg gacgcgtctt aag                                            983

<210> SEQ ID NO 23
<211> LENGTH: 983
<212> TYPE: DNA
<213> ORGANISM: Artificial Sequence
<220> FEATURE:
<223> OTHER INFORMATION: Codon-optimized nucleotide sequence encoding
      FXN GenScript for cloning into pTRs-KS-CBh-EGFP-BGH scAAV vector

<400> SEQUENCE: 23
tagaagaccg gtcgccacca tgtggacact gggccggaga gccgtcgctg ggctgctggc    60
atcaccatcc cccgcacagg cacagaccct gacaagagtc cctcggccag cagagctggc   120
cccactgtgc gggcggagag gactgcgaac cgacatcgat gctacttgta ccccaaggcg   180
agcaagctcc aaccagcgag ggctgaacca gatttggaat gtgaagaaac agtctgtcta   240
cctgatgaat ctgagaaaga gcggcactct gggacaccct ggcagcctgg acgagaccac   300
ctacgagcgg ctggccgagg aaaccctgga ttccctggcc gagttctttg aagacctggc   360
tgataagcca tacaccttcg aagactatga cgtgagcttc ggcagcggcg tgctgacagt   420
caaactgggc gggacctgg aacatacgt gatcaacaag cagactccta acaagcagat   480
ttggctgtct agtccctcaa gcggccctaa gaggtacgac tggacaggga aaaactgggt   540
gtatagtcac gatggcgtct cactgcatga gctgctggcc gctgaactga ctaaagccct   600
gaaaactaaa ctggacctgt cttccctggc atactctggc aaggacgcct gacgagcggc   660
cgctcctagg agcagtatcg atcccagccc acttttcccc aatacgacta gtactcgact   720
gtgccttcta gttgccagcc atctgttgtt tgcccctccc ccgtgccttc cttgaccctg   780
gaaggtgcca ctcccactgt cctttcctaa taaaatgagg aaattgcatc gcattgtctg   840
agtaggtgtc attctattct ggggggtggg gtggggcagg acagcaaggg ggaggattgg   900
gaagacaaca gcaggcatgc tggggatgcg gtgggctcta tggcttctga ggcggaaaga   960
accagctttg gacgcgtctt aag                                            983
```

```
<210> SEQ ID NO 24
<211> LENGTH: 983
<212> TYPE: DNA
<213> ORGANISM: Artificial Sequence
<220> FEATURE:
<223> OTHER INFORMATION: Codon-optimized nucleotide sequence encoding
      FXN GenScript (low CpG) for cloning into pTRs-KS-CBh-EGFP-BGH
      scAAV vector

<400> SEQUENCE: 24
tagaagaccg gtcgccacca tgtggactct gggccggaga gcagtggcag gactgctggc      60
aagtccatca cctgctcagg cacagactct gacaagagtc ccaagacctg cagagctggc     120
tccactgtgc gggaggcgcg gactgagaac agacatcgat gctacatgta ctcctcgacg     180
ggcaagctcc aaccagcgag ggctgaacca gatttggaat gtgaagaaac agtccgtcta     240
cctgatgaat ctgaggaagt caggcaccct ggggcaccca ggaagtctgg acgagaccac     300
atatgaacgg ctggctgagg aaacactgga ttctctggcc gagttctttg aagacctggc     360
tgataagccc tacacattcg aagactatga tgtgagcttt ggatccggcg tgctgactgt     420
caaactgggc ggggacctgg gcacttacgt gatcaacaag cagacccccta caagcagat     480 ttggctgtct agtccttcaa gcggaccaaa gcggtacgac tggaccggca aaaactgggt     540
gtattctcac gatggggtca gtctgcatga gctgctggcc gctgaactga ccaaggccct     600
gaagacaaaa ctggacctgt cctctctggc atatagcgga aaagatgcct gacgagcggc     660
cgctcctagg agcagtatcg atcccagccc acttttcccc aatacgacta gtactcgact     720
gtgccttcta gttgccagcc atctgttgtt tgcccctccc ccgtgccttc cttgaccctg     780
gaaggtgcca ctcccactgt cctttcctaa taaaatgagg aaattgcatc gcattgtctg     840
agtaggtgtc attctattct gggggtggg gtggggcagg acagcaaggg ggaggattgg     900
gaagacaaca gcaggcatgc tggggatgcg gtgggctcta tggcttctga ggcggaaaga     960
accagctttg gacgcgtctt aag                                            983

<210> SEQ ID NO 25
<211> LENGTH: 20
<212> TYPE: DNA
<213> ORGANISM: Artificial Sequence
<220> FEATURE:
<223> OTHER INFORMATION: Nucleic acid sequence encoding collagen
      stabilizing sequence

<400> SEQUENCE: 25
cccagcccac ttttcccaa                                                  20

<210> SEQ ID NO 26
<211> LENGTH: 797
<212> TYPE: DNA
<213> ORGANISM: Artificial Sequence
<220> FEATURE:
<223> OTHER INFORMATION: Nucleic acid sequence of CBh promoter

<400> SEQUENCE: 26
tacataactt acggtaaatg gcccgcctgg ctgaccgccc aacgaccccc gcccattgac      60
gtcaatagta acgccaatag ggactttcca ttgacgtcaa tgggtggagt atttacggta     120
aactgcccac ttggcagtac atcaagtgta tcatatgcca gtacgcccc ctattgacgt      180 caatgacggt aaatggcccg cctggcattg tgcccagtac atgaccttat ggactttcc      240 tacttggcag tacatctacg tattagtcat cgctattacc atggtcgagg tgagccccac     300
```

```
gttctgcttc actctcccca tctcccccc ctccccaccc ccaatttgt atttatttat      360 tttttaatta ttttgtgcag cgatggggc ggggggggg ggggggcgcg cgccaggcgg      420
ggcggggcgg ggcgagggc gggcgggc gaggcggaga ggtgcggcgg cagccaatca      480
gagcggcgcg ctccgaaagt ttccttttat ggcgaggcgg cggcggcggc ggccctataa      540
aaagcgaagc gcgcggcggg cgggagtcgc tgcgacgctg ccttcgcccc gtgccccgct      600
ccgccgccgc ctcgcgccgc ccgccccggc tctgactgac cgcgttactc ccacaggtga      660
gcgggcggga cggcccttct cctccgggct gtaattagct gagcaagagg taagggttta      720
agggatggtt ggttggtggg gtattaatgt ttaattaccc ggagcacctg cctgaaatca      780
ctttttttca ggttgga                                                   797

<210> SEQ ID NO 27
<211> LENGTH: 254
<212> TYPE: DNA
<213> ORGANISM: Artificial Sequence
<220> FEATURE:
<223> OTHER INFORMATION: Nucleic acid sequence of bGHpoly A signal
      sequence

<400> SEQUENCE: 27
ctcgactgtg ccttctagtt gccagccatc tgttgtttgc ccctcccccg tgccttcctt       60
gaccctggaa ggtgccactc ccactgtcct ttcctaataa aatgaggaaa ttgcatcgca      120
ttgtctgagt aggtgtcatt ctattctggg gggtggggtg gggcaggaca gcaagggga      180 ggattgggaa gacaacagca ggcatgctgg ggatgcggtg ggctctatgg cttctgaggc      240
ggaaagaacc agct                                                      254

<210> SEQ ID NO 28
<211> LENGTH: 2208
<212> TYPE: DNA
<213> ORGANISM: Artificial Sequence
<220> FEATURE:
<223> OTHER INFORMATION: Nucleotide sequence encoding AAV2i8 capsid
      (VP1)

<400> SEQUENCE: 28
atggctgccg atggttatct tccagattgg ctcgaggaca ctctctctga aggaataaga       60
cagtggtgga agctcaaacc tggcccacca ccaccaaagc ccgcagagcg gcataaggac      120
gacagcaggg gtcttgtgct tcctgggtac aagtacctcg gacccttcaa cggactcgac      180
aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt ggggcaacc tcggacgagc agtcttccag      360
gcgaaaaaga gggttcttga acctctgggc ctggttgagg aacctgttaa gacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
tcagtacctg accccagcc tctcggacag ccaccagcag ccccctctgg tctgggaact      600
aatacgatgg ctacaggcag tggcgcacca atggcagaca taacgagggg cgccgacgga      660
gtgggtaatt cctcgggaaa ttggcattgc gattccacat ggatgggcga cagagtcatc      720
accaccagca cccgaacctg ggcctgcc cctacaacca ccacctcta caacaaatt      780 tccagccaat caggagcctc gaacgacaat cactactttg gctacagcac cccttggggg      840
```

```
tattttgact tcaacagatt ccactgccac ttttcaccac gtgactggca aagactcatc    900
aacaacaact ggggattccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctg tggccggacc cagtaacatg gctgtccagg gaaggaactg gcttcctgga   1440
ccctgttacc gccagcagcg agtatcaaag acatctgcgg ataacaacaa cagtgaattt   1500
gcttggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agcaacagaa cacagcacca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa             2208
```

<210> SEQ ID NO 29
<211> LENGTH: 735
<212> TYPE: PRT
<213> ORGANISM: Artificial Sequence
<220> FEATURE:
<223> OTHER INFORMATION: Amino acid sequence of AAV2i8 capsid (VP1)

<400> SEQUENCE: 29

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Pro Val Lys Thr Ala Pro Gly Lys Lys Arg
        130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Val
450                 455                 460

Ala Gly Pro Ser Asn Met Ala Val Gln Gly Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Phe Ala Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
530                 535                 540
```

| | | | | | | | | | | | | | | |
|---|---|---|---|---|---|---|---|---|---|---|---|---|---|---|
|Gln|Gly|Ser|Glu|Lys|Thr|Asn|Val|Asp|Ile|Glu|Lys|Val|Met|Ile|Thr|
|545| | | | |550| | | | |555| | | | |560|

Asp Glu Glu Glu Ile Arg Thr Thr Asn Pro Val Ala Thr Glu Gln Tyr
             565                570               575

Gly Ser Val Ser Thr Asn Leu Gln Gln Gln Asn Thr Ala Pro Ala Thr
          580               585               590

Ala Asp Val Asn Thr Gln Gly Val Leu Pro Gly Met Val Trp Gln Asp
    595               600               605

Arg Asp Val Tyr Leu Gln Gly Pro Ile Trp Ala Lys Ile Pro His Thr
   610              615               620

Asp Gly His Phe His Pro Ser Pro Leu Met Gly Gly Phe Gly Leu Lys
625              630               635            640

His Pro Pro Pro Gln Ile Leu Ile Lys Asn Thr Pro Val Pro Ala Asn
          645             650               655

Pro Ser Thr Thr Phe Ser Ala Ala Lys Phe Ala Ser Phe Ile Thr Gln
          660             665               670

Tyr Ser Thr Gly Gln Val Ser Val Glu Ile Glu Trp Glu Leu Gln Lys
       675              680               685

Glu Asn Ser Lys Arg Trp Asn Pro Glu Ile Gln Tyr Thr Ser Asn Tyr
   690              695               700

Asn Lys Ser Val Asn Val Asp Phe Thr Val Asp Thr Asn Gly Val Tyr
705              710               715            720

Ser Glu Pro Arg Pro Ile Gly Thr Arg Tyr Leu Thr Arg Asn Leu
          725             730               735

```
<210> SEQ ID NO 30
<211> LENGTH: 2208
<212> TYPE: DNA
<213> ORGANISM: Artificial Sequence
<220> FEATURE:
<223> OTHER INFORMATION: Nucleic acid encoding AAV2-TT capsid (VP1)

<400> SEQUENCE: 30
atggctgccg atggttatct tccagattgg ctcgaggaca ctctctctga aggaataaga      60
cagtggtgga agctcaaacc tggcccacca ccaccaaagc ccgcagagcg cataaggac     120 gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca ccacgccga cgcggagttt    300 caggagcgcc ttaaagaaga tacgtctttt gggggcaacc tcggacgagc agtcttccag    360
gcgaaaaaga ggattcttga acctctgggc ctggttgagg aacctgttaa dacggctccg    420
ggaaaaaaga ggccggtaga gcactctcct gcggagccag actcctcctc gggaaccgga    480
aagtcgggcc agcagcctgc aagaaaaaga ttgaattttg gtcagactgg agacgcagac    540
tcagtacctg accccagcc tctcggacag ccaccagcag cccctctgg tctgggaact     600 aatacgatgg cttcaggcag tggcgcacca atggcagaca taacgagg gcgccgacgga     660 gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg gctacagcac cccttggggg    840
tattttgact tcaacagatt ccactgccca ttttcaccac gtgactggca aagactcatc    900
aacaacaact gggggattcg acccaagaga ctcagcttca gctctttaa cattcaagtc    960 aaagaggtca cgcagaatga cggtacgacg acgattgcca ataaccttac cagcacggtt   1020
```

```
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg accgtctca tgaatcctct catcgaccag   1320
tacctgtatt acttgagcag aacaaacact ccaagtggaa ccaccacgat gtcaaggctt   1380
cagttttctc aggccggagc gagtgacatt cgggaccagt ctaggaactg cttcctgga   1440 ccctgttacc gccagcagcg agtatcaaag acagctgcgg ataacaacaa cagtgattac   1500
tcgtggactg gagctaccaa gtaccacctc aatggcagag actctctggt gaatccgggc   1560
ccggccatgg caagccacaa ggacgatgaa gaaaagtatt tccctcagag cggggttctc   1620
atctttggga agcaagactc aggaaaaaca aatgtggaca ttgaaaaggt catgattaca   1680
gacgaagagg aaatcaggac aaccaatccc gtggctacgg agcagtatgg ttctgtatct   1740
accaacctcc agagcggcaa cacacaagca gctacctcag atgtcaacac acaaggcgtt   1800
cttccaggca tggtctggca ggacagagat gtgtaccttc agggccccat ctgggcaaag   1860
attccacaca cggacggaca tttttcaccc ctctccctca tgggtggatt cggacttaaa   1920
caccctcctc acagattct catcaagaac ccccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa               2208
```

<210> SEQ ID NO 31
<211> LENGTH: 735
<212> TYPE: PRT
<213> ORGANISM: Artificial Sequence
<220> FEATURE:
<223> OTHER INFORMATION: Amino acid sequence of AAV2-TT capsid (VP1)

<400> SEQUENCE: 31

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
```

```
            145                 150                 155                 160
        Lys Ser Gly Gln Gln Pro Ala Arg Lys Arg Leu Asn Phe Gly Gln Thr
                        165                 170                 175
        Gly Asp Ala Asp Ser Val Pro Asp Pro Gln Pro Leu Gly Gln Pro Pro
                        180                 185                 190
        Ala Ala Pro Ser Gly Leu Gly Thr Asn Thr Met Ala Ser Gly Ser Gly
                        195                 200                 205
        Ala Pro Met Ala Asp Asn Asn Glu Gly Ala Asp Gly Val Gly Asn Ser
                        210                 215                 220
        Ser Gly Asn Trp His Cys Asp Ser Thr Trp Met Gly Asp Arg Val Ile
        225                 230                 235                 240
        Thr Thr Ser Thr Arg Thr Trp Ala Leu Pro Thr Tyr Asn Asn His Leu
                        245                 250                 255
        Tyr Lys Gln Ile Ser Ser Gln Ser Gly Ala Ser Asn Asp Asn His Tyr
                        260                 265                 270
        Phe Gly Tyr Ser Thr Pro Trp Gly Tyr Phe Asp Phe Asn Arg Phe His
                        275                 280                 285
        Cys His Phe Ser Pro Arg Asp Trp Gln Arg Leu Ile Asn Asn Asn Trp
                        290                 295                 300
        Gly Phe Arg Pro Lys Arg Leu Ser Phe Lys Leu Phe Asn Ile Gln Val
        305                 310                 315                 320
        Lys Glu Val Thr Gln Asn Asp Gly Thr Thr Thr Ile Ala Asn Asn Leu
                        325                 330                 335
        Thr Ser Thr Val Gln Val Phe Thr Asp Ser Glu Tyr Gln Leu Pro Tyr
                        340                 345                 350
        Val Leu Gly Ser Ala His Gln Gly Cys Leu Pro Pro Phe Pro Ala Asp
                        355                 360                 365
        Val Phe Met Val Pro Gln Tyr Gly Tyr Leu Thr Leu Asn Asn Gly Ser
                        370                 375                 380
        Gln Ala Val Gly Arg Ser Ser Phe Tyr Cys Leu Glu Tyr Phe Pro Ser
        385                 390                 395                 400
        Gln Met Leu Arg Thr Gly Asn Asn Phe Thr Phe Ser Tyr Thr Phe Glu
                        405                 410                 415
        Asp Val Pro Phe His Ser Ser Tyr Ala His Ser Gln Ser Leu Asp Arg
                        420                 425                 430
        Leu Met Asn Pro Leu Ile Asp Gln Tyr Leu Tyr Tyr Leu Ser Arg Thr
                        435                 440                 445
        Asn Thr Pro Ser Gly Thr Thr Thr Met Ser Arg Leu Gln Phe Ser Gln
                        450                 455                 460
        Ala Gly Ala Ser Asp Ile Arg Asp Gln Ser Arg Asn Trp Leu Pro Gly
        465                 470                 475                 480
        Pro Cys Tyr Arg Gln Gln Arg Val Ser Lys Thr Ala Ala Asp Asn Asn
                        485                 490                 495
        Asn Ser Asp Tyr Ser Trp Thr Gly Ala Thr Lys Tyr His Leu Asn Gly
                        500                 505                 510
        Arg Asp Ser Leu Val Asn Pro Gly Pro Ala Met Ala Ser His Lys Asp
                        515                 520                 525
        Asp Glu Glu Lys Tyr Phe Pro Gln Ser Gly Val Leu Ile Phe Gly Lys
                        530                 535                 540
        Gln Asp Ser Gly Lys Thr Asn Val Asp Ile Glu Lys Val Met Ile Thr
        545                 550                 555                 560
        Asp Glu Glu Glu Ile Arg Thr Thr Asn Pro Val Ala Thr Glu Gln Tyr
                        565                 570                 575
```

```
Gly Ser Val Ser Thr Asn Leu Gln Ser Gly Asn Thr Gln Ala Ala Thr
                580                 585                 590
Ser Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

<210> SEQ ID NO 32
<211> LENGTH: 2208
<212> TYPE: DNA
<213> ORGANISM: Artificial Sequence
<220> FEATURE:
<223> OTHER INFORMATION: Nucleic acid encoding AAV2-TT-S312N capsid (VP1)

<400> SEQUENCE: 32

```
atggctgccg atggttatct tccagattgg ctcgaggaca ctctctctga aggaataaga      60
cagtggtgga agctcaaacc tggcccacca ccaccaaagc ccgcagagcg cataaggac     120
gacagcaggg gtcttgtgct tcctgggtac aagtacctcg acccttcaa cggactcgac     180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga ggattcttga acctctgggc ctggttgagg aacctgttaa acggctccg     420
ggaaaaaaga ggccggtaga gcactctcct gcggagccag actcctcctc gggaaccgga    480
aagtcgggcc agcagcctgc aagaaaaaga ttgaattttg gtcagactgg agacgcagac    540
tcagtacctg acccccagcc tctcggacag ccaccagcag cccctctgg tctgggaact    600
aatacgatgg cttcaggcag tggcgcacca atggcagaca taacgaggg cgccgacgga    660
gtgggtaatt cctcgggaaa ttggcattgc gattccacat ggatgggcga cagagtcatc    720
accaccagca cccgaacctg gcccctgcc cctacaaca ccacctcta caacaaatt      780
tccagccaat caggagcctc gaacgacaat cactactttg gctacagcac cccttggggg    840
tatttgact tcaacagatt ccactgccac ttttcaccac gtgactggca agactcatc     900
aacaacaact ggggattccg acccaagaga ctcaacttca gctctttaa cattcaagtc     960
aaagaggtca cgcagaatga cggtacgacg acgattgcca ataaccttac agcaccggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcacctg    1140
```

```
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg daccgtctca tgaatcctct catcgaccag    1320
tacctgtatt acttgagcag aacaaacact ccaagtggaa ccaccacgat gtcaaggctt    1380
cagttttctc aggccggagc gagtgacatt cgggaccagt ctaggaactg gcttcctgga    1440
ccctgttacc gccagcagcg agtatcaaag acagctgcgg ataacaacaa cagtgattac    1500
tcgtggactg gagctaccaa gtaccacctc aatggcagag actctctggt gaatccgggc    1560
ccggccatgg caagccacaa ggacgatgaa gaaaagtatt tccctcagag cggggttctc    1620
atctttggga agcaagactc aggaaaaaca atgtggaca ttgaaaaggt catgattaca    1680
gacgaagagg aaatcaggac aaccaatccc gtggctacgg agcagtatgg ttctgtatct    1740
accaacctcc agagcggcaa cacacaagca gctacctcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac acccccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 33
<211> LENGTH: 735
<212> TYPE: PRT
<213> ORGANISM: Artificial Sequence
<220> FEATURE:
<223> OTHER INFORMATION: Amino acid sequence of AAV2-TT-S312N capsid (VP1)

<400> SEQUENCE: 33

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
145                 150                 155                 160

Lys Ser Gly Gln Gln Pro Ala Arg Lys Arg Leu Asn Phe Gly Gln Thr
```

-continued

```
              165                 170                 175
Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Ser Gly Ser Gly
                195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Met Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ala Ala Asp Asn Asn
                485                 490                 495

Asn Ser Asp Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Tyr Phe Pro Gln Ser Gly Val Leu Ile Phe Gly Lys
            530                 535                 540

Gln Asp Ser Gly Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Ser Gly Asn Thr Gln Ala Ala Thr
            580                 585                 590
```

-continued

```
Ser Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625             630                 635                 640
His Pro Pro Pro Gln Ile Leu Ile Lys Asn Thr Pro Val Pro Ala Asn
            645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705             710                 715                 720
Ser Glu Pro Arg Pro Ile Gly Thr Arg Tyr Leu Thr Arg Asn Leu
            725                 730                 735
```